US009477307B2

(12) United States Patent
Chizeck et al.

(10) Patent No.: US 9,477,307 B2
(45) Date of Patent: Oct. 25, 2016

(54) METHODS AND SYSTEMS FOR SIX DEGREE-OF-FREEDOM HAPTIC INTERACTION WITH STREAMING POINT DATA

(71) Applicant: University of Washington through its Center for Commercialization, Seattle, WA (US)

(72) Inventors: Howard Jay Chizeck, Mercer Island, WA (US); Fredrik Ryden, Seattle, WA (US)

(73) Assignee: The University of Washington, Seattle, WA (US)

( * ) Notice: Subject to any disclaimer, the term of this patent is extended or adjusted under 35 U.S.C. 154(b) by 124 days.

(21) Appl. No.: 14/164,114

(22) Filed: Jan. 24, 2014

(65) Prior Publication Data
US 2014/0320489 A1 Oct. 30, 2014

Related U.S. Application Data

(60) Provisional application No. 61/756,132, filed on Jan. 24, 2013, provisional application No. 61/764,908, filed on Feb. 14, 2013, provisional application No. 61/764,921, filed on Feb. 14, 2013.

(51) Int. Cl.
G06F 3/01 (2006.01)
G06T 15/04 (2011.01)
H04N 5/225 (2006.01)

(52) U.S. Cl.
CPC ............ *G06F 3/016* (2013.01); *A61B 34/25* (2016.02); *G06T 15/04* (2013.01); *H04N 5/2256* (2013.01)

(58) Field of Classification Search
None
See application file for complete search history.

(56) References Cited

U.S. PATENT DOCUMENTS

| 5,634,039 A | 5/1997 | Simon et al. |
| 6,084,587 A | 7/2000 | Tarr et al. |
| 6,104,158 A | 8/2000 | Jacobus et al. |

(Continued)

FOREIGN PATENT DOCUMENTS

| EP | 2721463 | 4/2012 |
| WO | 9520788 | 8/1995 |

(Continued)

OTHER PUBLICATIONS

Fredrik et al., "Proxy Method for Fast Haptic Rendering from Time Varying Point Clouds," 2011, IEEE/RJS International Conference on Intelligent Robots and Systems, Sep. 25-30, 2011.*

(Continued)

*Primary Examiner* — Kee M Tung
*Assistant Examiner* — Nicholas R Wilson
(74) *Attorney, Agent, or Firm* — McDonnell Boehnen Hubert & Berghoff LLP

(57) ABSTRACT

Methods, articles of manufacture, and devices related to generating six degree of freedom (DOF) haptic feedback are provided. A computing device can receive first depth data about an environment. The computing device can generate a first plurality of points from the first depth data. The computing device can determine a virtual tool, where the virtual tool is specified in terms of a translation component for the virtual tool and a rotation component for the virtual tool. The computing device can determine a first force vector between the virtual tool and the first plurality of points. The computing device can send a first indication of haptic feedback based on the first force vector.

20 Claims, 30 Drawing Sheets

(56) References Cited

U.S. PATENT DOCUMENTS

| | | | |
|---|---|---|---|
| 6,191,796 | B1 | 2/2001 | Tarr |
| 6,421,048 | B1 | 7/2002 | Shih et al. |
| 6,597,347 | B1 | 7/2003 | Yasutake |
| 6,704,694 | B1 | 3/2004 | Basdogan et al. |
| 7,084,867 | B1 | 8/2006 | Ho et al. |
| 7,084,869 | B2 | 8/2006 | Sriram et al. |
| 7,191,014 | B2 | 3/2007 | Kobayashi et al. |
| 7,885,732 | B2 | 2/2011 | Troy |
| 8,398,541 | B2 | 3/2013 | DiMaio et al. |
| 2003/0112281 | A1 | 6/2003 | Sriram et al. |
| 2005/0065658 | A1 | 3/2005 | Green |
| 2005/0148432 | A1 | 7/2005 | Carmein |
| 2006/0049939 | A1 | 3/2006 | Haberer et al. |
| 2006/0142657 | A1* | 6/2006 | Quaid et al. .............. 600/424 |
| 2007/0142751 | A1 | 6/2007 | Kang et al. |
| 2007/0142968 | A1 | 6/2007 | Prisco et al. |
| 2008/0218514 | A1 | 9/2008 | Tarr et al. |
| 2008/0240502 | A1 | 10/2008 | Freedman et al. |
| 2009/0278915 | A1 | 11/2009 | Kramer et al. |
| 2010/0063630 | A1 | 3/2010 | Sutherland |
| 2011/0066406 | A1 | 3/2011 | Tsai et al. |
| 2011/0119224 | A1* | 5/2011 | Mangione-Smith .......... 706/52 |
| 2012/0109150 | A1 | 5/2012 | Quaid |
| 2013/0096575 | A1 | 4/2013 | Olson |
| 2013/0147789 | A1* | 6/2013 | Kim .......................... 345/419 |
| 2013/0169423 | A1 | 7/2013 | Iorgulescu et al. |
| 2013/0218472 | A1* | 8/2013 | Fu et al. ........................ 702/5 |
| 2013/0286004 | A1* | 10/2013 | McCulloch et al. ........ 345/419 |
| 2014/0168073 | A1 | 6/2014 | Chizeck et al. |
| 2014/0320392 | A1 | 10/2014 | Chizeck et al. |
| 2014/0320489 | A1 | 10/2014 | Chizeck et al. |
| 2014/0320629 | A1 | 10/2014 | Chizeck et al. |

FOREIGN PATENT DOCUMENTS

| | | | |
|---|---|---|---|
| WO | 2008120217 | A2 | 10/2008 |
| WO | 2009045827 | A2 | 4/2009 |
| WO | WO 2012126135 | A1 * | 9/2012 |
| WO | 2012174406 | | 12/2012 |
| WO | 2013033122 | A1 | 3/2013 |
| WO | 2015134391 | | 9/2015 |

OTHER PUBLICATIONS

El-Far et al., "An Algorithm for Haptically Rendering Objects Described by Point Clouds," IEEE, 2008.*
Kim et al., "Haptic Rendering of Point Set Surfaces," IEEE 2007.*
Inglese, Francoix-Xavier, et al., "A human-scale virtual environment with haptic feedback." Proc. ICINCO. vol. 4. 2005.*
Klein et al., "Point Cloud Collision Detection," EUROGRAPHICS, vol. 23, No. 3, 2004.*
Leeper et al., "Constraint based 3-dof haptic rendering of arbitrary point cloud data." RSS Workshop on RGB-D Cameras. 2011.*
Kuang et al., "Assembling Virtual Fixtures for Guidance in Training Environments," IEEE, 2004.*
McNeely et al., "Six Degree-of-Freedom Haptic Rendering Using Voxel Sampling," ACM, 1999.*
Kwok, G. Mylonas, L. Sun, M. Lerotic, J. Clark, T. Athanasiou, A. Darzi, and G. Yang, "Dynamic active constraints for hyper-redundant flexible robots," Medical Image Computing and Computer-Assisted Intervention—MICCAI 2009, pp. 410-417, 2009.
Bettini, S. Lang, A. Okamura, and G. Hager, "Vision assisted control for manipulation using virtual fixtures," vol. 2, pp. 1171-1176. [Online]. Available:http://ieeexplore.ieee.org/xpl/arricleDetails.jsp?arnumber=976327, Oct. 29-Nov. 3, 2001.
Marayong and A. Okamura, "Speed-accuracy characteristics of human-machine cooperative manipulation using virtual fixtures with variable admittance," Human Factors: The Journal of the Human Factors and Ergonomics Society, vol. 46, No. 3, pp. 518-532, 2004.
Li, M. Ishii, and R. H. Taylor, "Spatial motion constraints using virtual fixtures generated by anatomy," Robotics, IEEE Transactions on, vol. 23, No. 1, pp. 4-19, Feb. 2007.
Kragic, P. Marayong, M. Li, A. Okamura, and G. Hager, "Human-machine collaborative systems for microsurgical applications," The International Journal of Robotics Research, vol. 24, No. 9, pp. 731-741, 2005.
Park, R. Howe, and D. Torchiana, "Virtual fixtures for robotic cardiac surgery," pp. 1419-1420, 2001.
Peshkin, J. Colgate, W. Wannasuphoprasit, C. Moore, R. Gillespie, and P. Akella, "Cobot architecture," Robotics and Automation, IEEE Transactions on, vol. 17, No. 4, pp. 377-390, 2001.
Davies, M. Jakopec, S. Harris, F. Rodriguez y Baena, A. Barrett, A. Evangelidis, P. Gomes, J. Henckel, and J. Cobb, "Active-constraint robotics for surgery," Proceedings of the IEEE, vol. 94, No. 9, pp. 1696-1704, 2006.
Becker, R. MacLachlan, G. Hager, and C. Riviere, "Handheld micromanipulation with vision-based virtual fixtures," in Robotics and Automation (ICRA), 2011 IEEE International Conference on, May 2011, pp. 4127-4132.
Dewan, P. Marayong, A. Okamura, and G. Hager, "Vision-based assistance for ophthalmic micro-surgery," in Medical Image Computing and Computer-Assisted Intervention MICCAI 2004, ser. Lecture Notes in Computer Science, C. Barillot, D. Haynor, and P. Hellier, Eds. Springer Berlin / Heidelberg, 2004, vol. 3217, pp. 49-57.
Li, A. Kapoor, and R. Taylor, "A constrained optimization approach to virtual fixtures," in Intelligent Robots and Systems, 2005. (IROS 2005). 2005 IEEE/RSJ International Conference on, Aug. 2005, pp. 1408-1413.
Park, J. Choi, Y. Park, and K. Sun, "Haptic virtual fixture for robotic cardiac catheter navigation," Artificial Organs, vol. 35, No. 11, pp. 1127-1131, 2011. [Online]. Available: http://dx.doi.org/10.1111/j.1525-1594.2011.01373.x.
Yamamoto, N. Abolhassani, S. Jung, A. Okamura, and T. Judkins, "Augmented reality and haptic interfaces for robot-assisted surgery," The International Journal of Medical Robotics and Computer Assisted Surgery, 2011.
Gibo, L. N. Verner, D. D. Yuh, and A. M. Okamura, "Design considerations and human-machine performance of moving virtual fixtures,"in Robotics and Automation, 2009. ICRA '09. IEEE International Conference on, May 2009, pp. 671-676.
Ren, R. Patel, K. McIsaac, G. Guiraudon, and T. Peters, "Dynamic 3-d virtual fixtures for minimally invasive beating heart procedures," Medical Imaging, IEEE Transactions on, vol. 27, No. 8, pp. 1061-1070, Aug. 2008.
King, B. Hannaford, K.-W. Kwok, G.-Z. Yang, P. Griffiths, A. Okamura, I. Farkhatdinov, J.-H. Ryu, G. Sankaranarayanan, V. Arikatla, K. Tadano, K. Kawashima, A. Peer, T. Schauss, M. Buss, L. Miller, D. Glozman, J. Rosen, and T. Low, "Plugfest 2009: Global interoperability in telerobotics and telemedicine," in Robotics and Automation (ICRA), 2010 IEEE International Conference on, May 2010, pp. 1733-1738.
Quigley, B. Gerkey, K. Conley, J. Faust, T. Foote, J. Leibs, E. Berger, R. Wheeler, and A. Ng, "Ros: an open-source robot operating system," in ICRA workshop on open source software, vol. 3, No. 3.2, 2009.
Kosari, S. Ramadurai, H. J. Chizeck and B. Hannaford, "Robotic Compression of Soft Tissue," in International Conference on Robotics and Automation (IROS). IEEE, 2012.
Ramadurai, S. N. Kosari, H. H. King, H. J. Chizeck, B. Hannaford, "Application of Unscented Kalman Filter to a Cable Driven Surgical Robot: A Simulation Study," in International Conference on Robotics and Automation (IROS). IEEE, 2012.
Rydén and H. J. Chizeck, "A Method for COntraint-Based Six Degree-of-freedom Haptic Interaction with Streaming Point Clouds," IEEE Trans. on Robotics and Engineering, 2013.
Daniel Herrera C., Juho Kannala, and Janne Heikkila, Accurate and Practical Calibration of a Depth and Color Camera Pair CAIP 2011, Part II, LNCS 6855, pp. 437-445, 2011.
Helferty, C. Zhang, G. McLennan, and W. E. Higgins "Videoendoscopic Distortion Correction and Its Application to Virtual Guidance of Endoscopy ," IEEE Transaction on Medical Imaging , vol. 20, No. 7.

(56) References Cited

OTHER PUBLICATIONS

Ryden, et al., 'Proxy Method for Real-Time 3-DOF Haptic Rendering from streaming Point cloud data, IEEE Transactions on Haptics, 6(3): 257-267, 2013.

Tassa, Y. and Erez, T. and Todorov, E. Fast Model Predictive Control for Reactive Robotic Swimming. 2011.

Zhou, MA et al., An Exoskeleton Glove Mechanism for Mobile Robot Navigation through Haptics Feedback, IEEE/ASME Transactions on Mechatronics (2013).

Diolaiti, Nicola et al., Haptic Teleoperation of a Mobile Robot, IFAC Symp. on Robot Control 2798-805 (2003).

Buss, Martin et al., Multi-Modal Multi-User Telepresence and Teleaction System, IEEE/RSJ Int'l Conf. on Intelligent Robots and Sys. 4137-38 (Sep. 2008).

Johnson and P. Willemsen, "Six degree-of-freedom haptic rendering of complex polygonal models," in Haptic Interfaces for Virtual Environment and Teleoperator Systems, 2003. HAPTICS 2003. Proceedings. 11th Symposium on. IEEE, 2003, pp. 229-235.

Otaduy and M. Lin, "Introduction to haptic rendering," in ACM SIGGRAPH 2005 Courses. ACM, 2005, p. 3.

Johnson, P. Willemsen, and E Cohen, "Six degree-of-freedom haptic rendering using spatialized normal cone search," Visualization and Computer Graphics, IEEE Transactions on, vol. 11, No. 6, pp. 661-670, 2005.

Nelson, D. Johnson, and E. Cohen, "Haptic rendering of surfaceto-surface sculpted model interaction," in ACM SIGGRAPH 2005 Courses. ACM, 2005, p. 97.

Colgate, M. Stanley, and J. Brown, "Issues in the haptic display of tool use," in Intelligent Robots and Systems 95.'Human Robot Interaction and Cooperative Robots', Proceedings. 1995 IEEE/RSJ International Conference on, vol. 3. IEEE, 1995, pp. 140-145.

Zilles and J. Salisbury, "A constraint-based god-object method for haptic display," in Intelligent Robots and Systems 95.'Human Robot Interaction and Cooperative Robots', Proceedings. 1995 IEEE/RSJ International Conference on, vol. 3. IEEE, 1995, pp. 146-151.

Baraff, "Analytical methods for dynamic simulation of nonpenetrating rigid bodies," in ACM SIGGRAPH Computer Graphics, vol. 23, No. 3. ACM, 1989, pp. 223-232.

Ruspini and O. Khatib, "Collision/contact models for the dynamic simulation of complex environments," in Proc. IEEE/RSJ Int. Conf. on Intelligent Robots and Systems, vol. 82. Citeseer, 1997.

Redon, A. Kheddar, and S. Coquillart, "Gauss' least constraints principle and rigid body simulations," in Robotics and Automation, 2002. Proceedings. ICRA'02. IEEE International Conference on, vol. 1. IEEE, 2002, pp. 517-522.

McNeely, K. Puterbaugh, and J. Troy, "Six degree-of-freedom haptic rendering using voxel sampling," in Proceedings of the 26th annual conference on Computer graphics and interactive techniques. ACM Press/Addison-Wesley Publishing Co., 1999, pp. 401-408.

Gregory, A. Mascarenhas, S. Ehmann, M. Lin, and D. Manocha, "Six degree-of-freedom haptic display of polygonal models," in Proceedings of the conference on Visualization'00. IEEE Computer Society Press, 2000, pp. 139-146.

Wan and W. McNeely, "Quasi-static approximation for 6 degrees-of-freedom haptic rendering," in Proceedings of the 14th IEEE Visualization 2003 (VIS'03). IEEE Computer Society, 2003, p. 34.

Hasegawa and M. Sato, "Real-time rigid body simulation for haptic interactions based on contact volume of polygonal objects," in Computer Graphics Forum, vol. 23, No. 3. Wiley Online Library, 2004, pp. 529-538.

Otaduy and M. Lin, "Sensation preserving simplification for haptic rendering," in ACM SIGGRAPH 2005 Courses. ACM, 2005, p. 72.

Otaduy, et al., "A modular haptic rendering algorithm for stable and transparent 6-dof manipulation," Robotics, IEEE Transactions on, vol. 22, No. 4, pp. 751-762, 2006.

McNeely, K. Puterbaugh, and J. Troy, "Voxel-based 6-dof haptic rendering improvements," Haptics-e, vol. 3, No. 7, 2006.

Barbi and D. James, "Time-critical distributed contact for 6-dof haptic rendering of adaptively sampled reduced deformable models," 2007.

Kolesnikov and M. Zefran, "Energy-based 6-dof penetration depth computation for penalty-based haptic rendering algorithms," in Intelligent Robots and Systems, 2007. IROS 2007. IEEE/RSJ International Conference on. IEEE, 2007, pp. 2120-2125.

Barbic and D. James, "Six-dof haptic rendering of contact between geometrically complex reduced deformable models," Haptics, IEEE Transactions on, vol. 1, No. 1, pp. 39-52, 2008.

He and Y. Chen, "Six-degree-of-freedom haptic rendering in virtual teleoperation," Instrumentation and Measurement, IEEE Transactions on, vol. 57, No. 9, pp. 1866-1875, 2008.

Mirtich and J. Canny, "Impulse-based simulation of rigid bodies," in Proceedings of the 1995 symposium on Interactive 3D graphics. ACM, 1995, pp. 181-ff.

Chang and J. Colgate, "Real-time impulse-based simulation of rigid body systems for haptic display," in Proc. Symp. on Interactive 3D Graphics, 1997, pp. 200-209.

Constantinescu, S. Salcudean, and E. Croft, "Haptic rendering of rigid body collisions," in Haptic Interfaces for Virtual Environment and Teleoperator Systems, 2004. HAPTICS'04. Proceedings. 12th International Symposium on. IEEE, 2004, pp. 2-8.

Constantinescu, "Haptic rendering of rigid contacts using impulsive and penalty forces," Robotics, IEEE Transactions on, vol. 21, No. 3, pp. 309-323, 2005.

Ruffaldi, D. Morris, F. Barbagli, K. Salisbury, and M. Bergamasco, "Voxel-based haptic rendering using implicit sphere trees," in Haptic interfaces for virtual environment and teleoperator systems, 2008. haptics 2008. symposium on. IEEE, 2008, pp. 319-325.

Berkelman, R. Hollis, and D. Baraff, "Interaction with a real time dynamic environment simulation using a magnetic levitation haptic interface device," in Robotics and Automation, 1999. Proceedings. 1999 IEEE International Conference on, vol. 4. IEEE, 1999, pp. 3261-3266.

Ortega, S. Redon, and S. Coquillart, "A six degree-of-freedom god-object method for haptic display of rigid bodies," in Virtual Reality Conference, 2006. IEEE, 2006, pp. 191-198.

Ortega, et al. "A six degree-of-freedom god-object method for haptic display of rigid bodies with surface properties," Visualization and Computer Graphics, IEEE Transactions on, vol. 13, No. 3, pp. 458-469, 2007.

Chan, F. Conti, N. Blevins, and K. Salisbury, "Constraint-based six degree-of-freedom haptic rendering of volume-embedded isosurfaces," in Proc. of the 2011 IEEE International World Haptics Conference, 2011.

Zhang, D. Wang, Y. Zhang, and J. Xiao, "Configuration-based optimization for six degree-of-freedom haptic rendering using spheretrees," in Intelligent Robots and Systems (IROS), 2011 IEEE/RSJ International Conference on. IEEE, 2011, pp. 2602-2607.

Wang, X. Zhang, Y. Zhang, and J. Xiao, "Configuration-based optimization for six degree-of-freedom haptic rendering for fine manipulation," in Robotics and Automation (ICRA), 2011 IEEE International Conference on. IEEE, 2011, pp. 906-912.

Wang, S. Liu, X. Zhang, Y. Zhang, and J. Xiao, "Six-degree-of-freedom haptic simulation of organ deformation in dental operations," in Robotics and Automation (ICRA), 2012 IEEE International Conference on. IEEE, 2012, pp. 1050-1056.

Ryden, S. Nia Kosari, and H. Chizeck, "Proxy method for fast haptic rendering from time varying point clouds," in Intelligent Robots and Systems (IROS), 2011 IEEE/RSJ International Conference on. IEEE, 2011, pp. 2614-2619.

Leeper, S. Chan, and K. Salisbury, "Point clouds can be represented as implicit surfaces for constraint-based haptic rendering," in Robotics and Automation (ICRA), 2012 IEEE International Conference on. IEEE, 2012, pp. 5000-5005.

Rasool and A. Sourin, "Haptic interaction with 2d images," in Proceedings of the 10th International Conference on Virtual Reality Continuum and Its Applications in Industry. ACM, 2011, pp. 13-22.

Ryden and H. Chizeck, "Forbidden-region virtual fixtures from streaming point clouds: Remotely touching and protecting a beating heart," in Intelligent Robots and Systems (IROS), 2012 IEEE/RSJ International Conference on. IEEE, 2012.

(56) References Cited

OTHER PUBLICATIONS

Leeper, S. Chan, K. Hsiao, M. Ciocarlie, and K. Salisbury, "Constraint-based haptic rendering of point data for teleoperated robot grasping," in Haptics Symposium (HAPTICS), 2012 IEEE, Mar. 2012, pp. 377-383.
Tomasi and R. Manduchi, "Bilateral filtering for gray and color images," in Computer Vision, 1998. Sixth International Conference on. IEEE, 1998, pp. 839-846.
Wendland, "Piecewise polynomial, positive definite and compactly supported radial functions of minimal degree," Advances in computational Mathematics, vol. 4, No. 1, pp. 389-396, 1995.
Wilhelmsen, "A nearest point algorithm," Mathematics of computation, vol. 30, No. 133, pp. 48-57, 1976.
Adams and B. Hannaford, "Stable haptic interaction with virtual environments," Robotics and Automation, IEEE Transactions on, vol. 15, No. 3, pp. 465-474, 1999.
N. Diolaiti, G. Niemeyer, F. Barbagli, and J. Salisbury, "Stability of haptic rendering: Discretization, quantization, time delay, and coulomb effects," Robotics, IEEE Transactions on, vol. 22, No. 2, pp. 256-268, 2006.
Kolesnikov and M. ˇ Zefran, "Generalized penetration depth for penalty-based six-degree-of-freedom haptic rendering," Robotica, vol. 26, No. 04, pp. 513-524, 2008.
Rosenberg, "Virtual fixtures: Perceptual tools for telerobotic manipulation," pp. 76-82, Sep. 1993.
Kitagawa, D. Dokko, A. Okamura, and D. Yuh, "Effect of sensorysubstitution on suturemanipulation forces for robotic surgical systems,"Journal of Thoracic and Cardiovascular Surgery, vol. 129, No. 1, pp. 151-158, 2005.
Navkar, Z. Deng, D. J. Shah, K. E. Bekris, and N. V. Tsekos, "Visual and force-feedback guidance for robot-assisted interventions in the beating heart with real-time MRI," pp. 689-694, May 2012.
Payandeh and Z. Stanisic, "On application of virtual fixtures as an aid for telemanipulation and training," in Haptic Interfaces for Virtual Environment and Teleoperator Systems, 2002. HAPTICS 2002. Proceedings. 10th Symposium on, 2002, pp. 18-23.
Adamson et al., "Approximating and Intersecting Surfaces from Points," Proceedings of the 2003 Eurographics/ACM SIGGRAPH Symposium on Geometry Processing (SGP '03), Jun. 2003, pp. 230-239.
Hua et al., "A 2-D Microdisplay Using an Integrated Microresonating Waveguide Scanning System," 20th International Conference on Adaptive Structures and Technologies, Hong Kong, Oct. 2009, pp. 53-62.
International Bureau, International Report on Patentability mailed on Jan. 3, 2014, issued in connection with International Application No. PCT/US2012/042716, filed on Jun. 12, 2012, 9 pages.
International Searching Authority, International Search Report and Written Opinion mailed on Sep. 25, 2012, issued in connection with International Application No. PCT/US2012/042716, filed on Jun. 12, 2012, 14 pages.
International Searching Authority, International Search Report and Written Opinion mailed on Dec. 11, 2015, issued in connection with International Application No. PCT/US2015/049781, filed on Sep. 11, 2015, 14 pages.
Levin, David, "The Approximation Power of Moving Least-Squares," Mathematics of Computation, Oct. 1998, pp. 1517-1531, vol. 67, No. 224.
Zhou et al., "An Exoskelton Glove Mechanism for Mobile Robot Navigation through Haptics Feedback," IEEE/ASME Transactions on Mechatronics, Apr. 2015, pp. 641-652, vol. 20, No. 2.
Abbott, et al., "Haptic virtual fixtures for robot-assisted manipulation," Robotics Research, pp. 49-64, 2007.
Abbott, et al., "Stable Forbidden-Region Virtual Fixtures for Bilateral Telemanipulation," Transactions of the ASME, Journal of Dynamic Systems, Measurement and Control, vol. 128, No. 1, pp. 53-64 , 2006.
Anderson, et al., "The Optics of Human Skin," Journal of Investigative Dermatology, vol. 77, pp. 13-19, 1981.
Basdogan, et al., "Haptic Rendering in Virtual Environments," in Handbook of Virtual Environments, K. Stanney (Ed.), Lawrence Earlbaum: London, 2002.
Brown, et al., "Mechanical design and analysis for a scanning fiber endoscope," Proceedings of the 2001 ASME International Mechanical Engineering Congress and Exposition, New York, NY, vol. 51, pp. 165-166, 2001.
Burrus, "Kinect Calibration," available online at: http://nicolas.burras.name/index.php/Research/KinectCalibration, 2010.
BWH and 3D Slicer, "3D Slicer," available online at: http://www.slicer.org, 2015.
Cha, et al., "Haptic Interaction with Depth Video Media," Advances in Multimedia Information Processing-PCM 2005, pp. 420-430, 2005.
Colgate, et al., "Passivity of a class of sampled-data systems: Application to haptic interfaces," Journal of Robotic Systems, vol. 14, No. 1, pp. 37-47, ISSN: 0741-2223, 1997.
EP 12733550.3, EP Office Action dated Feb. 13, 2015.
Helferty, et al., "Videoendoscopic Distortion Correction and Its Application to Virtual Guidance of Endoscopy," IEEE Transactions on Medical Imaging, vol. 20, No. 7, pp. 605-617, 2001.
Henry et al., "RGB-D Mapping: Using Depth Cameras for Dense 3D Modeling of Indoor Environments," in Proceedings of the 12th International Symposium on Experimental Robotics (ISER), 2010.
Herrera, et al., "Accurate and Practical Calibration of a Depth and Color Camera Pair," Computer Analysis of Images and Patterns, Part II, vol. 6855 of the series Lecture Notes in Computer Science, pp. 437-445, 2011.
Hua, et al., "Development of 2D Microdisplay Using an Integrated Microresonating Waveguide Scanning System," Journal of Intelligent Material Systems and Structures, vol. 22, No. 14, pp. 1613-1622, epub Jun. 2011.
Hua, et al., "Development of a novel polymeric waveguide and micro actuator for micro scanning system," 19th International Conference on Adaptive Structures and Technologies, Ascona, Switzerland, pp. 1-10, 2008.
Jacques, et al., "Absorption spectra for biological tissues," available online at: http://omlc.ogi.edu/classroom/ece532/class3/muaspectrahtml , 1998 (retrieved Oct. 2015).
Lloyd, et al., "Programming Contact Tasks Using a Reality-based Virtual Environment Integrated with Vision," in IEEE Transactions on Robotics and Automation, 1997.
Panergo, et al., "Resonant polymeric optical waveguide cantilever integrated for image acquisition," Journal of Lightwave Technology, vol. 25, No. 3, pp. 850-860, 2007.
PCT/US2012/042716, International Search Report and Written Opinion, Sep. 25, 2012.
PCT/US2015/018320, International Search Report and Written Opinion, Jun. 18, 2015.
Prime Sense LTD, "Reference design," available online at: http://www.primesense.com/?p=514, 2011.
Weissleder, "A clearer vision for in vivo imaging," Nature Biotechnology, vol. 19, pp. 316-317, 2001.
Ruspini, et al., "The haptic display of complex graphical environments," in Proceedings of the 24th annual conference on computer graphics and interactive techniques, pp. 345-352, 1997.
Rusu, et al., "3D is here: Point Cloud Library (PCL)," IEEE International Conference on Robotics and Automation (ICRA), pp. 1-4, 2011.
Ryden, (uploaded to YouTube Dec. 16, 2010) "Haptics using Kinect," available online at: https://www.youtube.com/watch?v=bcUCDns_7Qc, (retrieved on Feb. 9, 2015).
Ryden, et al., "A proxy method for real-time 3-dof haptic rendering of streaming point cloud data," IEEE Transactions on Haptics, vol. 6, No. 3, pp. 257-267, 2013.
Ryden, et al., "Advanced Telerobotic Underwater Manipulation Using Virtual Fixtures and Haptic Rendering," MTS/IEEE Oceans Conference, San Diego, CA, pp. 1-8, 2013.
Ryden, et al., "Proxy Method for Fast Haptic Rendering from Time Varying Point Clouds," 2011 IEEE/RSJ International conference on Intelligent Robots and Systems, pp. 2614-2619, 2011.
Ryden, et al., "Using KinectTM and a Haptic Interface for Implementation of Real-Time Virtual Fixtures," Proceedings of the 2nd

(56) References Cited

OTHER PUBLICATIONS

Workshop on RGB-D: Advanced Reasoning with Depth Cameras (in conjunction with RSS 2011), Los Angeles, CA, pp. 1-5, 2011.
Sehgal, et al., "Real-Time Scale Invariant 3D Range Point Cloud Registration," Image Analysis and Recognition, Springer: Berlin, pp. 220-229, 2010.
Seibel, et al., "Single fiber flexible endoscope: general design for small size, high resolution, and wide field of view," in Proceedings of SPIE, Biomonitoring and Endoscopy Technologies, vol. 4158, pp. 29-39, 2001.
Stanton, "New rules for humidity in the OR," AORN Journal (online), available at: http://www.aorn.org/News/Managers/May2010Issue/Humidity, 2010.
Takahashi, et al., "Polymeric waveguide design of 2D display system," SPIE NDE Health Monitoring and Diagnostics, vol. 6177, pp. 617719-1-617719-9 , 2006 (retrieved Oct. 2015).
Nang, et aL, "1-D electro-optic beam steering device," Sensors and Actuators A: Physical, vol. 188, pp. 277-284, 2012.
Wang et al., "1-D electro-optic beam steering device," 16th International Solid-State Sensors, Actuators and Microsystems Conference (TRANSDUCERS 2011), Beijing, China, pp. 1570-1573, 2011.
Nang, et al., "2-D Mechanically Resonating Fiberoptic Scanning Display System," 2010 International Symposium on Optomechatronic Technologies (ISOT), Toronto, Canada, pp. 1-6, 2010.
Wang et al., "Development of a microfabricated scanning endoscope using SU-8 based optical waveguide," SPIE NDE Health Monitoring and Diagnostics, vol. 5047, pp. 305-313, 2003.
Wang, et al., "Development of an electro-optic scanner for potential endoscope application," Journal of Medical Devices, vol. 3, No. 2, pp. 027522, 2009.
Wang, et al., "Development of an optical waveguide cantilever scanner," Proceedings of SPIE, vol. 4876, pp. 72-83, 2002.
Wang, et al., "Electro-optic polymer prism beam deflector," 21st Annual Meeting of the IEEE Lasers and Electro-Optics Society, Newport Beach, CA, pp. 579-580, 2008.
Wang, et al., "Electro-optic polymer prism beam deflector," Optical Engineering, vol. 48, No. 11, pp. 114601, 2009.
Wang, et al., "Micromachined optical waveguide cantilever as a resonant optical scanner," Sensors and Actuators A, vol. 102, pp. 165-175, 2002.
Wang, et al., "Scanning polymeric waveguide design of a 2D display system," IEEE Journal of Display Technology, vol. 4, No. 1, pp. 28-38 , 2008.
Wang, et al., "Two-dimensional mechanically resonating fiber optic scanning display system," Optical Engineering, vol. 49, No. 9, pp. 097401-1-097401-8, 2010.
Zhou et al. (Apr. 2015) "An Exoskeleton Glove Mechanism for Mobile Robot Navigation through Haptics Feedback," IEEE/ASME Transactions on Mechatronics, 20(2):641-652.
El-Far, et al. (2008) "An algorithm for Haptically Rendering Objects described by point clouds," IEEE, 001443-.

* cited by examiner

Example Degrees of Freedom for Tool 210
1. X coordinate
2. Y coordinate
3. Z coordinate
4. X rotation
5. Y rotation
6. Z rotation

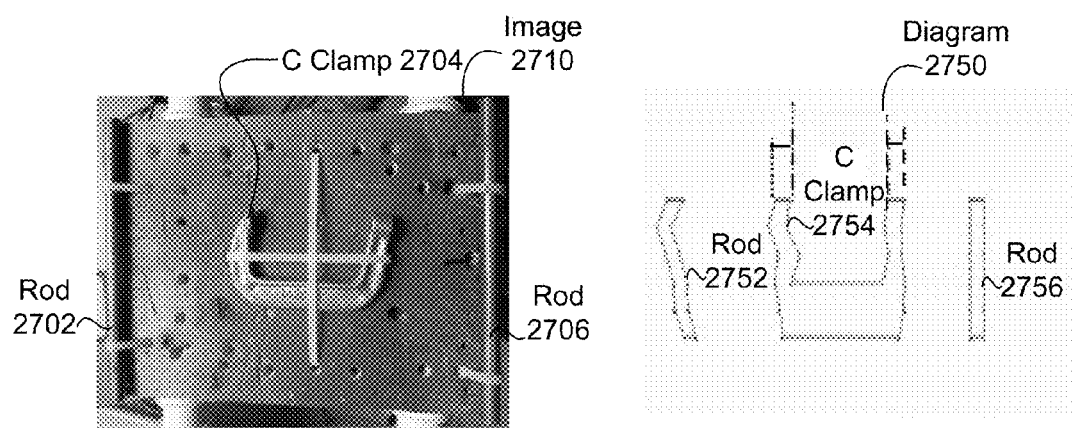
FIG. 27A
FIG. 27C
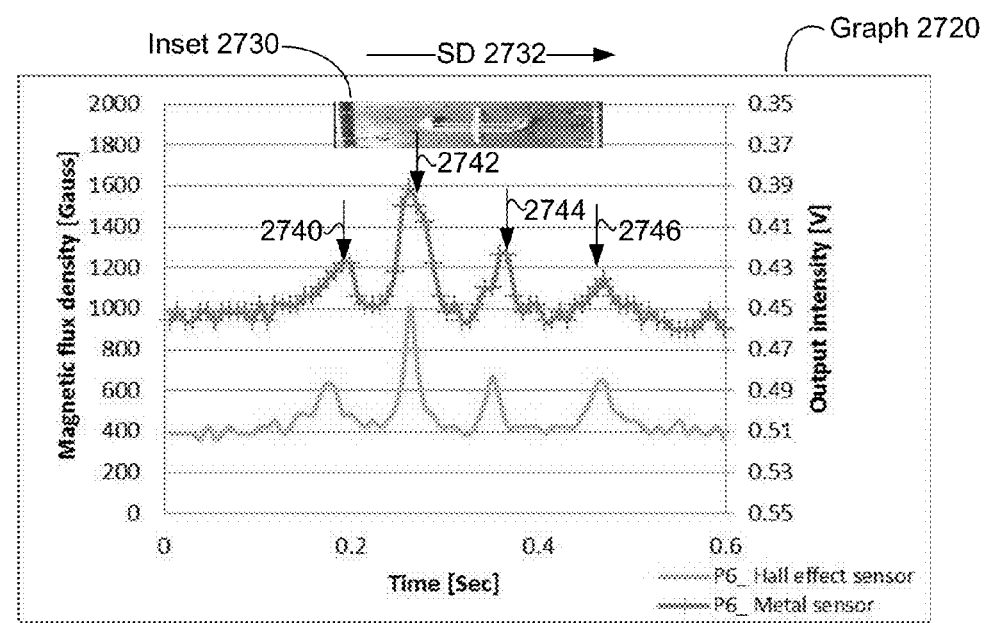
FIG. 27B

US 9,477,307 B2

METHODS AND SYSTEMS FOR SIX DEGREE-OF-FREEDOM HAPTIC INTERACTION WITH STREAMING POINT DATA

RELATED APPLICATIONS

The present application claims priority to U.S. Provisional Patent Application No. 61/756,132 entitled "Methods and Systems for Six Degree-of-Freedom Haptic Interaction with Streaming Point Clouds", filed Jan. 24, 2013, U.S. Provisional Patent Application No. 61/764,908 entitled "Methods for Underwater Haptic Rendering Using Nontact Sensors", filed Feb. 14, 2013, and U.S. Provisional Patent Application No. 61/764,921 entitled "Virtual Fixtures for Subsea Technology", filed Feb. 14, 2013, all of which are entirely incorporated by reference herein for all purposes.

STATEMENT OF GOVERNMENT RIGHTS

This invention was made with government support under grant no. 0930930, awarded by the National Science Foundation and with support under grant no. W912HQ-12-P-0117, awarded by the Department of Defense. The United States Government has certain rights in the invention.

BACKGROUND OF THE INVENTION

Unless otherwise indicated herein, the materials described in this section are not prior art to the claims in this application and are not admitted to be prior art by inclusion in this section.

Haptic rendering is the translation of forces in a virtual environment to a physical device that can provide touch-based, a.k.a. haptic, feedback to a user of the haptic rendering device. Both impedance type and admittance type haptic rendering devices are available.

To provide haptic feedback about the virtual environment, objects in the virtual environment are often represented as a collection of polygons, such as triangles, that can be operated upon using a haptic rendering device. The haptic rendering device can be controlled using a "Haptic Interaction Point" (HIP) in the virtual environment, which performs a similar function for the haptic rendering device as a mouse pointer does for a computer mouse. Ideally, the HIP should not be able to penetrate virtual environment objects.

FIGS. 1A-1C depict a scenario 100 that illustrates a prior art technique of utilizing proxy 130 to control interactions between HIP 110 and polygon 120 in a virtual environment. In scenario 100, HIP 110 starts as the position shown as HIP 110a in FIG. 1A, moves through position HIP 110b shown in FIG. 1B, and ends at position HIP 110c shown in FIG. 1C. In this technique, HIP 110 and proxy 130 are connected by a simulated spring not shown in the Figures.

In FIG. 1A, proxy 130, shown at position 130a, is in "free motion"; e.g., proxy 130a is not touching polygon 120. In FIG. 1B, proxy 130, shown at position 130b, is "in contact" with polygon 120. In scenario 100, while HIP 110 continues to move down from position 110b into polygon 120, proxy 130 is not permitted to enter into polygon 120. In FIG. 1C, proxy 130, shown at position 130c, is still in contact with a surface of polygon 120 after HIP 110 has moved to position 110c inside of polygon 120. As the distance increases between HIP 110 and proxy 130, the simulated spring exerts a proportionally larger force to draw HIP 110 closer to proxy 130. FIG. 1C shows the simulated spring force as force 140 exerted on HIP 110. As shown in FIG. 1C, force 140 is exerted in the direction of a normal of the surface in contact with the proxy 130; e.g., a hypotenuse 122 of polygon 120.

FIG. 2 shows an example coordinate system 200 specifying six degrees of freedom for tool 210. Coordinate system 200 can be used for other entities as well, such as HIP. A position of tool 210 can be specified as a point (x, y, z) in three-dimensional space specified using coordinate system 200. For example, the point can defined in terms of three axes, such as an X axis, a Y axis, and a Z axis. Then, the position of tool 210 can be specified as a (x, y, z) coordinate, with x, y, and z respectively specifying an X-axis coordinate, a Y-axis coordinate, and a Z-axis coordinate. If only position is taken into account, tool 210 can be said to have three positional degrees of freedom, as each of x, y, and z can be specified to position tool 210.

Tool 210 can be rotated about each of the X axis, Y axis, and Z axis, as shown in FIG. 2. If only rotations are taken into account, tool 210 can be said to have three rotational degrees of freedom, as rotations about each of x, y, and z can be specified to rotate (or orient) tool 210. Taking both positional and rotational degrees of freedom into account, tool 210 can have up to 6 degrees of freedom, as listed on FIG. 2. These six degrees of freedom include respective degrees of freedom for selecting an X coordinate, a Y coordinate, a Z coordinate, an X rotation, a Y rotation, and a Z rotation.

Techniques for six degree-of-freedom haptic rendering in virtual environments consisting of polygons and/or voxels (volume pixels) have been specified. These efforts are typically divided into direct rendering- and virtual coupling methods where the latter can further be subdivided into penalty-, impulse- and constraint-based methods. The simplest 6-DOF haptic rendering method is the direct method, where the virtual tool perfectly matches the configuration of the haptic rendering device. The force sent to user is directly based on the amount of penetration in the virtual environment. Unfortunately the direct method suffers from problems with "pop through". Pop through is an artifact that arises when the rendering algorithm erroneously penetrates a thin surface.

In virtual coupling methods, a virtual coupling, or connection, between the haptic rendering device and the virtual tool is utilized. In this method, the force on the haptic rendering device is simply calculated as a spring between the virtual tool, referred to also as 'god-object', 'proxy' or 'IHIP', and the configuration of the haptic rendering device. 6-DOF rendering methods using virtual couplings rely on rigid body simulations, since the virtual tool has to be simulated as a 6-DOF object, as compared to 3-DOF rendering where the rotational component can be ignored. In penalty-based methods, the configuration (position and rotation) of the virtual tool is calculated using penalty forces based on the tool's penetration depth into objects, similar to how penalty-costs are used in traditional optimization. These penalty forces are then integrated to produce the motion of the virtual tool. This method results in a virtual tool that actually penetrates objects in the environment. Fortunately this penetration is typically very small.

For impulse-based dynamics methods, a virtual object is moved by a series of impulses upon contact/collision (rather than forces based on penetration depth). In constraint-based methods, the virtual tool moves into contact with the environment but (ideally) never violates constraints imposed by the environment.

Other environments can be explored by robots, such as undersea, outer space, and hazardous environments. In some of these environments, robots can be controlled by human operators receiving video and/or audio information from the robot.

SUMMARY

In one aspect, a method is provided. A computing device receives first depth data about an environment. The computing device generates a first plurality of points from the first depth data. The computing device determines a virtual tool, where the virtual tool is specified in terms of a translation component for the virtual tool and a rotation component for the virtual tool. The computing device determines a first force vector between the virtual tool and the first plurality of points. The computing device sends a first indication of haptic feedback based on the first force vector.

In another aspect, an article of manufacture is provided. The article of manufacture includes a physical and/or non-transitory computer-readable storage medium storing instructions that, upon execution by a processor of a computing device, cause the computing device to perform functions including: receiving first depth data about an environment; generating a first plurality of points from the first depth data; determining a virtual tool specified in terms of a translation component for the virtual tool and a rotation component for the virtual tool; determining a first force vector between the virtual tool and the first plurality of points; and sending a first indication of haptic feedback based on the first force vector.

In yet another aspect, a computing device is provided. The computing device includes a processor and data storage. The data storage stores instructions that, upon execution by the processor, cause the computing device to perform functions including: receiving first depth data about an environment; generating a first plurality of points from the first depth data; determining a virtual tool specified in terms of a translation component for the virtual tool and a rotation component for the virtual tool; determining a first force vector between the virtual tool and the first plurality of points; and sending a first indication of haptic feedback based on the first force vector.

In one aspect, a method is provided. A computing device receives first depth data about an environment. The computing device generates a first plurality of points from the first depth data. The computing device determines a haptic interface point (HIP). The computing device defines a virtual fixture for the environment. The computing device determines a first force vector between the HIP and the first plurality of points. The first force vector is based on the virtual fixture. The computing device sends a first indication of haptic feedback based on the first force vector.

In another aspect, an article of manufacture is provided. The article of manufacture includes a physical computer-readable storage medium. The physical computer-readable storage medium stores instructions that, upon execution by a processor of the article of manufacture, cause the article of manufacture to perform functions. The functions include: receiving first depth data about an environment; generating a first plurality of points from the first depth data; determining a HIP; defining a virtual fixture for the environment; determining a first force vector between the HIP and the first plurality of points, where the first force vector is based on the virtual fixture; and sending a first indication of haptic feedback based on the first force vector.

In yet another aspect, a computing device is provided. The computing device includes a processor and data storage. The data storage stores instructions that, upon execution by the processor, cause the computing device to perform functions. The functions include: receiving first depth data about an environment; generating a first plurality of points from the first depth data; determining a HIP; defining a virtual fixture for the environment; determining a first force vector between the HIP and the first plurality of points, where the first force vector is based on the virtual fixture; and sending a first indication of haptic feedback based on the first force vector.

In one aspect, a device configured for operation in an underwater environment is provided. The device includes a camera. The camera is configured to capture, within a predetermined interval of time, first light within a first frequency range of light in the underwater environment and second light within a second frequency range of light in the underwater environment. The camera is configured to generate a first image based on the first light and a second image based on the second light, where the first frequency range of light differs from the second frequency range of light. The camera includes a communication interface. The communication interface is configured at least to send at least the first image and the second image and to receive one or more commands based on haptic feedback with the haptic feedback generated based on the first image and the second image.

In another aspect, a method is provided. A camera captures, within a predetermined interval of time, first light within a first frequency range of light in an underwater environment and second light within a second frequency range of light in the underwater environment. The camera generates a first image based on the first light and a second image based on the second light. The first frequency range of light differs from the second frequency range of light. The camera sends at least the first image and the second image from the camera One advantage of this application is the ability to specify and providing haptic feedback for application using a virtual tool specified using six degrees of freedom interacting with objects in an environment specified using point data with depth information, such data for a plurality of points. For example, three degrees of freedom can specify a position of the virtual tool in a three-dimensional space, and three degrees of freedom can specify an orientation, or rotation, of the virtual tool with respect to the three-dimensional space. An example application for using the virtual tool is a task performed by a user-controlled robot, where haptic feedback is given to the user during remote control of the robot.

Another advantage of this application is that haptic feedback is generated at rapid rates based on depth data, such as a stream of frames with depth information. As disclosed herein, the use of a stream of frames with depth information permits haptic rendering, or providing haptic feedback, at a haptic rendering rate faster than a frame-reception rate. In some embodiments, a herein-described haptic rendering system can have a haptic rendering rate of at least 1000 Hz.

Another advantage of this application is that virtual fixtures can be defined based on objects recognized in the environment. That is, as an object changes within the environment, a virtual fixture associated with the object can dynamically adjust to the changes of the object. Another advantage is that virtual fixtures can be dynamically changed based on status of operations, such tasks listed and organized on a task list. One or more virtual fixtures can be associated with task(s) on the task list. Virtual fixtures associated with a task can change based on the status of the task. Thus, the virtual fixtures can change throughout execution of a task, and so guide completion of the task. Further, a level of automation can be specified that controls the virtual fixtures, and so allows for full automation, partial automation, or no automation (manual control) for completing the task.

Another advantage of this application is providing a camera that captures images and depth information underwater. The images can be captured in one range of frequencies, such as within a blue-green range of visible light frequencies. The depth information can be captured in a different range of frequencies, such as in a near-infrared range of frequencies. The visible light can be captured and a visible light image generated. At the same time, NIR radiation can be captured and an image with depth information generated. The visible light image and the image with depth information can be sent from the camera in succession, so that both visible-light information and depth information for a same time can be provided. The visible-light information and depth information can be used to generate haptic feedback for operators controlling devices to perform underwater tasks.

Providing haptic feedback from underwater sensors to an operator at the surface has the potential to transform subsea manipulation capability. Virtual fixtures will allow manipulators to precisely maneuver in sensitive environments where contact should not be made with surrounding objects or structures. Biological studies of animal colonies around hydrothermal vents could benefit greatly from such a capability—allowing scientists to carefully gather data with unprecedented resolution and proximity to sensitive organisms. Common tasks such as connector mating between instruments can be carried out very efficiently by creating guidance fixture near male and female connectors. Thus, time, expense, and equipment can be saved, and the environment preserved using the herein-described haptic feedback techniques to perform underwater tasks.

BRIEF DESCRIPTION OF THE DRAWINGS

Various examples of particular embodiments are described herein with reference to the following drawings, wherein like numerals denote like entities, in which:

FIG. 27A is an image of example metal objects, in accordance with an example embodiment;

FIG. 27B is a graph of an output signal from an interferometer-based metal detector while scanning for metal objects, in accordance with an example embodiment;

FIG. 27C is an outline of metal objects determined based on the data in FIG. 27B, in accordance with an example embodiment;

DETAILED DESCRIPTION

Overview

Figure 1A:
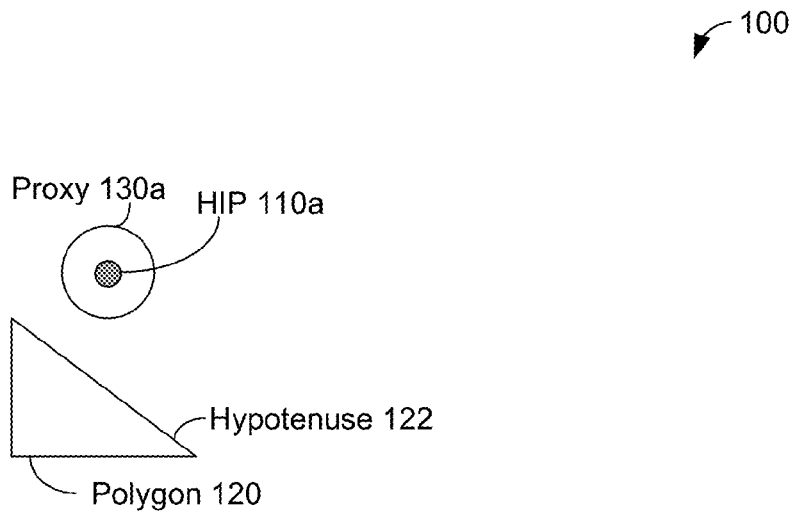
FIGS. 1A-1C depict a scenario illustrating a prior art technique of controlling interactions between a Haptic Interaction Point (HIP) and a polygon in a virtual environment.
Figure 1B:
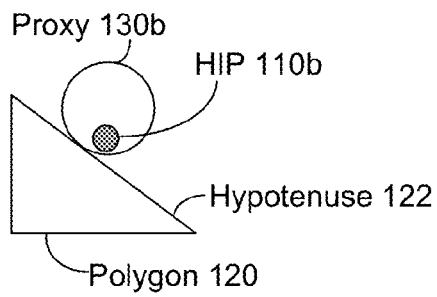
Figure 1C:
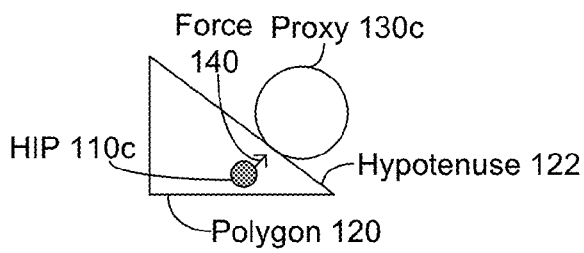

Haptic interaction has traditionally been a purely virtual task. But recent advancements in depth sensing have made it possible to stream point data with depth information in real-time and at low cost; e.g., by using a depth-enabled camera such as the camera used by Kinect from the Microsoft Corporation of Redmond, Wash. For example, haptic interaction with 6-DOFs from streaming point data can enable applications that fully utilize a 6-DOF haptic rendering device, such as the 'delta.6' haptic interface from Force Dimension of Nyon, Switzerland. A 6-DOF haptic rendering method could be useful even though many haptic rendering devices only support 3-DOF actuation (but has 6-DOF sensing), such as the PHANTOM Omni® haptic rendering device from Sensable Inc. of Wilmington, Mass.

Example 6-DOF applications include situations for remotely touching a moving object, such as remotely petting a dog. For example, the depth-enabled camera can capture depth images of a remote environment where the dog is located. The depth images can be transmitted to a local computing device. The local computing device can generate a virtual three-dimensional environment showing the depth images (in this example, representing the dog) along with a virtual tool. The virtual tool can be controlled by a local user of the haptic rendering device connected to the local computing device during interaction with the virtual environment. For example, the virtual tool can represent a 6-DOF haptic rendering device controlled by the local user and the virtual tool can take the form of a virtual human hand in the virtual environment. The user can control the 6-DOF haptic rendering device to provide commands to move the virtual tool; e.g., move the virtual human hand to pet the dog. In response, a robot located in the remote environment can receive equivalent commands to those provided to the virtual tool; e.g., so that the robot can move and pet the dog.

When haptic interaction is combined with manual control of a robot (or robotic end effector) in co-robotic tasks, such as telerobotic surgery, a 6-DOF capability could add versatility and precision to this co-robotic interaction. For example, it has also recently been shown that the techniques of haptic rendering with 3 DOFs can be useful in telerobotics for implementation of virtual fixtures. That is, the user receives a force when the teleoperated robot is near collision with the environment.

In some embodiments, virtual fixtures related to point data can be specified. Examples of virtual fixtures include forbidden-region fixtures and guidance fixtures. A forbidden-region fixture can define an area represented by the point data where the virtual tool is not permitted to enter; i.e., the forbidden region. A guidance fixture can define an area represented by the point data where the virtual tool is permitted, and perhaps encouraged, to enter. Haptic feedback can be provided once the virtual tool attempts entry of a virtual fixture.

Another example use of haptic feedback is robotic or telerobotic surgery. In telerobotic surgery, a surgeon can be located at one location which can be remote from an operating room that holds the patient. During the operation, the surgeon can view the patient using depth images provided by a depth-enabled camera in the operating room and transmitted to a local computing device. The local computing device can receive the depth images, generate a virtual environment for the surgeon, receive commands via a 6 DOF haptic rendering device to control a virtual tool and corresponding surgical robot in the operating room, and generate haptic feedback that the surgeon can use to better treat the patient.

Haptic feedback can also be useful in remotely controlling exploration devices operating in hostile, dangerous, and/or unsafe environments. Example exploration devices include undersea and outer space exploration vehicles, explosive location devices, chemical sniffing (e.g., drugs, gas leaks, toxic waste) mechanisms, exploration robots, and/or other exploration devices. For example, using haptic feedback, including haptic feedback in forbidden regions, can provide additional information about an environment under exploration and/or protect the exploration device from entering a known dangerous, already-explored, or otherwise forbidden region.

Example Environments for Haptic Rendering

Figure 3A:
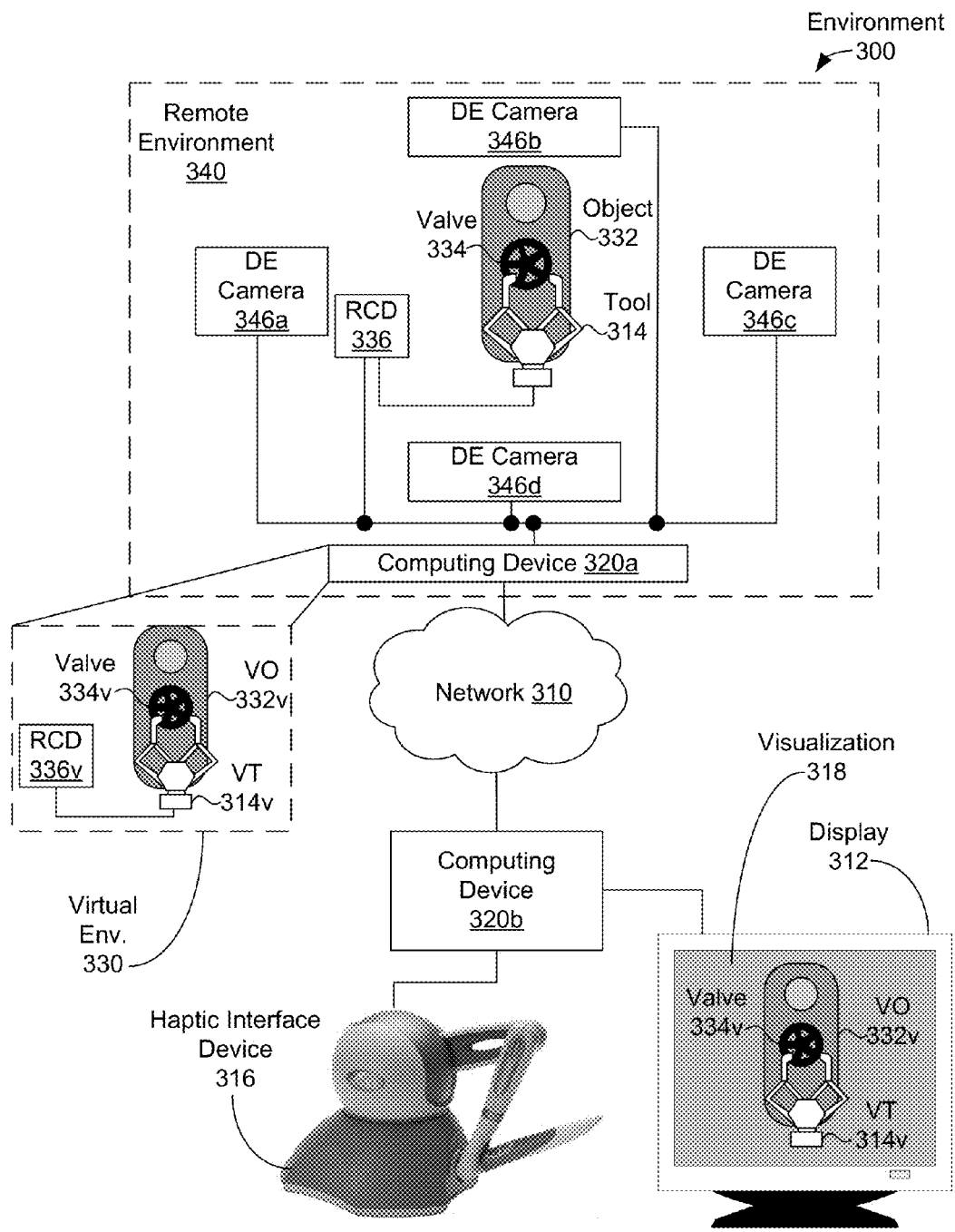
FIG. 3A is a diagram of a haptic rendering environment, in accordance with an example embodiment.

FIG. 3A is a diagram of a haptic rendering environment 300, in accordance with an example embodiment. Environment 300 includes computing devices 320a, 320b connected via network 310. Computing device 320a is in remote environment 340 and is additionally connected to remote controlled device (RCD) 336, and depth-enabled (DE) cameras 346a-346d. Remote controlled device 336 is connected to tool 314. Computing device 320b is additionally connected to display 312 and haptic feedback device 316.

In the example shown in FIG. 3A, each of depth-enabled cameras 346a-346d is configured to capture depth data of remote controlled device 336 and objects 342, 344 and provide the captured depth data to computing device 320a. One example of depth data is a depth image having observed color and depth values. In some embodiments, each of depth-enabled cameras 346a-346d can be configured with an optical camera to capture image data and an infrared camera to capture depth data.

The depth image can be received as a NR×NC matrix of pixels, with each pixel having 24 RGB bits of color value information, including 8 bits of data for each of red, green and blue component colors. The depth values can be received as a NR×NC matrix, where each depth value has $B_d$ bits. For one example depth-enabled camera, the Kinect camera uses NR=640, NC=480, and $B_d$=11 or 13, and so produces 640×480 matrices of image data and depth data, where each depth value has at least 11 bits. The Kinect camera can simultaneously provide both image and depth data at a frame rate $f_c$ of 30 Hz. The depth values can represent depth relative to the camera ranging from Dmin to Dmax, with Dmin representing a minimum distance from the camera, e.g., 0 mm; and Dmax, e.g., 2048 or 8192 mm. Color and/or depth values can have additional information, such as device information about the camera capturing the depth image.

In some embodiments, computing device 320a can be connected to more or fewer depth-enabled cameras than shown in FIG. 3A, while remaining connected to at least one depth-enabled camera. In other embodiments, a depth-enabled camera can generate other types of depth data than depth images; e.g., depth-only information, point clouds. In yet other embodiments, devices other than depth-enabled cameras can provide depth data; e.g., depth sensors using radar or another technique to determine depth.

Figure 2:
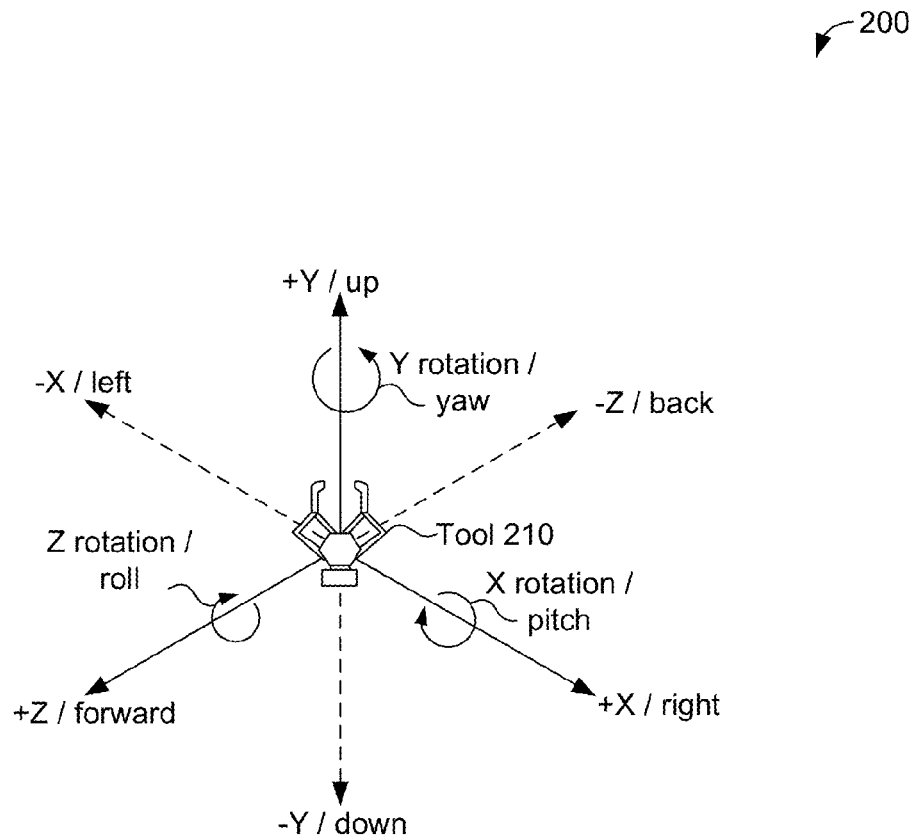
FIG. 2 shows an example coordinate system specifying six degrees of freedom for a tool.

Computing device 320a can use received depth data to generate virtual environment 330. In order to interpret the depth data, computing device 320a can transform the depth data into a collection of points, each point specified in a Cartesian coordinate system in three dimensions; e.g., as an (x, y, z) point in coordinate system 200 discussed above in the context of FIG. 2.

Each (x, y, z) point from the depth data can represent one point in a "point cloud" or collection of points in three-dimensional Cartesian space; e.g., $(x, y, z) \in \mathbb{R}^3$. In other embodiments, other data structures than point clouds or other collections of points can be generated from depth data. After generating the collection of points, computing device 320a can render virtual environment 330 as images and/or as a three dimensional visualization. FIG. 3A shows virtual environment 330 including virtual objects (VOs) 332v, virtual valve 334v, virtual remote controlled device 336v, and a representative virtual tool 314v.

Computing device 320a and remote environment 340 can be physically distant from computing device 320b. In some scenarios, remote environment 340 can be physically near or in the same environment as an environment around computing device 320b. In particular, of these scenarios not shown in the Figures, one computing device can provide the herein-described functionality of computing devices 320a and 320b.

Computing device 320a can generate force vectors related to tool 314 and send indications of haptic feedback to computing device 320b. Upon reception of the indications of haptic feedback, computing device 320b can utilize haptic interface device 316 to generate the haptic feedback. Additionally, computing device 320a and/or 320b can generate visualization 318 with virtual object 332v, virtual valve 334v, and/or virtual tool 314v. As also shown in FIG. 3A, visualization 318 can include an indication of virtual tool 314v which can correspond to virtual tool 314v in virtual environment 330 and/or tool 314 in remote environment 340.

Haptic interface device 316 can be a controllable mechanism configured to receive indications of haptic feedback and provide the indicated haptic feedback based on the indications. Example haptic interface devices 316 include, but are not limited to a delta.6 haptic interface from Force Dimension, a PHANTOM Omni® Haptic Device from Sensable Inc., other haptic devices, other haptic interfaces, haptic gloves, tactile displays, devices configured at least in part to provide haptic feedback such as laptop computers, desktop computers, mobile telephones, haptic suits, and/or other devices.

As haptic interface device 316 is moved, indication(s) of movement of haptic interface device 316 can be generated and sent from computing device 320b, such as to computing device 320a via network 310. Upon reception of the indication(s) of movement, computing device 320a can update a position of virtual tool 314v. Also or instead, computing device 320a can send control signals to change movement and/or rotation; e.g., change speed, direction, acceleration, pitch, yaw, roll, or to stop) to remote controlled device 336 to move tool 314 accordingly. In other embodiments, virtual tool 314v can represent a position of tool(s), sensor(s), and/or other device(s) on remote controlled device 336 other than tool 314, and by sending control signals remote controlled device 336, the tool(s), sensor(s), and/or other device(s) can be moved.

As depth data of remote environment 340 are captured, the captured depth data can correspond to images and points showing movement and/or rotation of remote controlled device 336 and/or tool 314 and thus showing movement and/or rotation of virtual tool 314v. In some embodiments, remote controlled device 336v and/or virtual tool 314v can be moved within virtual environment 330 based on the indication(s) of movement/rotation instead of or as well as based on captured image and depth data.

An Algorithm for Moving a 6-DOF Virtual Tool

An algorithm is described for haptic interaction, which can be classified as a constraint-based virtual coupling method. The haptic interaction algorithm can support real-time haptic interaction with discontinuous streaming point data derived from depth sensors by iteratively resolving collisions for each received set of streaming point data; e.g., a received depth image.

The haptic interaction can occur between an arbitrary voxelized virtual tool controlled by a haptic rendering device and an environment represented using streaming point data with depth information derived from a depth sensor. A user of a haptic interface can direct a virtual tool to interact with both static point data for real objects and dynamic point data captured in real-time. The haptic interaction method can provide realistic forces/force feedback for a six degree-of-freedom haptic interaction by performing a rigid body simulation of the virtual tool at a very high rate; in some embodiments, a haptic rendering rate of at least 1000 Hz can be supported.

The point data can be represented by one or more depth images representing a set of fixed and infinitely stiff points in space. Each depth image can be filtered and surface normals for objects represented as points in the depth image can be calculated in real-time. Direct interaction between the virtual tool and the point data can be performed without first converting the point data to an intermediate data structure to speed rendering.

A quasi-static (at rest) simulation can enable matching of the position and orientation between the haptic rendering device and the virtual tool; i.e., a 6 DOF configuration. Collision between the virtual tool and the virtual environment can be detected. In the virtual environment, the virtual tool can be in one of the following three states: free motion, in contact, or in collision. The free-motion state occurs when no points based on depth information about the environment constrain the virtual tool. The in-contact state occurs when there are points based on depth information about the environment on the boundary of, but not penetrating, the virtual tool. The in-collision state occurs when there are points based on depth information about the environment that penetrate the virtual tool.

The quasi-static simulation can involve moving the virtual tool at each of a number of time steps to enable the virtual tool to contact and then bounce off a surface represented contact point(s) in the point data. The virtual tool is be simulated as an object at rest at the beginning of a time step. Then, the state of the virtual tool can be determined. If the virtual tool does not collide with points in the environment, then the virtual tool is in free motion; e.g., the virtual tool is in the free-motion state. If a collision is detected between points in the environment and the virtual tool, then the virtual tool can either be in contact; e.g., the virtual tool is in the in-contact state, or the virtual tool can be in collision; e.g., the virtual tool is in the in-collision state.

When the virtual tool is in contact, the points in the environment in contact with the virtual tool can form motion constraints for the virtual tool. These constraints can be used to compute a constrained motion that will move the virtual tool towards the configuration of the haptic rendering device without violating any contact constraints. When the virtual tool is in collision, the collision can be resolved by moving the virtual tool away from the set of collision constraints.

Periodically or otherwise, new information about the virtual environment can be received. For example, when a new depth data, such as a depth image, depth frame, or other data including depth information is captured, the new depth data can be transformed into a point cloud or other structure representing points in the environment, where every point in Cartesian space corresponds to a pixel. The point cloud can be filtered; e.g., using a bilateral filter and a surface normal is calculated for every point in the filtered point cloud. This surface normal calculation can lead to collision constraint(s) that point in the correct direction for a surface, regardless of which direction is used to approach the surface. After the state of the virtual tool is determined, the force on the haptic rendering device is calculated as a function of the kinetic distance between the configuration of the virtual tool and the haptic rendering device.

Table 1 below includes example pseudo-code describing an example haptic interaction algorithm regarding moving a virtual tool in a virtual environment.

TABLE 1

```
0001  done = false;
0002  WHILE (done == FALSE) DO
0003    // process depth data Din - see "Real-Time Processing of Streaming Depth Data" section.
0004    IF (new depth data available) THEN
0005      Receive depth data Din from capture device, with Din including depth information for
0006        each of a number of pixels captured by captured device
0007      FOR each pixel P in Din DO
0008        Let Coords(P) = Cartesian coordinates for P;
0009        Filter depth values of P;
0010        Let Normal(P) = normal vector for point P pointed toward capture device;
0011      END FOR
0012    END IF
0013
0014    // determine motion constraints - see "Collision Detection with the Virtual Tool" section
0015    // assume no points of Pin are in contact with VT
0016    Let VOX = voxelization of virtual tool VT;
0017    Let BB = bounding box of projection of VT onto Din;
0018    Let state = free-motion;
0019    Let points_of_contact = NULL;
0020    render_virtual_environment(Din, VT); // render the virtual environment with VT
0021
0022    // now, find out if any points are in contact with VT
0023    // if point is within bounding box, then see if pixel corresponds to point within
0024    // voxelization VOX of VT. If point in VOX, then point is in contact or collides with VT
0025
0026    FOR each pixel P in Din DO
0027      IF (Coords(P) is within BB) THEN
0028        Let P' = conversion of Coords(P) into coordinates used for VOX;
0029        Query VOX to determine if P' is a point within boundary of VOX;
0030        IF (P' is within boundary of VOX) THEN
0031          Add P to points_of_contact;
0032        END IF
0033      END IF
0034    END FOR
0035
0036    // if there are any points in contact, see if any points penetrate VT. If point penetrates VT,
0037    // then point is in collision with VT. Otherwise, VT is in-contact (just touching) the point.
0038
0039    IF (points_of_contact != NULL) THEN
0040      Let state = in-contact
0041      FOR each point PC in points_of_contact DO
0042        IF (penetration depth of PC into VT > 0) THEN
0043          Let state = in-collision
0044        END IF
0045      END FOR
0046    END IF
0047
0048    // move VT based on state -- see "Finding a Constrained Motion while In Contact"
0049    // and "Resolving Collisions" sections below
0050
```

TABLE 1-continued

```
0051    initialize_matrix(Matrix_J); // create/zero out Matrix_J as necessary
0052
0053    IF (state ==free-motion) THEN // no constraints on moving VT
0054       Move VT according to unconstrained acceleration of Equation (1) below
0055    ELSE
0056       // points in contact/collision add constraints
0057       FOR each point PC in points_of_contact DO
0058          Determine constraint(PC) using Equation (2) below
0059          Add constraint(PC) to Matrix_J;
0060       END FOR
0061
0062       // move VT based on state and constraints
0063       IF (state == in-contact) THEN
0064          Move VT according to constrained acceleration (see Equations (3) and (4))
0065          using nearest point algorithm;
0066       ELSE // state == in-collision
0067          Move VT according to constrained acceleration using Equations (6) and (7)
0068       END IF
0069    END IF
0070
0071    // apply force to haptic rendering device - see "Calculating the Force" section
0072    Let F = force determined by Equation (8)
0073    Send indication of F to provide haptic feedback
0074
0075    // determine if we can terminate algorithm
0076    done = are_we_done_yet( ); // or similar technique/function
0077 END WHILE
```

The algorithm shown in Table 1 is specified as mainly as a loop between lines 0002 and 0077 that can iterate one or more times until a variable done is TRUE. A loop iteration can begin at line 0005 by determining if new depth data Din is available. If so, the new depth data D in is processed at lines 0006-0013, and as further discussed in the "Real-Time Processing of Streaming Depth Data" section below.

As further discussed in "Collision Detection with the Virtual Tool" section below, lines 0014-0020 involve generating a voxelization VOX of a virtual tool VT and a bounding box BB of a projection of virtual tool VT into a space for D in, as well as initialing a state variable, representing a state of VT, to "free-motion" and a points of contact list to NULL (no points in list). Also, the virtual environment is rendered based on depth data D in and virtual tool VT. At lines 0021-0034, a determination is made whether any points represented by the depth data D in are in contact with virtual tool VT. At lines 0035-0046, the state of VT is determined: (a) if no points of Din are in contact with VT, the state of VT remains set as "free-motion", (b) if a point of DIN is in contact with VT and if none of the in-contact points in the points of contact list has penetrated VT, the state of VT is set to "in-contact", (c) else, at least one point has penetrated VT and so the state of VT is set to "in-collision".

At lines 0047-0069, virtual tool VT is then moved based on VT's state, which is discussed below in the "Finding a Constrained Motion while In Contact" and "Resolving Collisions" sections below. If VT is in a state of free-motion (VT is not in contact with any points of Din and no interpenetrations), the movement is based on unconstrained acceleration specified using Equation (1) below. That is, the virtual tool can be moved in the direction of the unconstrained acceleration until first contact occurs. In some embodiments, the virtual tool can be moved in small discrete steps to ensure that no contact is missed.

Otherwise, VT is moved according to constrained acceleration specified using Equations (2)-(7) below. In some embodiments not shown in Table 1 above, bisection can be applied at first contact to further refine the point(s) of contact. In other embodiments not shown in Table 1 above, the constrained acceleration can be applied in small discrete steps, where the magnitude per step is limited to a predetermined amount. The virtual tool can be moved in small discrete steps such that no feature is missed (as for the case when the virtual tool is in free motion). This procedure of movement using small discrete steps can be repeated until collision is resolved. In particular of these embodiments, bisection can be applied again until the collision is resolved.

At lines 0070-0073, force feedback is calculated and provided to a user of a haptic tool operating VT, discussed below in the "Calculating the Force" section. At the end of the loop iteration on lines 0074-0077, a determination is made as to whether the algorithm should end or not. If the algorithm should end, the done variable should be set to TRUE to terminate the loop, and therefore the algorithm. Otherwise, done should be set to FALSE to lead to another loop iteration.

Real-Time Processing of Streaming Depth Data

Figure 3B:
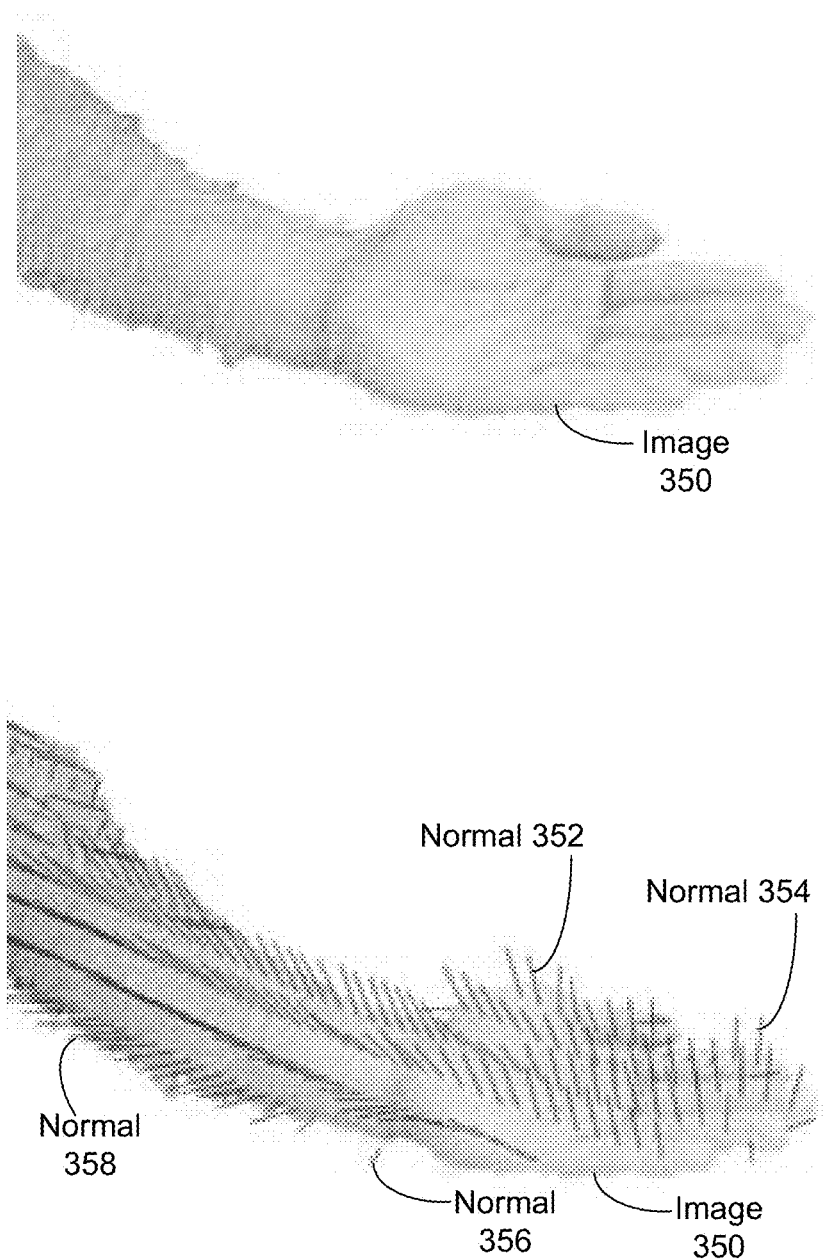
FIG. 3B shows an image based on captured depth data and the same image annotated with normal vectors, in accordance with an example embodiment.

FIG. 3B shows depth image 350 based on captured depth data and depth image 350 annotated with normal vectors including normals 352, 354, 356, 358, in accordance with an example embodiment. The upper image of FIG. 3B shows depth image 350 of captured depth data representing a human hand and arm.

As mentioned above, Cartesian coordinates can be determined for each pixel in a depth image. For each pixel, color and depth values in the depth image can be used to calculate Cartesian coordinates for a corresponding point. With the pixels in the depth image transformed to points in a Cartesian coordinate system, the depth values can be filtered using a bilateral filter, where the points can be weighted using a Gaussian kernel as a function of Euclidean distances in a Cartesian frame. The points can be weighted to preserve depth discontinuities; i.e., a neighboring pixel only contributes to the filtered value if its depth value is sufficiently close.

A normal vector can be calculated by fitting a plane to the points in a small neighborhood around each point using a least squares technique. The neighboring points can be weighted using the smooth Wendland weighting function (e.g., with radius rw). This weighted total least squares problem has a closed form solution that can be solved with a 3×3 eigenvalue decomposition for every point. There can be two numerical solutions to the least squares problem, where each solution is a possible normal. The normal can be selected as the numerical solution pointing towards the depth sensor.

The lower image shown in FIG. 3B shows depth image 350 annotated by normal vectors; e.g., normals 352, 354, 356, 358, where the normal vectors were calculated using the techniques discussed immediately above for each $1000^{th}$ point derived from depth image 350. In some embodiments, a normal vector can be calculated for every point in a depth image. In other embodiments, per-pixel data parallel work can be performed by a computing device utilizing one or more graphics processing units (GPUs). For example, the above-mentioned Cartesian transformation, bilateral filtering, and/or least squares solution/eigenvalue decomposition can be done for every pixel in parallel using OpenCL (Khronos Group Inc.) running on the GPU(s).

GPU performance can be optimized by copying several pixels at a time to local GPU memory. Then, the copied pixels can be processed in parallel by a work group of computational units; i.e., components of GPUs and/or entire GPUs. As local memory access by the computation units can be up to 2 orders of magnitude faster than remote memory access, performance can be significantly speeded by use of local GPU memory. Local copying can be useful in filtering operations where many neighboring pixels are accessed.

Collision Detection with the Virtual Tool

In order for the virtual tool to move with respect to the points derived from the depth image, a quick collision detection method is needed. In some embodiments, the virtual tool is voxelized. For example, the voxels can be of a uniform size, such as 0.5 mm on a voxel side. Voxels can be stored in local memory using a simple scan-line technique.

To determine whether a point P collides with a virtual tool VT, the point P can be transformed to a corresponding point P' in a frame of reference for VT. Then, point P' can be queried against the voxels used to voxelize VT. In some cases, the query can be equivalent to a look up in a collision/no collision lookup table. In some embodiments, collision lookup can be sped by checking for collision with points that are in the neighborhood of virtual tool VT. The neighborhood of VT can be approximated using a two-dimensional bounding box placed around the projection of the virtual tool onto the depth image. Then, a point Pn can be determined to be within the neighborhood of VT if a corresponding pixel Px to point Pn is a pixel within the bounding box projected on to the depth image.

Figure 4A:
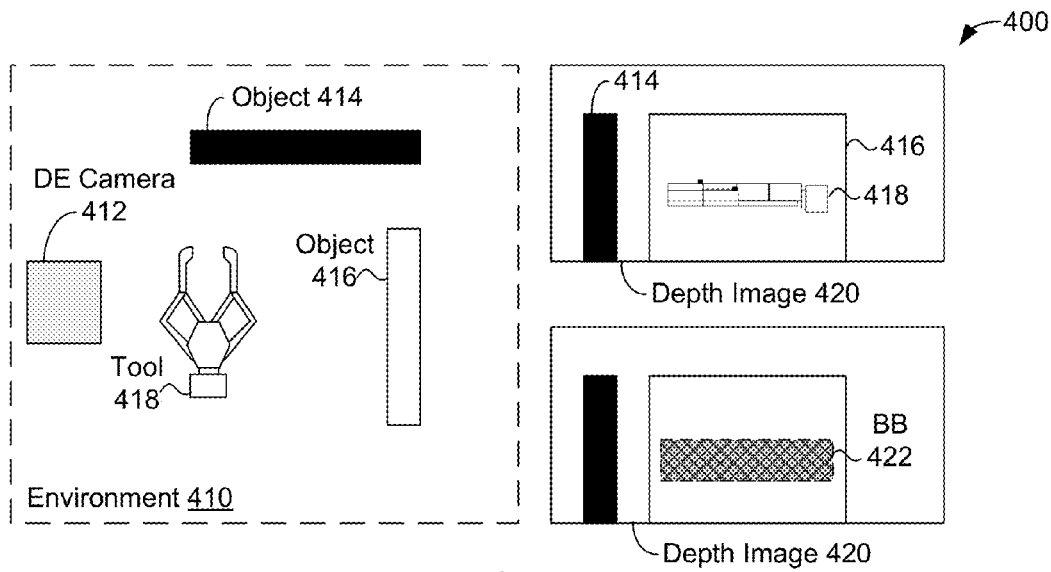
FIG. 4A depicts a scenario of capturing depth data in an environment, in accordance with an example embodiment.

FIG. 4A depicts scenario 400 of capturing depth data in an environment 410, in accordance with an example embodiment. The left side of FIG. 4A shows an overhead view of environment 410, with depth enabled camera 412 configured to capture depth data, such as depth images, of objects 414 and 416 as well as tool 418. At a time T1 in scenario 400, tool 418 is in front of object 416 and to the left of object 414.

At time T1, depth enabled camera 412 captures depth image 420 of environment 410. Depth image 420 is shown in the upper-right portion of FIG. 4A, with object 414 on the left side of the image, object 416 in the central portion of depth image 420, and a side view of tool 418 shown in front of object 416. In scenario 400, after conversion of pixels in depth image 420 to corresponding points in a Cartesian coordinate system, each point is then checked for collision with a virtual tool representing tool 418.

As discussed above, a bounding box surrounding the image of tool 418 can projected on to depth image 420. The lower-right portion of FIG. 4A shows depth image 420 with projected bounding box 422 replacing a portion of depth image 420 depicting tool 418. Then, points corresponding to pixels of depth image 420 that are within bounding box 422 can be queried for possible collision with tool 418. In scenario 400, the corresponding points can be points captured from object 416, whose depth values would be larger than those of tool 418; i.e., object 416 is behind tool 418. As such, no collisions would be detected between tool 418 and points representing the rest of environment 410 in scenario 400.

Figure 4B:
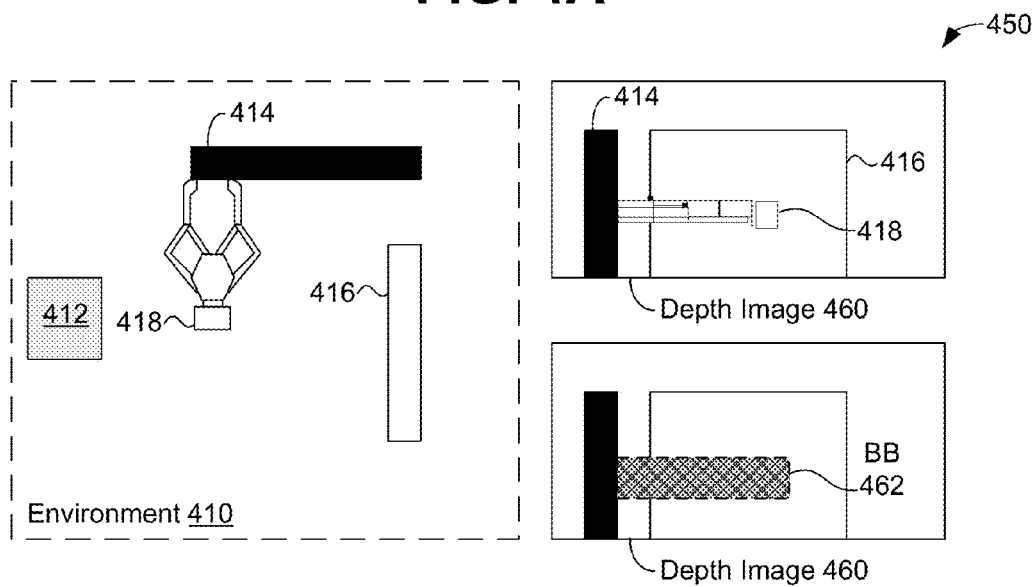
FIG. 4B depicts another scenario of capturing depth data in the environment shown in FIG. 4A, in accordance with an example embodiment.

FIG. 4B depicts scenario 450 of capturing depth data in an environment 410, in accordance with an example embodiment. The left side of FIG. 4B shows an overhead view of environment 410, with depth enabled camera 412, objects 414 and 416, and tool 418 as discussed above in the context of FIG. 4A. At a time T2 in scenario 400, tool 418 is in front of object 416 and just touching object 414.

At time T2, depth enabled camera 412 captures depth image 460 of environment 410. Depth image 460 is shown in the upper-right portion of FIG. 4B, with object 414 on the left side of the image, object 416 in the central portion of depth image 460, and a side view of tool 418 shown in front of object 416 and just touching object 414. In scenario 450, after conversion of pixels in depth image 460 to corresponding points in a Cartesian coordinate system, each point is then checked for collision with a virtual tool representing tool 418.

As discussed above, a bounding box surrounding the image of tool 418 can projected on to depth image 460. The lower-right portion of FIG. 4B shows depth image 460 with projected bounding box 462 replacing a portion of depth image 460 depicting tool 418. Then, points corresponding to pixels of depth image 460 that are within bounding box 462 can be queried for possible collision with tool 418. In scenario 450, some of the corresponding points can be points captured from object 416 as discussed above in the context of FIG. 4A. Other of the corresponding points can be points from object 414, such as points at the left-most extent of bounding box 462 that just touches object 414. The depth values can be similar to those depth values representing a position of tool 418; i.e., object 414 may be in contact with and/or penetrated by tool 418. As such, collisions may be detected between object 414 and tool 418 in scenario 450.

Finding a Constrained Motion while in Contact

Using this collision detection method, the virtual tool is moved towards the configuration of the haptic rendering device and stopped at the first point of contact. Gauss' least constraints principle can provide a basis for find a feasible movement for the virtual tool that will not violate the contact constraint further.

The generalized unconstrained acceleration $a_{gu}$ can be expressed using Equation (1) below:

$$a_{gu} = \begin{pmatrix} a_u \\ \alpha_u \end{pmatrix} \quad (1)$$

where $a_u$ is the unconstrained acceleration in the horizontal and vertical (X and Y) dimensions, and $a_u$ is the unconstrained acceleration in the depth (Z) dimension.

$a_{gu}$ can be considered as an ideal unit step; e.g., a unit step that can be taken if the configuration of virtual tool VT were to match the configuration of the haptic rendering device.

However if virtual tool VT is in contact, this ideal unit step cannot be taken. Each point of contact (as found by the collision detection) can introduce a linear constraint on accelerations a and α specified by Equation (2):

$$n^T a + (r \times n)^T \alpha \geq d \quad (2)$$

For equation (2), n is the normal vector at the point of contact, r is the vector from the center of mass to the point of contact, and d is the penetration depth of the point of contact with d=0 when virtual tool VT is in contact with, but not penetrated by, the contact point and d<0 when virtual tool VT is penetrated by the contact point.

Given $a_{gu}$, a constrained acceleration $a_c$ can be calculated which minimizes the kinetic distance between the virtual tool and the haptic rendering device with respect to the linearized constraints. More formally, the constrained acceleration $a_c$ can be found as $$a_c = \frac{1}{2} \min_{a_g} (a_{gu} - a_g)^T M (a_{gu} - a_g) \quad (3)$$

subject to $$J a_g \geq 0 \quad (4)$$

where M is the mass matrix for the virtual tool and J is a matrix of constraints formed by (2) for each point in contact.

Equations (3) and (4) represent a quadratic programming problem solvable using Wilhelmsen's nearest point algorithm. The constrained acceleration $a_c$ may be valid for only a small neighborhood around the current configuration because of the linearized contact constraints J. Further, validity of $a_c$ can be affected any movement by the virtual tool VT and/or changes in point positions introduced by new depth data (represented by Pin), as the movement can introduce new constraints on virtual tool VT.

Figure 4C:
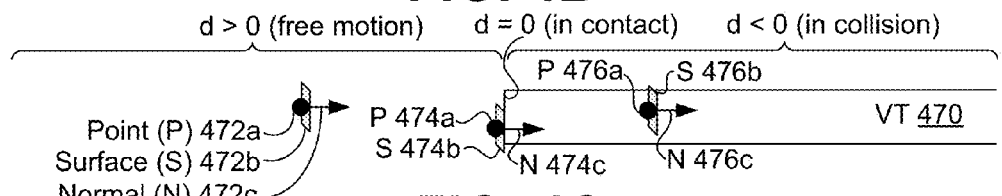
FIG. 4C depicts a virtual tool and example points of depth data captured from an environment, in accordance with an example embodiment.

To illustrate the depth value d of Equation (2), FIG. 4C depicts virtual tool 470 and example points (Ps) 472a, 474a, and 476a representing depth data captured from an environment. For example, points 472a, 474a, and 476a can be points in a Cartesian coordinate system calculated from pixels of a depth image, as discussed above. As mentioned above, a normal vector can be calculated by fitting a plane, or surface, to each of points 472a, 474a, and 476a a small neighborhood around each point. For example, FIG. 4C shows an example surface (S) 472b calculated for point 472a and corresponding normal (N) 472c. FIG. 4C also shows surfaces 474b, 476b and normals 474c, 476c for respective points 474a, 476a.

The depth d for a point P with respect to virtual tool VT can be specified as a distance from P to a portion of VT closest to P along the direction of a normal vector N associated with P. For example, FIG. 4C shows that point 472a is a positive distance from a portion of virtual tool 470 closest to point 472a in the direction of normal 472c; that is, the depth of point 472a with respect to virtual tool 470 is positive. As the depth of point 472a is positive, virtual tool 470 can be classified as in free motion, or unconstrained by, point 472a.

As another example, FIG. 4C shows that point 474a is just touching a surface of virtual tool 470. That is, point 474a is a distance of 0 units away from virtual tool 470 in the direction of normal 474c, and so the depth of point 474a is 0. As the depth of point 474a is 0, virtual tool 470 can be classified as being in contact with point 474a. FIG. 4C also shows that point 476a is inside the surfaces of virtual tool 470. That is, point 476a is a negative distance away from a closest surface of virtual tool 470 in the direction of normal 476c, and so the depth of point 474c is negative. As the depth of point 476a is negative, virtual tool 470 can be classified as being in collision with point 476a. As such, virtual tool 470 can be considered to be constrained by points 474a and 476a.

Resolving Collisions

One technique to resolve collisions between VT and points is based on the use of interval arithmetic. Generally speaking, interval arithmetic operates on ranges (or intervals) of values rather than specific values. For example, suppose bodies A and B are 6.5 feet apart. For interval arithmetic, the relative position of A and B can be specified based on a distance interval; e.g., an interval between 6 to 8 feet.

As part of this collision-resolution technique, the step size to move any part of the virtual tool can be constrained to be less than the smallest size of voxels used to represent the virtual tool. For example, the step size can be chosen to be half the tool voxel size. Bounding the virtual tool movement can ensure that no collisions are missed in a single point image, or when static point data is used. However, when dynamic point data is used, bounding the virtual tool's movement does not hold after the point data updates, as the locations of points represented by a new point image or other representation of the point data can be arbitrary.

A quasi-static collision resolution technique can be used to resolving collisions between virtual tools and virtual environments represented by dynamic point data. Initially, virtual tool VT is at rest; e.g., satisfies the condition specified by Equation (5):

$$a_{gu} = 0 \quad (5)$$

To move the virtual tool VT, the depth value d (discussed above in the context of Equation (2) and below in the context of FIG. 4C) has to be non-zero in order for the minimization to move the virtual tool out of the constraint. The value of d should ideally match the penetration depth at each point of collision. However, a planar constraint specified in Equation (2) may only be valid in a small neighborhood of virtual tool VT and since movements of virtual tool VT might introduce new constraints.

An approximate solution to resolve collisions can be obtained by weighting the constraints equally and updating the configuration of the virtual tool iteratively. This approach can be summarized as:

$$a_c = \frac{1}{2} \min_{a_g} a_g^T M a_g \quad (6)$$

subject to $$J a_g \geq 1 \quad (7)$$

Note that the right hand side value "1" in Equation (7) can be chosen as any vector with identical elements. The choice of right hand side value can change the magnitude, but not the direction of the result from Equation (6).

Calculating the Force

The force f sent to the haptic rendering device can be calculated as a function of the difference between the virtual tool and haptic device configuration. For example, f can be specified as $f = (f_T \; f_R)^T$, with $f_T \in \mathbb{R}^3$ being a translational component, and $f_R \in \mathbb{R}^3$ being a rotational component. Then, $f_T$ can correspond to three degrees of freedom for a position of virtual tool VT and $f_R$ can correspond to three degrees of freedom for a rotation of virtual tool VT.

The force f can be calculated as:

$$f=KMa_{g_u} \qquad (8)$$

where K is a diagonal matrix containing spring constants between virtual tool VT and each contact point. For an example of spring constants, a virtual spring with a corresponding spring constant can be connected between virtual tool VT and a contact point. As the distance between VT and the contact point increases, the virtual spring exerts a proportionally larger force to draw VT closer to the contact point. The calculated force can be exerted in the direction of the normal at the contact point; i.e., corresponding to the virtual spring pulling VT and the contact point together.

Example Implementation

As an example, the herein-described 6-DOF haptic rendering algorithm was implemented on a desktop computer (AMD Phantom II X6 with a Radeon HD 6990 GPU) running Ubuntu 11.10. The force was calculated asynchronously at 1000 Hz in a separate thread. During typical interaction, the collision detection algorithm ran at 15 kHz. Point images were filtered and normal vectors were calculated for every point using the GPU.

Realtime processing was achieved using a neighborhood of 9×9 points for filtering as well as normal vector calculation. The position of the haptic rendering device was both controlled automatically (for purposes of producing accurate results) as well as with a Phantom Omni haptic rendering device. Using the latter, only translational forces could be perceived by the user since the Phantom Omni only provides 3 DOFs of sensation.

To evaluate the presented haptic rendering method in a noise free environment, a virtual box (with 5 sides but no top) was constructed. The normal vectors were set perpendicular to each side, pointing into the box. The position of the haptic rendering device was then automated to move 2 s into the box, rotate in the positive direction for 2 s, rotate in the opposite direction for 2 s, and then move for 2 s out of the box. In this example, the virtual tool became constrained by the sides of the box and interacted with up to 6 contact points simultaneously.

Two examples of haptic interaction with streaming point data were performed using arbitrary polygon models as virtual tools. The performance of the haptic rendering method can depend on the number of points in the neighborhood of the virtual tool. In some embodiments, most of the computational time can be spent on collision detection and forming movement constraints. In these embodiments, performance of the algorithm can scale approximately linearly in the number of neighboring points. To improve performance in interaction with large tools, the point data can be down-sampled. Further, performance can be enhanced by utilizing multiple CPUs of a computing device for collision detection. Also, the algorithm can be implemented partially or completely using interval arithmetic, which may improve performance as well.

Example Technique for Generating and Enforcing Virtual Fixtures

Figure 5A:
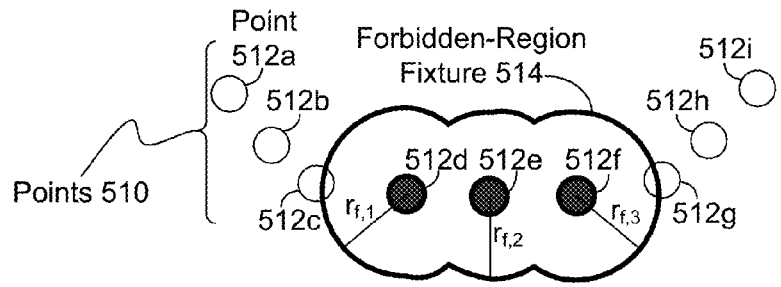
FIG. 5A depicts points derived from depth data and a forbidden region, in accordance with an example embodiment.

FIG. 5A depicts points 510 derived from depth data and forbidden-region fixture 514, in accordance with an example embodiment. FIG. 5A shows points 510 including points 512a-512i. Forbidden-region fixture 514 can define a forbidden region that includes some of points 510; e.g., points 512d-512f as shown in FIG. 5A, and surrounding space where a virtual tool is prohibited from entry.

A forbidden region can be generated by selecting points, planes, regions of space, and/or objects in a virtual environment to define the forbidden region. For each forbidden-region point $p_i$ completely within the forbidden region, a forbidden-region radius $r_{f,i}$ and a forbidden-region stiffness $k_{s,i}$ can be determined. FIG. 5A shows a two dimensional forbidden region feature defined by forbidden-region points 512d-512f and where $r_{f,1}=r_{f,2}=r_{f,3}$. During haptic rendering of points 510, a virtual tool will be prohibited from entering forbidden region 514.

During haptic rendering, the forbidden regions can be considered to be defined by forbidden-region spheres of the forbidden-region fixture, each forbidden-region sphere defined by a forbidden-region point $p_i$ and related forbidden-region radius $r_{f,i}$. Then, the virtual tool can be constrained to only move on the surface of or away from the forbidden-region spheres.

Figure 5B:
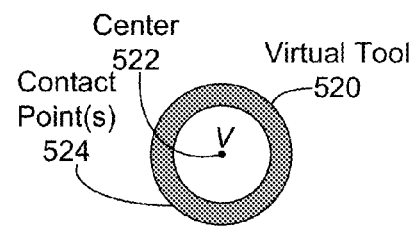
FIG. 5B depicts a virtual tool in accordance with an example embodiment.

FIG. 5B depicts virtual tool 520, in accordance with an example embodiment. Virtual tool 520 has a center 522, shown with a V in FIG. 5B. Virtual tool 520 also has contact point(s) 524, defined as one or more points on an exterior surface of virtual tool 520.

The definitions of virtual-tool states can be modified to account for forbidden regions. The virtual tool can be considered to be in a free-motion state with respect to one or more forbidden regions if the virtual tool is not on the boundary or inside of any of the one or more forbidden regions. The definition of depth can be similarly modified, so that a modified depth MD of a virtual tool VT with respect to a forbidden region F having outward normal FN can be specified as distance between contact point(s) of VT and a closest portion of forbidden region F moving in a direction of FN. In terms of the modified depth, VT is in a free-motion state with respect to forbidden region if the modified depth MD between VT and F is greater than 0.

The virtual tool can be considered to be in an in-contact state with respect to one or more forbidden regions if a portion of one or more of the forbidden region(s) is just touching contact point(s) 524; e.g., the modified depth MD between the virtual tool and the forbidden region equals 0. The virtual tool can be considered to be in an in-collision state with respect to one or more forbidden regions if a portion of one or more of the forbidden region(s) is within contact points of the virtual tool e.g., the modified depth MD between the virtual tool and the forbidden region is less than 0.

When the virtual tool is in a free motion state, movement along the vector of unconstrained acceleration is allowed as long as the virtual tool does not come in contact with or collide with a forbidden region; e.g., as long as the modified depth remains greater than zero.

Figure 5C:
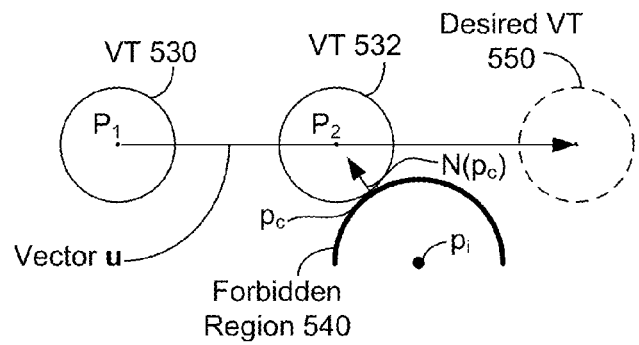
FIG. 5C shows an example virtual tool whose movement toward a desired position is impeded by a forbidden region, in accordance with an example embodiment.

FIG. 5C shows an example virtual tool 530 whose movement toward desired virtual tool position 550 is impeded by forbidden region 540, in accordance with an example embodiment. As shown in the example of FIG. 5C, forbidden region 540 centered at point $p_i$ can constrain movement of free-motion virtual tool 530 toward desired virtual tool position 550 in the direction of vector u. Specifically, FIG. 5C shows that when a center of virtual tool 530 moves to a position $P_2$, virtual tool 530 will be in contact with forbidden region 540 at point $p_c$. The outward normal to forbidden region $N(p_c)$ indicates a direction of motion for virtual tool 530 to avoid forbidden region 530.

Figure 5D:
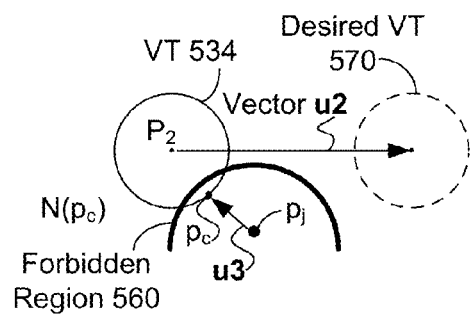
FIG. 5D shows an example virtual tool whose movement is in collision with a forbidden region, in accordance with an example embodiment.

FIG. 5D shows an example virtual tool 534 in collision with forbidden region 560 centered at point $p_j$, in accordance with an example embodiment. As shown in the example of FIG. 5D, a portion of virtual tool 534 is inside of, and so is in collision with, forbidden region 560. For example, forbidden region 560 can be generated based on new depth information received from a depth-enabled camera or similar device. In particular, point $p_c$ of the contact points for virtual tool 534 is a point furthest inside forbidden region 560; e.g., a point of virtual tool 534 closest to point $p_j$ centering forbidden region 560. As such, virtual tool 534 cannot travel along vector u2 toward desired virtual tool position 570 without at least partially traversing forbidden region 560. A vector u3 from center point $p_j$ to contact point $p_c$ indicates a direction of motion for virtual tool 535 to escape forbidden region 560; e.g., virtual tool 534 can move along a weighted vector sum of u2 and u3 to escape forbidden region 560 while progressing toward desired virtual tool position 570.

Example Applications Involving Haptic Rendering

Figure 6:
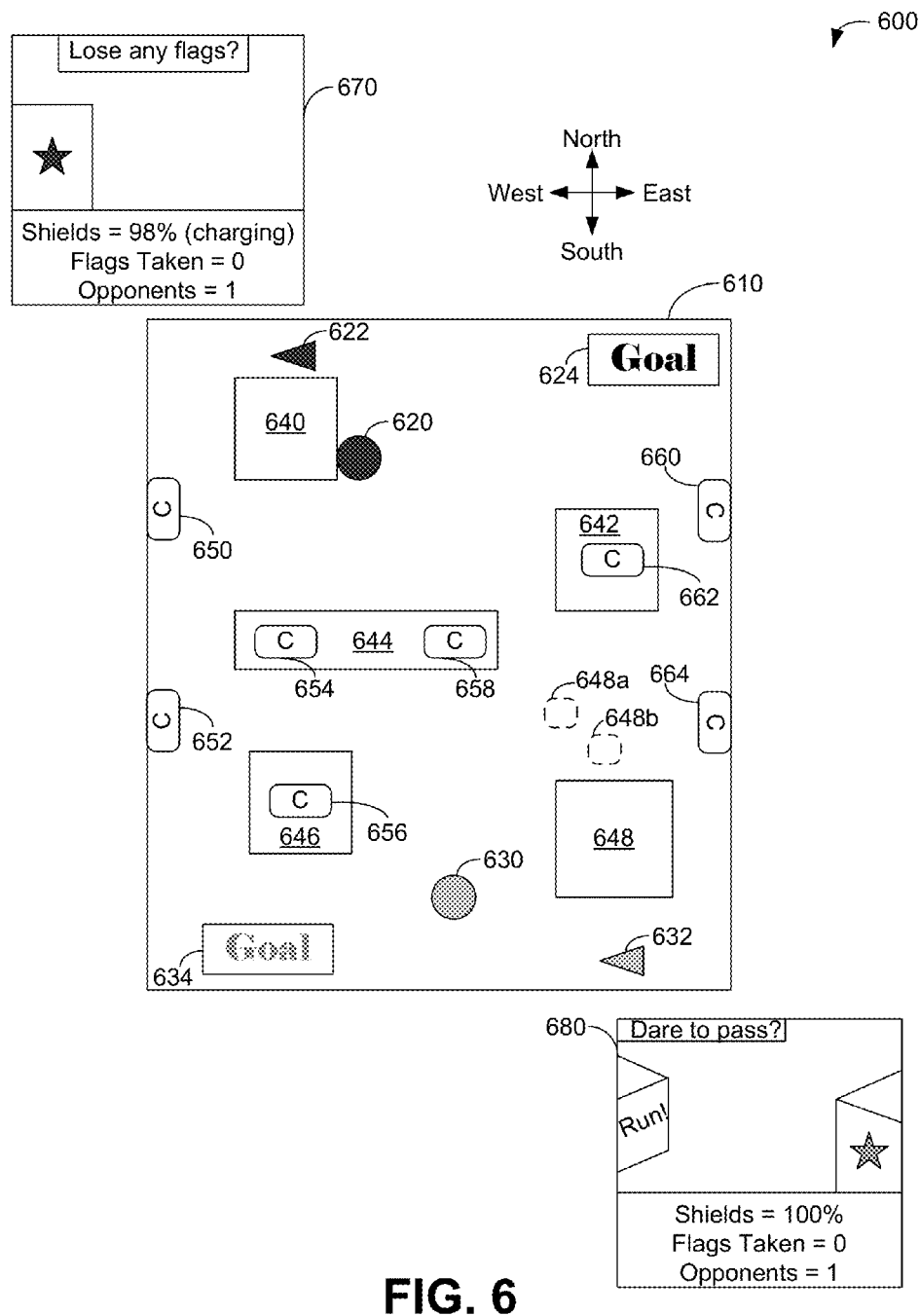
FIG. 6 is an example gaming scenario with haptic rendering, in accordance with an example embodiment.

FIG. 6 is an example gaming scenario 600 with haptic rendering in environment 610, in accordance with an example embodiment. In scenario 600, players 620 and 630 are playing a game of "capture the flag" in game environment 610. FIG. 6 shows player 620 as a black circle in game environment 610 and guarding flag 622, and shows player 630 as a grey circle in game environment 610 and guarding flag 632.

In capture the flag, each player tries to be the first player to capture the opponent's flag and return the captured flag to a goal area. That is, during the game, player 620 attempts to capture flag 632 and return flag 632 to goal 624 before player 630 captures flag 622 and returns flag 622 to goal 634. In the variation of capture the flag shown in scenario 600, a player can lose if a shield level for the player goes to 0% as well.

In scenario 600, both players 620 and 630 utilize haptic feedback devices, such as haptic gloves, body suits with haptic feedback generators, and/or other haptic devices. Also, players 620 and 630 each have computing devices configured to use game-playing software access a virtual environment generated from depth data generated by depth-enabled cameras 650, 652, 654, 656, 658, 660, 662, and 664 (labeled as C's in FIG. 6). In other scenarios, more or fewer cameras can be used than shown in FIG. 6. Also, in scenario 600, both players 620 and 630 have sensors configured to provide location and heading information for the player. For example, both players 620 and 630 could have a haptic suit with a portable display that includes Global Positioning System (GPS) sensor(s), accelerometer(s), gaze detection sensors, and/or other sensors to both access the virtual environment, provide location and heading information, and receive haptic feedback.

Software for the game can determine a location and heading for each player within environment 610 and generate a display of environment 610 at the player's location as the player looks in the heading direction. FIG. 6 shows display 670 generated for player 620 with a view of box 640 shown with a black star. In scenario 600, a "charging object", or star having the player's color on an object within environment 610 increases or "charges" the player's shield level as long as the player touches the object. In contrast, if the player touches a "discharging object", or object having a star of the color of the opponent, the player's shield level decreases or "discharges." In some embodiments, a discharging object can produce a forbidden zone that discharges a shield level while a player is within the forbidden zone. The colored star used for identification of charging and discharging objects can be generated by the game-playing software to permit changes in colors of player and/or changing which objects act as charging and/or discharging objects.

Also, in some embodiments, touching a discharging object can quickly or even immediately reduce a shield level to 0—e.g., the discharging object causes the player to (nearly) instantly lose the game. Depending on the scenario, such instant-discharge objects may or may not be identified to the player by the game-playing software.

Along with identification of charging and discharging objects, the game-playing software can generate slogans, images, etc. on objects in the environment. For example, in scenario 600, player 620 has a heading of due south, and the game-playing software has generated the slogan "Lose any flags?" on an image of object 644 in display 670. Similarly, in scenario 600, display 680 for player 630 has slogans "Dare to pass?" and "Run!" display on generated images of objects 644. In some scenarios, the game-playing software may provide images of objects without additional slogans, images, etc.

Displays 670 and 680 each include game-related data for each player, including a shield level, a number of flags taken, and a number of opponents in environment 610. For example, FIG. 6 shows display 670 for player 620 with game-related data that indicates that player 620: (a) has a shield level of 98% and that the shields are charging, (b) has not taken any flags, and (c) has one opponent in environment 610. FIG. 6 also shows display 680 for player 630 with game-related data that indicates that player 630: (a) has a shield level of 100%, (b) has not taken any flags, and (c) has one opponent in environment 610. In some embodiments, more, different, and/or less game-related data can be provided in a display for a player.

In some embodiments, the game-playing software can generate and/or display virtual objects as well as, or instead of, actual objects such as objects 640, 642, 644, 646, and 648 of environment 610. For example, objects 648a and 648b, each shown using dashed lines, can be virtual objects. As one example, a virtual object can represent a "regular" object similar to object 646 or 648 but is not physically present in environment 610. In other examples, a virtual object can represent a trap such as a "covered pit" that an unwary player can fall into and lose shield strength, or a treasure such as "supercharger" that can immediately add shield strength to the player.

Many other examples of real and virtual objects are possible, including examples of other games that utilize haptic rendering. Some of these games can involve only one player and some games can involve more than two players. For example, a maze game with haptic feedback can involve a single player exploring the maze or can involve two or more players perhaps running a race through the maze.

Figure 7:
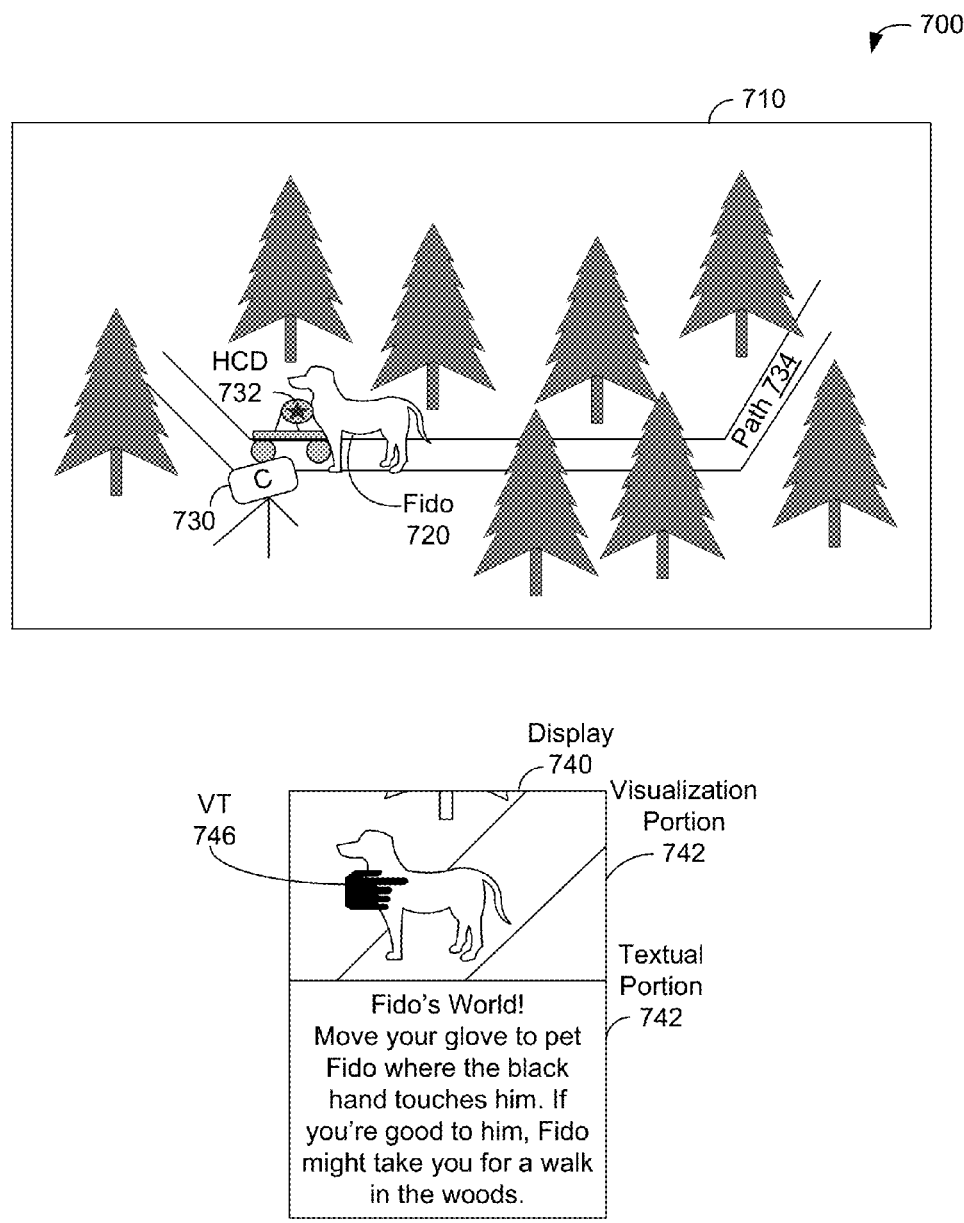
FIG. 7 is an example scenario for a haptic rendering session in a remote environment, in accordance with an example embodiment.

FIG. 7 is an example haptic rendering session scenario 700 in a remote environment 710, in accordance with an example embodiment. Environment 710 includes a dog "Fido" 720, a depth-enabled camera 730, and a haptically-controlled device (HCD) 732. During scenario 700, a remote viewer interacts with Fido 720 via HCD 732. For example, HCD 732 can be a mobile robot with a robot arm configured for remote control. Other HCDs are possible as well. In some scenarios, HCD 732 is not present, which permits interaction with a virtual environment generated by data from camera 730 without the ability to affect a real environment, such as environment 710.

Display 740 can be generated to visualize a virtual environment utilizing depth data generated by depth-enabled camera 730. FIG. 7 shows display 740 with visualization portion 742 configured to display a view of environment 710 and textual portion 744 configured to display both instructions, such as "Move your glove to pet Fido where the black hand touches him", and other information such as "If you're good to him, Fido might take you for a walk in the woods."

A user conducting a haptic rendering session scenario can use a haptic glove or other haptic interface device to control virtual tool 746 and touch Fido 720 using the robot arm of HCD 732. In some scenarios, the user can control movement of HCD 732, perhaps by certain movements of the haptic interface device; e.g., press a "move robot" button or otherwise signal a change of interpretation of movements of the haptic interface device from being interpreted as commands for moving the robot arm to commands for moving HCD 732.

In scenario 700, the move robot button can be pressed to move HCD 732 along path 734 and so walking Fido 720 based on movements of the haptic interface device (e.g., move haptic interface device left or right to correspondingly move HCD 732 left or right along path 734, rotate haptic interface device to better pet Fido). When the move robot button is not pressed, movements of the haptic interface device control the robot arm (e.g., for a haptic glove acting as the haptic interface device, Fido 720 can be petted or scratched based on finger movements of the haptic glove).

In other scenarios, non-haptic interface devices can be used to control HCD 732; e.g., the haptic interface device controls the robot arm and a joystick or keyboard can be used to move the mobile robot. In still other scenarios, camera 730 can be mounted on HCD 732 to provide additional information about environment 710, including information about Fido 720.

Figure 8:
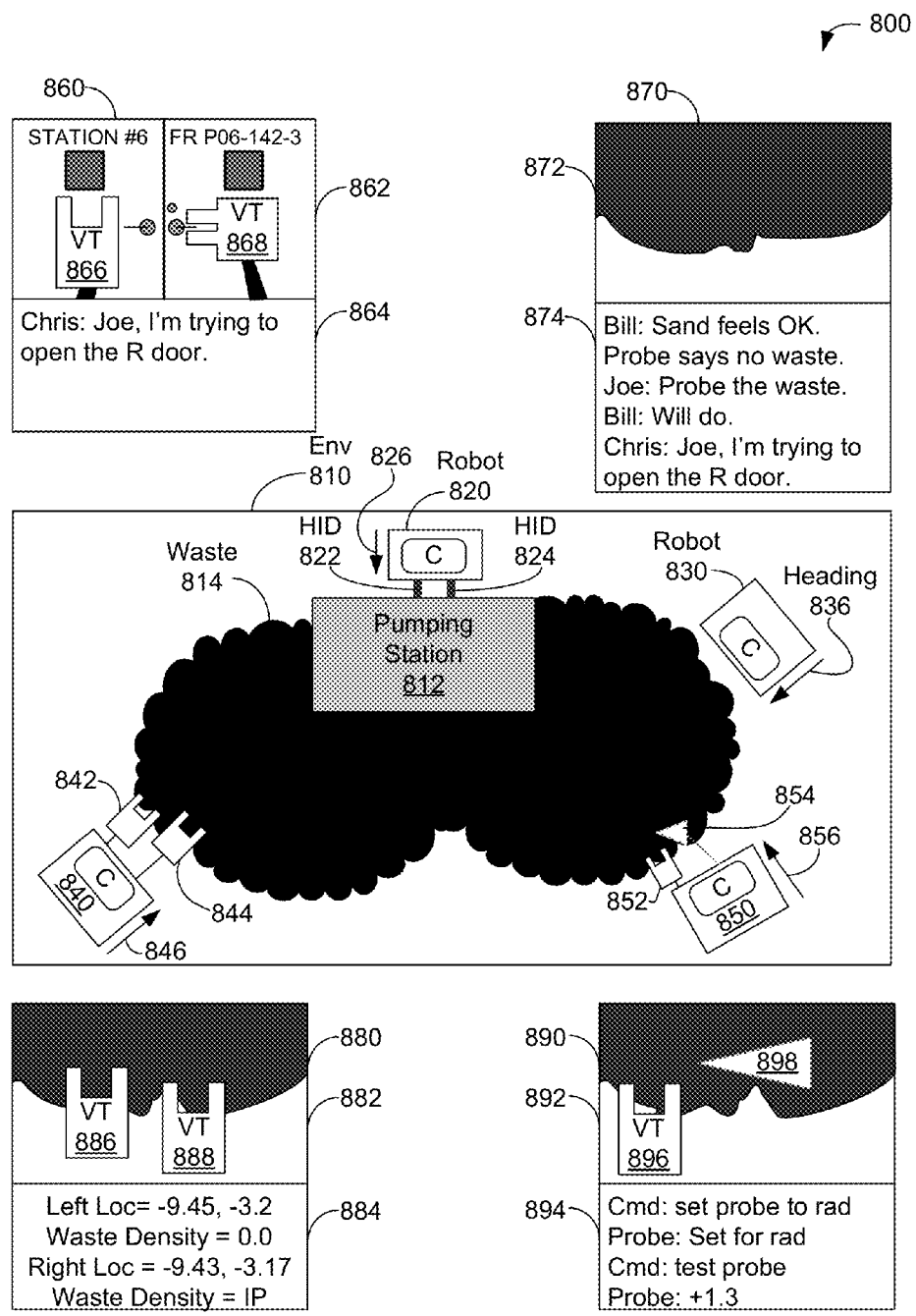
FIG. 8 is an example scenario for collaborative haptic rendering sessions in a remote environment, in accordance with an example embodiment.

FIG. 8 is an example collaborative haptic rendering session scenario 800 for a remote environment 810, in accordance with an example embodiment. Environment 810 includes pumping station 812 that, during scenario 800, has failed. Due to the failure of pumping station 812, waste 814 has escaped, as shown by FIG. 8 as a black cloud in environment 810.

During scenario 810, four robots 820, 830, 840, and 850 have been deployed to fix pumping station 810 and investigate environment 810 to begin cleaning waste 814. Each of robots 820, 830, 840, and 850 has a depth-enabled camera facing forward and can be driven by a remote operator using a display, such as display 312 discussed above in the context of FIG. 3A, and one or more haptic interface devices, such as haptic interface device(s) 316 discussed above in the context of FIG. 3A.

In scenario 800, each robot operator is in a different physical location. Each location is equipped with one or more haptic interface devices, one or more displays, and perhaps other interface devices, such as keyboards, keypads, touch screens, loudspeakers, microphones, and/or other interfaces. In other scenarios, some or all of the robot operators can be in the same remote location. In still other scenarios, a single robot can be used with a single robot operator. In even other scenarios, one or more of the robots can be controlled by multiple robot operators e.g., both a driver and a ladder operator can control a robotic fire engine. In yet other scenarios, one or more of the robot operators can be local; e.g., at environment 810, perhaps riding on or within a robot.

FIG. 8 shows the displays generated the depth-enabled cameras for the robot operators, as display 860 for robot 820 headed along heading 826, display 870 for robot 830 headed along heading 836, display 880 for robot 840 headed along heading 846, and display 890 for robot 850 headed along heading 856. Robot 820 has two robot hands configured as haptic interface devices (HIDs) 822, 824, robot 840 has two robot hands 842, 844 configured as haptic interface devices, and robot 850 has robot hand 852 and probe 854 configured as haptic interface devices. Each robot display shown in FIG. 8 includes a visualization portion and a textual portion, similar to display 1040 shown in FIG. 10. For example, display 860 includes visualization portion 862 and textual portion 864. In FIG. 8, virtual tools representing robot hands are shown using block diagrams of hands with two fingers and virtual tools representing probes are shown using slender triangles; e.g., pennant-shaped triangles.

In scenario 800, robot 830 is in communication with the other robots 820, 840, and 850, and is configured to a "communication coordinator" to send and receive text, voice, and perhaps other types of messages from the other robot operators. For example, robot 830 can be controlled by a supervisor observing environment 810 and coordinating the efforts of robots 820, 840, and 850.

In scenario 800, a far end of each robot arm of robot 820 is configured to be a virtual tool for the operator of robot 820. FIG. 8 shows display 860 for robot 820 including a location of a left virtual tool 866, corresponding to a left robot hand on a left arm of robot 820, and a right virtual tool 868 corresponding to a right robot hand on a right arm of robot 820. In FIG. 8, right virtual tool 868 is position to move a handle of a door to pumping station 812.

The operator of robot 820 can use a non-haptic interface device, such as a keyboard or keypad to enter text that appears in textual portion 864. FIG. 8 shows that the text "Joe, I'm trying to open the R door." Is in textual portion 864, preceded by an identifier "Chris" of a person who entered in the text; e.g., Chris is a first name of the operator of robot 820. In scenario 820, text entered into a textual portion 864 of display 860, textual portion 884 of display 880, or textual portion 894 of display 890 is displayed both in the entering textual portion plus in textual portion 874, as display 870 and textual portion 874 are associated with the communication coordinator. In some embodiments, robot operators can send a message to one or more other operators directly without sending a copy of the message to the communication coordinator.

In other embodiments, the operator of robot 820 can receive touch feedback while attempting to open the door of pumping station 812. For example, as the operator of robot 820 uses robot hand 822 to open the door of pumping station 812, haptic rendering can provide feedback to indicate that the door is or is not resisting the efforts to open the door. Further, in embodiments where robot hand 822 is equipped with finger-like appendages, the operator of robot 820 can use a haptic glove or other haptic interface device to move the appendages to grab the door handle, and pull down or push up with an amount of effort based on, e.g., proportional to, an amount of effort exerted by the operator in moving the haptic interface device.

Robot 850 is equipped with probe 854. A probe can be equipped with one or more sensors for chemical, biological, and/or radiation testing. FIG. 8 shows robot 850 with probe 854 in waste 814.

Each of displays 880 (for robot 840) and 890 (for robot 850) shows a virtual tool associated with either a robot hand or a probe. For example, for robot 840, robot hand 842 is associated with virtual tool 886 and robot hand 844 is associated with virtual tool 888. In scenario 800, both robot hands 842 and 844 include probes.

Robot 840 is engaged in measuring waste densities with robot hands 842 and 844. FIG. 8 shows textual portion 884 of display 880 displaying various types of information, including location information for each probe and waste density values detected by each probe. In scenario 800, a waste density of "IP" indicates a probe is in the process of determining a waste density, such as shown in FIG. 8 for probe 844.

Both haptic and non-haptic commands can be used to control robots. Textual portion 894 of display 890 shows commands being communicated from an operator to robot 850. FIG. 8 shows a "Cmd:" prompt for commands, such as "set left to rad", which directs robot 850 to set a probe 854 to act as a radiation sensor. Robot 850 responds with a confirmatory message from "Probe" of "Set for rad" to indicate that probe 854 is ready for radiation testing. In scenario 800, the operator of robot 850 sends another command "test probe" to robot 850. In response, probe 854 performs a radiation test and determines a value of "+1.3" for the radiation test. In scenario 800, the operator of robot 850 can move robot hand 852 and probe 854 using respective haptic interface devices.

Figure 9:
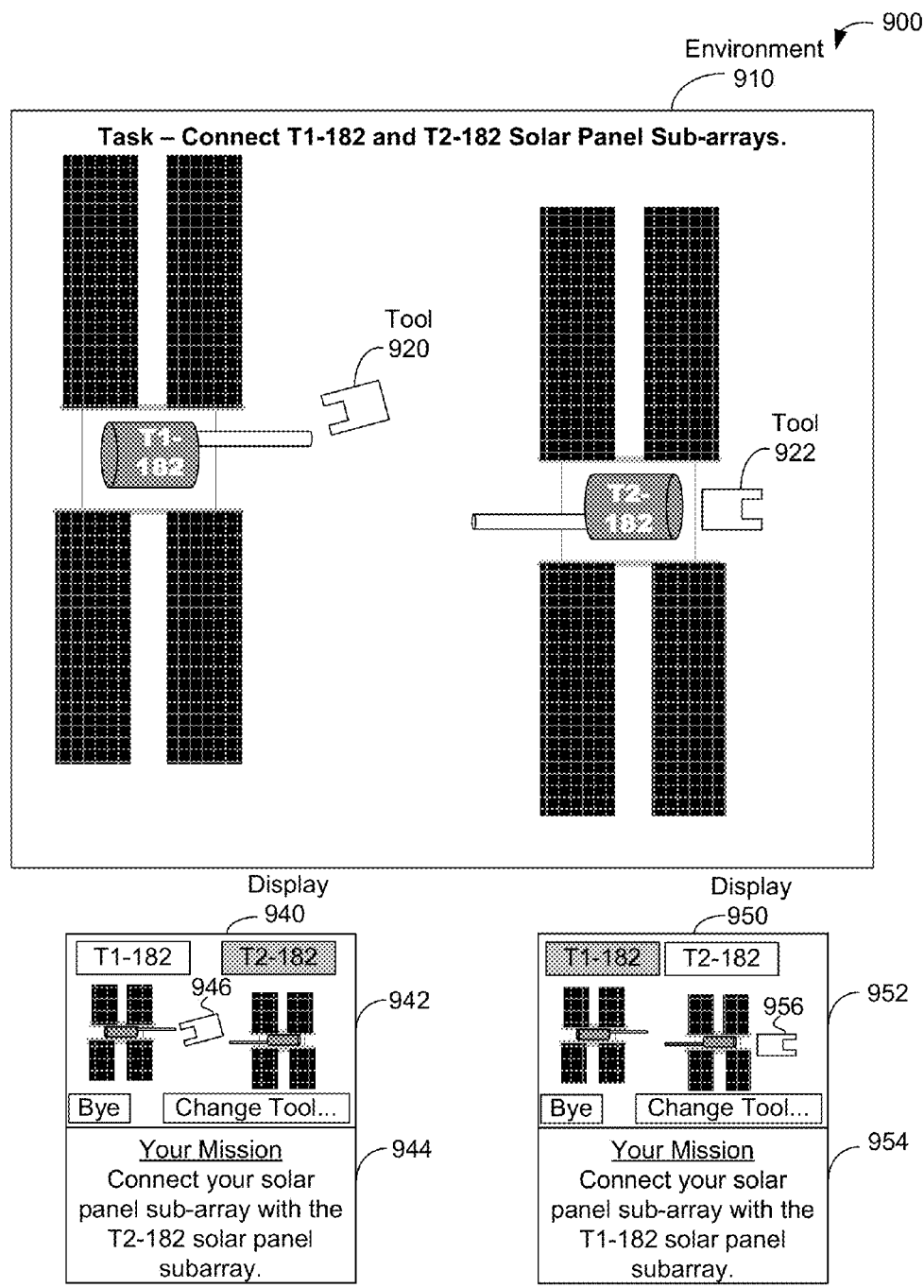
FIG. 9 depicts a construction scenario, in accordance with an example embodiment.

FIG. 9 depicts scenario 900 where construction is ongoing in environment 910, in accordance with an example embodiment. Environment 910 can be a virtual environment or an actual environment. In some embodiments, environment 910 can represent an extra-terrestrial environment; e.g., in space or on a planet other than Earth. In these embodiments, values of various parameters, such as the speed of gravity (if any), planetary tilt, and relative location of other celestial bodies, can change from Earth-normal values.

In scenario 900, a solar power array is being constructed from at least two depicted sub-arrays: sub-array T1-182, shown on the left side of environment 910, and sub-array T2-182, shown on the right side of environment 910. To construct the solar power array, sub-array T1-182 is being manipulated by tool 920 and sub-array T2-182 is being manipulated by tool 922. In other scenarios, more or fewer tools can be utilized in environment 910.

In scenario 900, display 940 is used to monitor and control a haptic interaction session with tool 920 and display 950 is used to monitor and control tool a haptic interaction session with tool 922. Display 940 includes environmental-display region 942 and textual-display region 944. Environmental-display region 942 includes a display of sub-arrays T1-182 and T2-182, virtual tool 946 representing tool 920, and two control buttons. The "Bye" control button ends the haptic interaction session and the "Change Tool" button enables changing display 940 to monitor/control to a different virtual tool and/or to change operation of tool 920; e.g., changing use of a robot hand as part of tool 920 as shown in FIG. 9. More, fewer and/or different control buttons can be utilized in other scenarios. Textual-display region 944 can provide text and perhaps other types of information (e.g., images, sounds, sensor information, communication sessions, etc.) for use as part of display 940.

Virtual tool 946, and subsequently tool 920, can be controlled by use of a 6 DOF (or other) haptic interface to enable control over location and rotation of virtual tool 946 and to receive force feedback related to related to the virtual tool using the herein-described techniques.

In other scenarios, display 940 can be used to monitor and control multiple haptic interaction sessions: for example, a robot arm can have three virtual tools corresponding to a shoulder, an elbow, and a wrist, with each virtual tool having up to 6 DOF. Then, if display 940 were used to control the robot arm, display 940 can control haptic interaction sessions for each of the virtual tools. As another example, a tool can have multiple controllable components; e.g., robot arms, robot hands, an engine/propulsion system, etc., where some or all of the controllable components can be directed using haptic interaction session(s). Then, if display 940 were used to monitor and control such a tool, display 940 can control one or more haptic interaction session(s) with the tool. Many other examples are possible as well.

Display 950 is similar to display 940. Display 950 includes environmental-display region 952 and textual-display region 954. Environmental-display region 952 includes a display of sub-arrays T1-182 and T2-182, virtual tool 956 representing tool 922, and "Bye" and "Change Tool" control buttons discussed above in the context of display 940. Textual-display region 954 can provide text and perhaps other types of information for use as part of display 950.

In scenario 900, tools 920 and 922, controlled via respective displays 940 and 950 and corresponding haptic interaction sessions, construct the solar power array using sub-arrays T1-182 and T2-182. Scenario 900 can then end.

Underwater Haptic Rendering Applications

Virtual tools, haptic interaction sessions, and the herein-described techniques can be applied to underwater applications. For example, a underwater depth-enabled camera, similar in spirit to the Microsoft Xbox Kinect, but suitable for underwater conditions can be used for locating objects underwater and providing data for 6 DOF haptic feedback to a human operator of the robot. The haptic feedback can provide a human operator with a sense of touch for objects seen by the camera.

This system can: (a) permit the operator to 'feel' objects, such as underwater ordnance during remediation or objects being salvaged, through a haptic 6 DOF interface, based upon the camera system image and dynamic haptic rendering, (b) enable the operator to guide the robot end-effectors with the target during removal, via tele-operation, and (c) establish virtual 'force fields' around protected zones of objects (such as locations that might result in explosion of the ordnance). If the tele-operator tries to move an end-effector too close to a protected zone, he/she will feel resistance as the haptic interface "pushes back". Imposition of protected zones, perhaps via virtual features, can prevent robot end effector contact with undesirable locations, either in the environment or on the ordnance. The end effector of a robot can be a device at an end of a robot arm or other appendage; e.g., a robotic hand at the end of robot arm. Combined with a tele-operated robotic device, this will allow human directed robotic capture and removal of objects under fresh or salt water.

Figure 10:
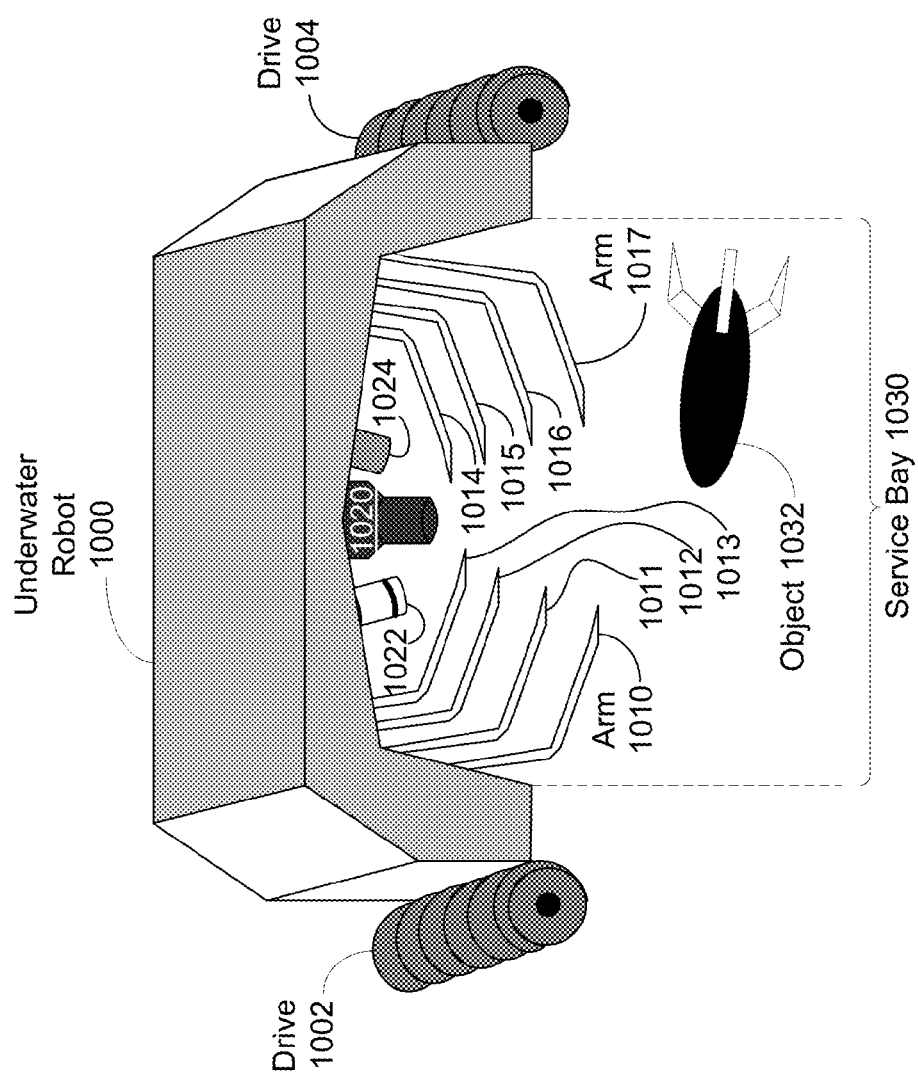
FIG. 10 shows an underwater robot, in accordance with an example embodiment.

FIG. 10 shows underwater robot 1000, in accordance with an example embodiment. Robot 1000 is configured with two screw drives 1002, 1004, eight robotic arms 1010, 1011, 1012, 1013, 1014, 1015, 1016, 1017, light sources 1020, 1024, and camera 1022.

Robot 1000 can be a bottom-crawling vehicle with a screw-drive propulsion system. Robot 1000 can move over an underwater object, such as ordnance, and the tele-operator uses robot arms 1010-1017 to grab the underwater object. Light sources 1020, 1024 and camera 1022 can operate together as a camera system.

As shown in FIG. 10, camera system 1020, 1022, 1024 can be integrated into a chassis of robot 1000 and image the region within service bay 1030. Camera system 1020, 1022, 1024 can generate a three-dimensional image of object(s) within service bay 1030, such as object 1032. The images generated by camera system 1020, 1022, 1024 can be provided to a processor at the surface to haptically rendering images within service bay 1030. A human tele-operator interacts with robot 1000, arms 1010-1017, and objects such as object 1032, using one or more haptic interfaces and perhaps display(s). The tele-operator can control arms 1010-

1017 to move object 1032, pick up object 1032, attach a sling and cable to object 1032 for future retrieval, and/or some other action such as mark the object for better identification.

Robot 1000 can use a system of screw drives 1002, 1004 for propulsion. Using screw drives maintains negative buoyancy throughout a mission and thus robot 1000 need not manage buoyancy. The use of screw drives, in contrast to thrusters, lowers the risk of stirring up silt or sand, which can deteriorate visibility. Additionally, silt poses a challenge to traditional track-driven vehicles not faced by screw drives.

FIG. 10 shows that screw drives 1002, 1004 are mounted on each side of robot 1000. Each screw drive 1002, 1004 can be driven at varying speeds. Robot 1000 can move sideways and thrust may be vectored so that non-holonomic constraints do not limit operation. Thrust vectoring allows for increased maneuverability and simplifies the role of the tele-operator, allowing for natural modes of operation and quick adjustments to the platform's location on the sea, river, or lake bed. Screw drives 1002, 1004 can also be articulated, allowing for a range of maneuvers and for convenient movements such as vertical translation of the chassis and service bay 1032 of robot 1000. In some scenarios, screw drives 1002, 1004 can dig into mud, getting the robot 1000 deeper into areas that may have buried ordnance.

Robotic manipulation and removal of munitions requires a stable platform that can remain fixed in an inertial frame with respect to the object. To carefully and firmly grip an object identified for removal, the system can use a number of robotic manipulators designed for the task, such as arms 1010-1017.

Arms 1010-1017 can have a series of linkages and the necessary actuation to achieve motion derivatives that accomplish desired gripping maneuvers to handle underwater objects. In some embodiments, such as shown in FIG. 10, each of arms 1010-1017 is identical and is designed for planar motion. When gripping an object, the trajectory of each of arms 1010-1017 is designed to achieve optimal grasping with respect to the goals and constraints defined by a human operator.

In some embodiments, some of arms 1010-1017 can be controlled using a low number of degrees of freedom. Even with low degree-of-freedom arms, intricate shapes can still be achieved with the coordinated manipulator system to allow for a high level of dexterity using simple components. As shown in FIG. 10, arms 1010-1017 can be mounted along either side of the service bay 1030, allowing them to oppose on another so that simple motions can result in stable gripping of munitions. The use of eight arms allows for a lower contact pressure on an object from each contacting arm. Also, a subset of arms 1010-1017 can be used, such as when a forbidden-region fixture on object 1032 prohibits one or more arms from gripping object 1032 at a particular location. In some embodiments, robot 1000 and arms 1010-1017 can operate in several modes of operation and redundancy, allowing an operator to carry out tasks even when a manipulator suffers damage.

The camera system can use a 'range gated' approach to allow both visible (blue green) and NIR images to be captured in combined stream of visible (blue green) and NIR images. Light source 1020 can be configured with blue-green filters and/or blue-green light-emitting diodes. The blue-green filters are configured to pass through light in a blue-green frequency range of 450-480 nm, while the blue-green diodes are configured to emit light in the blue-green frequency range.

Light source 1024 can include a NIR laser and a diffraction grating. The NIR laser and diffraction grating project a pseudo-random of dots of varying intensities. Camera 1022 can measure depth from the distortion between the projected and observed dot patterns. In some embodiments, the pulse duration for the NIR laser can be shorter than the time to travel to the target to reduce back scatter.

Camera system 1022 can be configured to capture the visible (blue green) and NIR images alternatively; that is illumination and camera frames are synchronized to capture the visible (blue green) and NIR images alternatively. That is, light sources 1020, 1024 can be alternatively activated at frame speed of camera 1022 to capture visible and NIR images in a single image stream. Dual-wavelength camera system 1022 can allow robot 1000 to obtain 2D images with depth measurements in low light conditions using a single camera. In some embodiments, camera system 1022 can be configured as an endoscope. Camera 1022 can include one or more adapters to combine the projected mask pattern from the light source 1024 with visible light source 1020, and recover the depth information from the reflected light with a wavelength-specific beam splitter.

In some embodiments, camera 1022 can be a modified 0° or 30° 10 mm endoscope with light sources and detectors separated by fixed distances. In particular embodiments, camera 1022 can output frames with VGA resolution (720× 900 pixels) at 30 frames per second, in RGB+Depth (RGB+D) format.

To calibrate the visible and depth images, planar calibration of camera system 1020, 1022, 1024 can first be performed on a planar surface with a checkerboard pattern. With camera system 1020, 1022, 1024 configured for close depth detection, the checkerboard can be produced with photolithographic techniques for both scale and accuracy. After planar testing is complete, optical testing of camera system 1020, 1022, 1024 can be performed on an irregular non-planar surface to determine a depth resolution, and any effect of geometric distortion on the optical distortion of camera system 1020, 1022, 1024. If distortion is detected, a distortion-correction technique that automatically calculates correction parameters without precise knowledge of horizontal and vertical orientation can be used to correct the detected distortion.

Camera system 1020, 1022, 1024 is discussed in more detail below in the context of at least FIGS. 17 through 29.

The above-mentioned haptic rendering process can use camera system 1020, 1022, 1024 to generate depth data, depth images, and haptic feedback. The haptic feedback can give a tele-operator a "feel" for underwater objects that are within the field of the underwater video+depth cameras, such as underwater ordnance during remediation. The tele-operator's console (to transmit operator control actions as well as haptic feedback) can use two haptic interface devices such as discussed above in the context of FIG. 3A. As the tele-operator moves the robot through the haptic interface devices, he/she can feel a "force field" of increasing impedance, as proximity of the tool tip to the virtual fixture boundary decreases.

Virtual fixtures can be established around the portion of protected structure; that is, structures not to be touched during a remediation procedure. Force-feedback virtual fixtures designed can improve the economy, speed and accuracy of user motions in the tele-operated environment. In particular, forbidden-region fixtures (FRFs) driven by haptic rendering information obtained from depth-enabled camera(s) can be used in two feedback control paths in this co-robotic system: by the tele-operator, and by a position control system for robot 1000.

Virtual fixtures around critical parts of a target (e.g., locations that would trigger explosion of the ordnance) can be designated by operator input or through image recognition. For operator designation of a virtual fixture, the tele-operator will specify the boundaries of virtual fixture either using a haptic interface device, or by using mouse, touch screen, or other input on a video display. At any time during operation of robot 1000, a tele-operator of robot 1000 can re-define virtual fixtures by drawing on a real time image, or by repeating the virtual fixture designation process. For automatic recognition, an image recognition capability could be used to specify 'no touch' zone(s) based on objects detected from images captured by camera system 1020, 1022, 1024.

Effectors at ends of robot arms 1010-1017 can be tracked in real time. Using the haptic rendering algorithms described herein, haptic feedback can be provided to the tele-operator, such as pushing back if an effector gets too close to a protected location; i.e., near or within a forbidden region defined by a virtual fixture, such as a forbidden-region fixture. Additionally or instead, if an effector gets too close to a protected location, robot control actions can be modified to lock out certain motions. For example, suppose a forbidden region had been defined that was directly astern from robot 1000. Then, if the tele-operator of robot 1000 attempted movement of one or more of arms 1010-1017 backwards close to or within the forbidden region, haptic feedback, such as resistance, can be used to inform the tele-operator about the forbidden region. Additionally or instead, backward movements of robot 1000 can be inhibited while the forbidden region remains directly astern of robot 1000. In some embodiments, both providing haptic information and dynamic robot responses can be modified; such as both providing resistance to the tele-operator and slowing down motion of robot 1000 that is near or within a boundary of a virtual fixture. Many other examples are possible as well.

An Example Computing Network

Figure 11A:
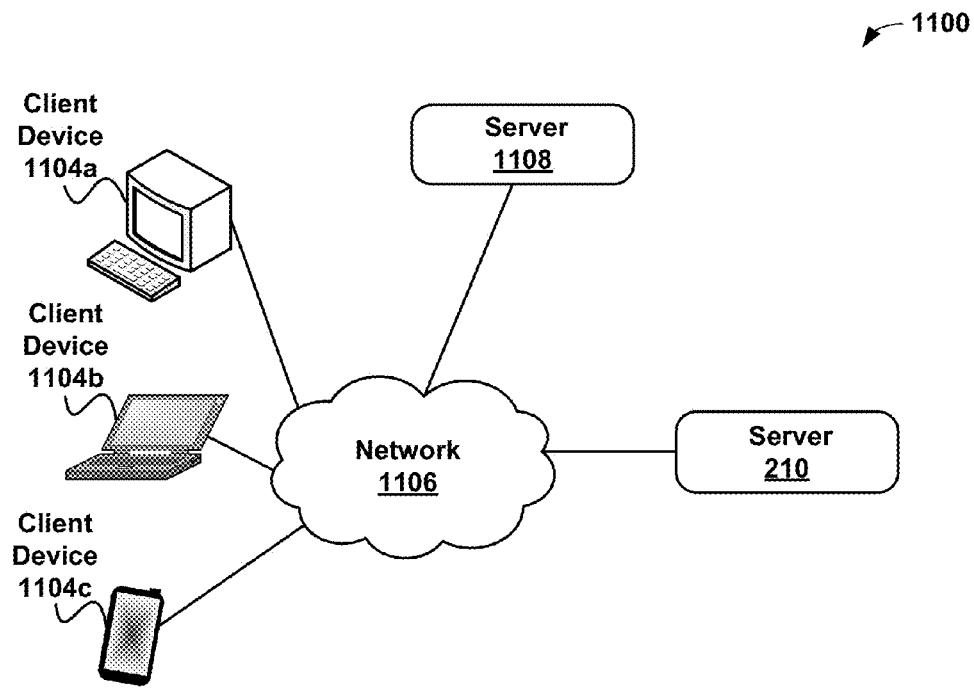
FIG. 11A is a block diagram of a computing environment, in accordance with an example embodiment.

FIG. 11A depicts a network 1100 in accordance with an example embodiment. In FIG. 11A, servers 1108 and 1110 are configured to communicate, via a network 1106, with client devices 1104a, 1104b, and 1104c. As shown in FIG. 11A, client devices can include a personal computer 1104a, a laptop computer 1104b, and a smart-phone 1104c. More generally, client devices 1104a-1104c (or any additional client devices) can be any sort of computing device, such as a workstation, network terminal, desktop computer, laptop computer, wireless communication device (e.g., a cell phone or smart phone), and so on.

The network 1106 can correspond to a local area network, a wide area network, a corporate intranet, the public Internet, combinations thereof, or any other type of network(s) configured to provide communication between networked computing devices. Servers 1108 and 1110 can share content and/or provide content to client devices 1104a-1104c. As shown in FIG. 11A, servers 1108 and 1110 are not physically at the same location. Alternatively, servers 1108 and 1110 can be co-located, and/or can be accessible via a network separate from network 1106. Although FIG. 11A shows three client devices and two servers, network 1106 can service more or fewer than three client devices and/or more or fewer than two servers.

An Example Computing Device

Figure 11B:
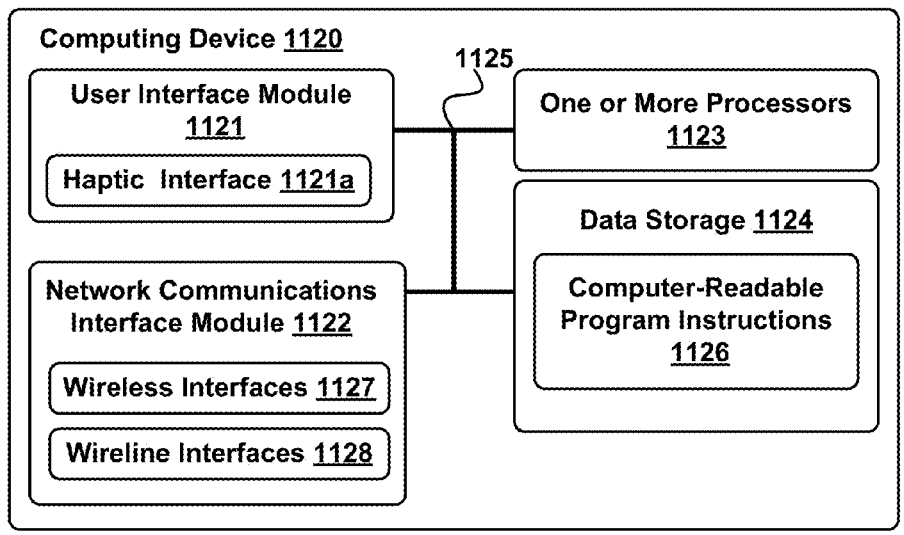
FIG. 11B is a block diagram of an example computing device, in accordance with an example embodiment.

FIG. 11B is a block diagram of an example computing device 1120 including user interface module 1121, network-communication interface module 1122, one or more processors 1123, and data storage 1124, in accordance with embodiments of the invention.

In particular, computing device 1120 shown in FIG. 11A can be configured to perform one or more functions of client devices 1104a-1104c, networks 310, 1106, 1720, servers 1108, 1110, computing devices 320a, 320b, 1724, robot 1000, 1784, software 1310, task-management software, master console 1710, camera 1780, 1800, depth sensor 1782, sensor system 1860, 2600, 2630, system 2200, 2300, metal detector 2420, 2460, and/or metal detector system 2500, 2520, 2540, and/or to implement part or all of architecture 1300, pipeline 1400, remote virtual environment 1704, and/or scenario 2800. Computing device 1120 can include a user interface module 1121, a network-communication interface module 1122, one or more processors 1123, and data storage 1124, all of which may be linked together via a system bus, network, or other connection mechanism 1125.

Computing device 1120 can be a desktop computer, laptop or notebook computer, personal data assistant (PDA), mobile phone, embedded processor, or any similar device that is equipped with at least one processing unit capable of executing machine-language instructions that implement at least part of the herein-described techniques and methods, including but not limited to method 1200 described in more detail below with respect to FIG. 12.

User interface 1121 can receive input and/or provide output, perhaps to a user. User interface 1121 can be configured to send and/or receive data to and/or from user input from input device(s), such as a keyboard, a keypad, a touch screen, a computer mouse, a track ball, a joystick, and/or other similar devices configured to receive user input from a user of the computing device 1120. User interface 1121 can be configured to provide output to output display devices, such as. one or more cathode ray tubes (CRTs), liquid crystal displays (LCDs), light emitting diodes (LEDs), displays using digital light processing (DLP) technology, printers, light bulbs, and/or other similar devices capable of displaying graphical, textual, and/or numerical information to a user of computing device 1120. User interface module 1121 can also be configured to generate audible output(s), such as a speaker, speaker jack, audio output port, audio output device, earphones, and/or other similar devices configured to convey sound and/or audible information to a user of computing device 1120. As shown in FIG. 11B, user interface module 1121 can be configured with haptic interface 1121a that can receive inputs related to a virtual tool and/or a haptic interface point (HIP), a remote device configured to be controlled by haptic interface 1121a, and/or other inputs, and provide haptic outputs such as tactile feedback, vibrations, forces, motions, and/or other touch-related outputs.

Network-communication interface module 1122 can be configured to send and receive data over wireless interfaces 1127 and/or wired interfaces 1128 via a network, such as network 1106. Wired interface(s) 1128, if present, can comprise a wire, cable, fiber-optic link and/or similar physical connection to a data network, such as a wide area network (WAN), a local area network (LAN), one or more public data networks, such as the Internet, one or more private data networks, or any combination of such networks. Wireless interface(s) 1127 if present, can utilize an air interface, such as a ZigBee, Wi-Fi, and/or WiMAX interface to a data network, such as a WAN, a LAN, one or more public data networks (e.g., the Internet), one or more private data networks, or any combination of public and private data networks.

In some embodiments, network-communication interface module 1122 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well as or in addition to those listed herein to secure (and then decrypt/decode) communications.

Processor(s) 1123 can include one or more central processing units, computer processors, mobile processors, digital signal processors (DSPs), GPUs, microprocessors, computer chips, and/or other processing units configured to execute machine-language instructions and process data. Processor(s) 1123 can be configured to execute computer-readable program instructions 1126 that are contained in data storage 1124 and/or other instructions as described herein.

Data storage 1124 can include one or more physical and/or non-transitory storage devices, such as read-only memory (ROM), random access memory (RAM), removable-disk-drive memory, hard-disk memory, magnetic-tape memory, flash memory, and/or other storage devices. Data storage 1124 can include one or more physical and/or non-transitory storage devices with at least enough combined storage capacity to contain computer-readable program instructions 1126 and any associated/related data structures.

Computer-readable program instructions 1126 and any data structures contained in data storage 1126 include computer-readable program instructions executable by processor(s) 1123 and any storage required, respectively, to perform at least part of herein-described methods, including but not limited to method 1200 described below with respect to FIG. 12, method 1600 described below with respect to FIG. 16, and/or method 2200 described below with respect to FIG. 22. Computer-readable program instructions 1126 can include instructions that when executed by processor(s) 1123 to perform the herein-described functionality of software, such as, but not limited, to software 1310 and/or task-management software.

An Example Method for Six Degree of Freedom Haptic Rendering

Figure 12:
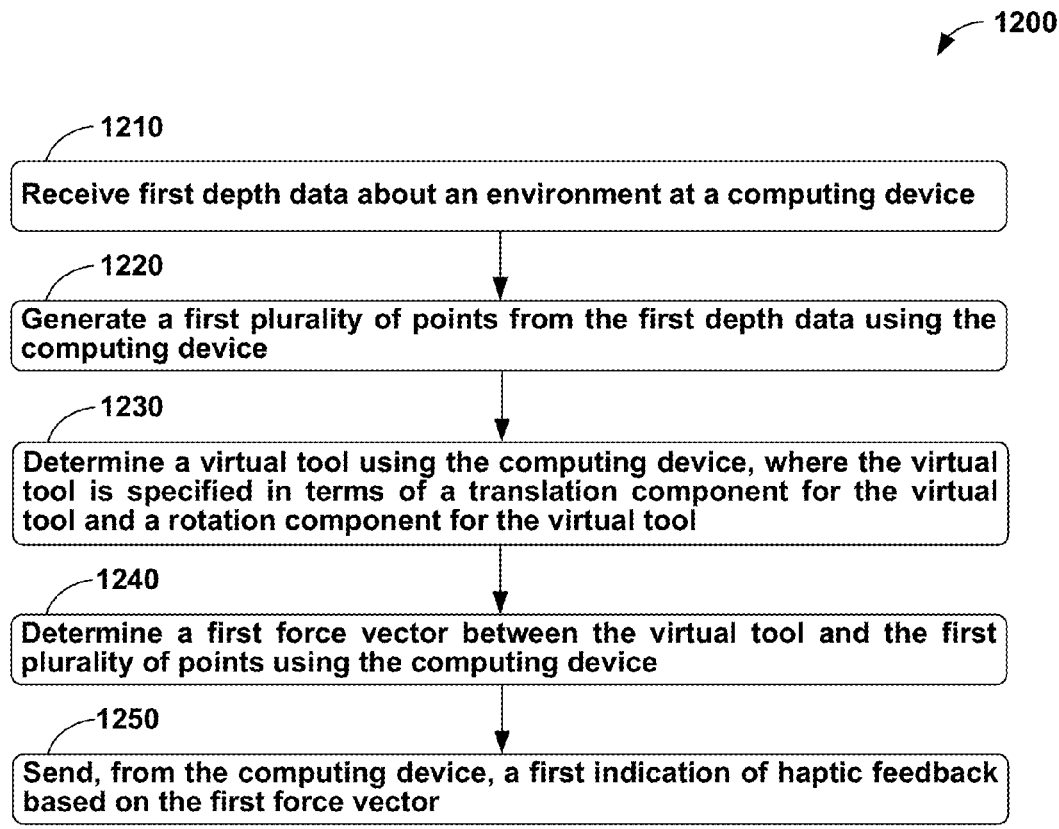
FIG. 12 is a flowchart of a method, in accordance with an example embodiment.

FIG. 12 is a flowchart depicting example functional blocks of an example method 1200. Method 1200 begins at block 1210, where a computing device can receive first depth data about an environment, such as discussed above in detail in the context of at least Table 1 and FIGS. 3A and 3B.

At block 1220, the computing device can generate a first plurality of points from the first depth data, such as discussed above in detail in the context of at least Table 1 and FIGS. 3A-4C.

In some embodiments, such as discussed above in the context of at least Table 1 and FIGS. 3A-4C, the first depth data can include data about an input plurality of points in the environment. Then, determining the first plurality of points can include: generating a filtered plurality of points by filtering the input plurality of points using a bilateral filter; and determining a normal vector for each point in the filtered plurality of points.

In particular of these embodiments, the computing device can include a graphics processing unit (GPU). Then, determining the normal vector for each point in the filtered plurality of points can include determining the normal vector for each point in the filtered plurality of points using the GPU.

At block 1230, the computing device can determine a virtual tool, such as discussed above in detail in the context of at least Table 1 and FIGS. 3A, 5A-5D, 7, 8, and 9. The virtual tool can be specified in terms of a translation component for the virtual tool and a rotation component for the virtual tool. In some embodiments, the translation component can be specified in terms of up to three degrees of freedom, the rotation component can be specified in terms of up to three degrees of freedom distinct from the three degrees of freedom used for the translation component, and thus the virtual tool can be specified in terms of up to six degrees of freedom.

In other embodiments, the translation component can relates to a position of the virtual tool and the rotation component can relate to a rotation of the virtual tool about at least one axis. In still other embodiments, determining the virtual tool can include representing the virtual tool using a plurality of voxels, where each voxel has a voxel size in each of three dimensions, and where the voxel size for each of the three dimensions is a same size.

At block 1240, the computing device can determine a first force vector between the virtual tool and the first plurality of points, such as discussed above in the context of at least Table 1 and FIGS. 3A, 5A-5D, 6, 7, and 10.

In some embodiments, determining the first force vector can include determining a bounding box for the virtual tool based on a projection of the virtual tool onto the first depth image; and determining neighboring points of the first plurality of points, wherein each neighboring point is within the bounding box. In particular of these embodiments, method 1200 can also include determining whether there are zero neighboring points or more than zero neighboring points; and in response to determining that there are zero neighboring points: determining that the virtual tool is in a free-motion state, and moving the virtual tool in a direction based on the translation component and by a distance bounded by a same voxel size.

In other particular of these embodiments, method 1200 can also include: in response to determining that there are more than zero neighboring points: determining a depth for each neighboring point with respect to the virtual tool; determining in-contact neighboring points from the neighboring points, where each in-contact neighboring point has a corresponding depth of zero; determining in-collision neighboring points from the neighboring points, where each in-collision neighboring point has a corresponding depth less than zero; in response to determining that no in-collision neighboring points are determined and to determining at least one in-contact neighboring point is determined: determining a first constrained acceleration for the virtual tool based on the at least one in-contact neighboring point, and moving the virtual tool in a direction based on the first constrained acceleration.

In still other particular of these embodiments, method 1200 can also include: in response to determining that at least one in-collision neighboring point is determined: determining a second constrained acceleration for the virtual tool based on the at least one in-collision neighboring point; and moving the virtual tool in a direction based on the second constrained acceleration.

At block 1250, the computing device can send a first indication of haptic feedback based on the first force vector, such as discussed above in the context of at least Table 1 and FIGS. 3A, 5A-5D, 6, 7, and 10.

In some embodiments, such as discussed above in the context of at least Table 1, method 1200 can include: receiving second depth data about the environment at the computing device, where the second depth data can differ from the first depth data; generating a second plurality of points from the second depth data using the computing device; determining a second force vector between the virtual tool and the second plurality of points using the computing device; and sending, from the computing device, a second indication of haptic feedback based on the second force vector.

In other embodiments, such as discussed above in the context of at least FIG. 3A, the computing device can be configured to communicate with a controllable mechanism. Then, sending the indication of haptic feedback based on the force vector from the computing device can include sending the indication of haptic feedback based on the force vector from the computing device to the controllable mechanism. In these embodiments, method 1200 can also include providing haptic feedback based on the indication of haptic feedback using the controllable mechanism. In particular of these embodiments, the controllable mechanism can include a manipulator configured for surgical operation.

In still other embodiments, such as discussed above in the context of at least FIG. 3A, the first depth data can include first image data and corresponding first depth values. In these embodiments, method 1200 can also include generating a virtual environment based on the first image data and corresponding depth values. In particular of these embodiments, such as discussed above in the context of at least Table 1 and FIGS. 4A-4C, the virtual environment can include a first object. In these embodiments, method 1200 can also include determining a contact between the first object and the virtual tool.

In even other embodiments, method 1200 can also include defining a forbidden region within the environment. Then, determining the first force vector between the virtual tool and the first plurality of points can include inhibiting the virtual tool from moving within the forbidden region. In yet even other embodiments, method 1200 can also include controlling a motion of an object or character within a virtual environment, wherein the virtual environment comprises at least one virtual object and at least one real surface.

Virtual Fixtures for Human/Autonomous Manipulation Tasks

In haptic interaction, an operator can use a physical haptic device to interact with objects in a virtual environment. This virtual environment can consist of representations of physical objects, as captured by sensor data, virtual objects that are entirely computer simulated, or combinations of representations of physical objects and virtual objects. A Haptic Interface Point (or HIP) can be thought of as the position of a 3-DOF end effector in virtual space that matches the position of the haptic device. For 6-DOF end effectors, a virtual tool can represent the end effector. When the user moves the haptic device, the HIP or virtual tool can move accordingly in the virtual environment.

Depth data can be specified as a point cloud can be thought of as an unstructured set of points representing the boundary of physical objects. Depth data can be obtained using stereo cameras, laser scanners or depth cameras in which case the data will be sorted in the image plane. A depth image can augment the depth data with color information. Haptic rendering as described herein can utilize streaming point cloud data represented in depth images for 3 DOF and 6 DOF applications.

Complex telerobotic manipulation tasks require high precision and repetitive actions for which automated systems are highly skilled. However, it also requires critical judgment and decision-making, which is best done by a human operator. Thus, herein is described a combined manipulator system (human+automation) that affords the operator a great amount of freedom but also enhances performance via computer-generated auditory-, visual- and haptic-feedback. The resulting technology will improve the outcome by preventing mistakes and increasing efficiency in manipulation tasks. Rather than using the feedback to solve the task (by forcing the human operator along a pre-defined trajectory) we use the feedback to communicate "intent" of the computer system during sequential operations.

The feedback can be related to "virtual fixtures" added to the virtual environment provided to the operator utilizing haptic feedback to operate effector(s) in a remote environment, such as an operator performing tasks such as remote search and rescue, sensor placement, ordnance placement/removal, remote movement of materiel, and remote construction. The remote environment can be hazardous; e.g., a cleanup site, a search and rescue location, an area with extreme weather conditions, an underwater environment, an outer space environment. Underwater applications of this technology include human-guided surveillance, underwater equipment maintenance and repair, environmental cleanup as well as tasks in the oil and gas industries. In the latter, commercial interest is high, given that expensive equipment is manipulated in time-critical environments, where mistakes can be both fatal and disastrous to the environment.

A virtual fixture can be defined as an overlay of abstract sensory information on a workspace in order to improve the telepresence of a remotely manipulated task. Virtual fixtures can be arbitrary in both appearance and feedback. In some scenarios, virtual fixtures can act as one or more virtual rulers guiding a remote manipulator along a pre-defined path. The operator can be notified of deviations from the path defined by the virtual fixture using audio, visual or haptic feedback in particular. Haptic feedback (force feedback applied to the operator control stick) can be used to guide the operator (and hence the remote end effector) back to the desired path.

Virtual fixtures can also include forbidden-region fixtures and guidance fixtures. As mentioned above, a forbidden-region fixture can define an area represented by the point data where the virtual tool is not permitted to enter; i.e., the forbidden region. A guidance fixture can define an area represented by the point data where the virtual tool is permitted, and perhaps encouraged, to enter.

Virtual fixtures, such as but not limited to forbidden-region fixtures and guidance fixtures, can be specified based on hard constraints that prevent end effector violation of constraints, or soft constraints where undesired motions are resisted but not prevented, using an associated penetration-based penalty cost. An operator can be notified about virtual fixtures using any combination of visual-, auditory-, and haptic feedback. For instance, the haptic feedback can take the form of repelling force feedback, vibrotactile feedback, or rendered as a viscous resistance.

Forbidden-region fixtures and guidance fixtures can be part of a set of standardized virtual fixtures with well-defined visual-, auditory-, and haptic properties. This standard set of virtual fixtures can be used to specify complex manipulation tasks in terms of common manipulation subtasks. Example subtasks include:

Grasping—This virtual fixture will be used to aid the operator in positioning the remote manipulator for a successful grasp of an object of interest.

Rotational manipulation and translational movements—This guidance virtual fixture will be used for valve turning and is important to make sure that no equipment is damaged during operation.

Insertion/Removal—Many operations requires coupling/decoupling of connectors or subsea equipment, so called hot stabbing, and it is therefore important to aid the operator in for instance linear insertions/removals.

Placement—This virtual fixture will aid in operations where equipment needs to be positioned accurately with respect to the environment.

The virtual fixtures can be defined with respect to absolute location(s) in task space and implicitly defined by data from sensors in the remote environment. The virtual fixture can adapt to moving targets and that external disturbances automatically will be rejected. For example, an underwater current can move, and thus disturb, an underwater manipulator. In another example, an external disturbance in a surgical context can occur when a patient moves (or is moved) during a surgical procedure. Many other examples are possible as well.

Haptic feedback can be generated based on data from non-contact sensors such as depth images including data from radar or sonar sensors. Using non-contact sensors, haptic feedback can be generated before contact has been made using 3D images of objects. This can be done before physical contact with obstacles thus avoiding loop delays in operation. In addition, virtual fixtures can be defined around objects depicted in the depth images.

By sensing range and effectively geometries near the manipulator, a guidance fixture can guide the operator to a specific location or region and/or as a forbidden region fixture to block the operator from a specific location or region. Virtual fixtures can be implemented to account for in-motion objects in the environment. Complex tasks, particularly sequential tasks, can benefit from multiple, adaptive virtual fixtures. The virtual fixtures can change as tasks in a series of sequential tasks are completed—for example, a virtual fixture can start as a guidance fixture for guiding operator to a region to perform a task and then, once the task is complete, the virtual fixture can change to a forbidden-region fixture to keep the operator from the region to avoid undoing previously-completed work. The herein-described system is capable of rendering multiple virtual fixtures and switching between them in an intuitive, fluid fashion in real time, in response to the environment and performance needs.

Virtual fixtures can aid the human operator in complex manipulation tasks. These tasks can be planned and carried out using automated and sequential transitioning between virtual fixtures. To perform part or all of the tasks, the operator can use a manipulation system with haptic rendering capabilities. During execution of the tasks, a level of automation can change from manual operation to fully autonomous operation, perhaps with one or more intervening levels of semi-autonomous operations possible. The human operator can adjust the level of automation and also intervene as necessary during autonomous operation. For example, during human-only or mostly-human operation, a flexible guidance fixture can be used that allows for small deviations from a guided path, where the deviations can be subject to guiding but non-constrained feedback, so to provide the operator increased flexibility and control over the situation.

While the operator directs the system, the operator can also respond to system performance and conditions. Auditory, visual, and haptic virtual fixtures can communicate intent of the system to the operator. For example, virtual fixtures can be used to describe basic tasks related to manipulation such as positioning, grasp and screwing/unscrewing tasks. A set of virtual fixtures can be added to the environment to avoid mistakes, such as a forbidden-region fixture, a guidance fixture, a standoff fixture, which is a virtual fixture for maintaining a fixed safety distance between the manipulator and an arbitrary object, and/or a velocity-limited fixture, which is a virtual fixture limiting the maximum velocity of the manipulator.

Figure 13:
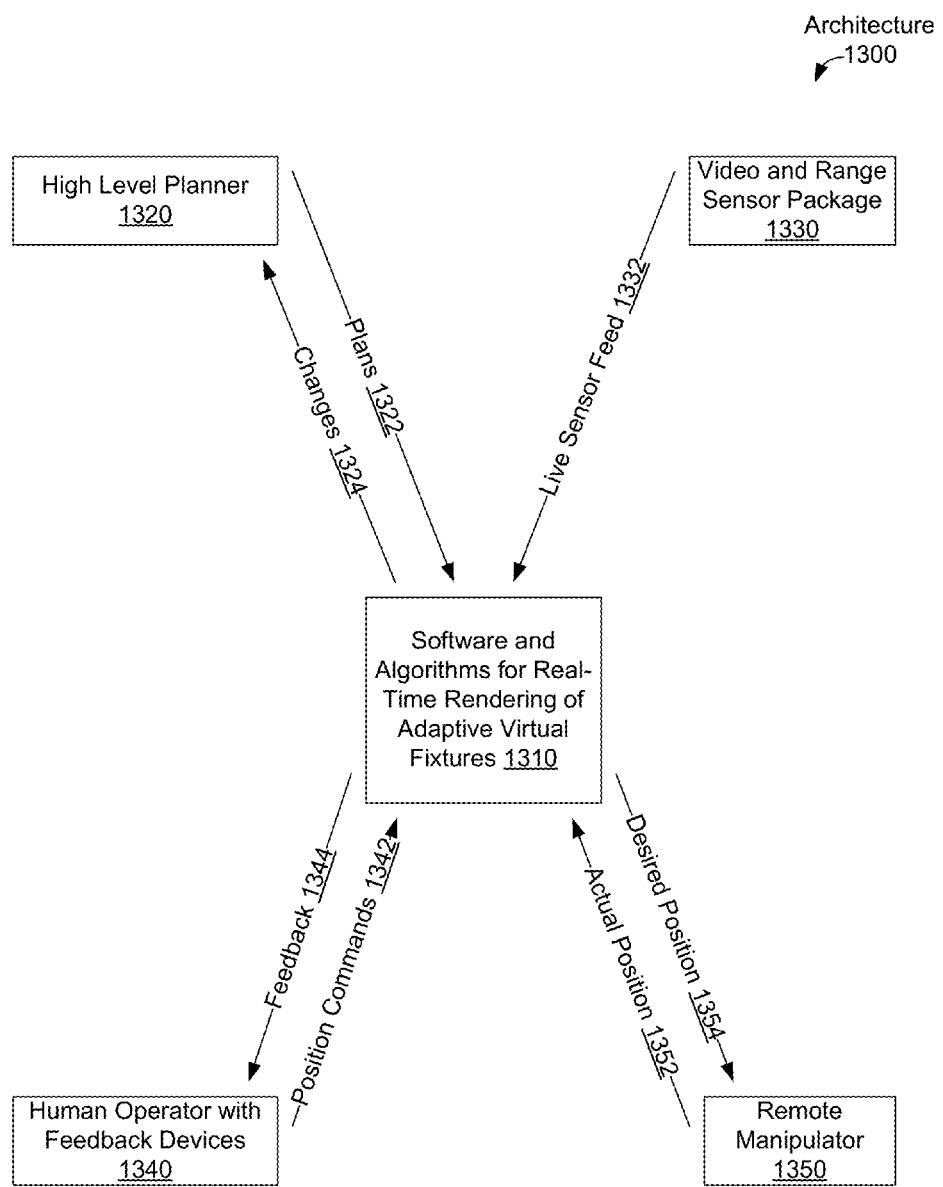
FIG. 13 is a block diagram of an architecture for rendering adaptive virtual fixtures, in accordance with an example embodiment.

FIG. 13 is a block diagram of architecture 1300 for rendering adaptive virtual fixtures, in accordance with an example embodiment. A computing device, such computing device 1120 executing software 1310 can manage the virtual fixtures in a virtual environment based on data from a remote environment. Software 1310 can process and generate the virtual fixtures in real-time based on data in live sensor feed 1332 from video and range sensor package 1330 in the remote environment. Sensor package 1330 can be mounted on a device in the remote environment; e.g., aboard a remote manipulator or robot.

Software 1310 can render virtual fixtures implicitly defined by data in live sensor feed 1332. That is, software 1310 can track and adapt virtual fixtures to changes in the task space; e.g., as tasks are added, completed, updated, and removed; and to changes in the remote environment; e.g., as objects move or change shape. Software 1330 can communicate position commands 1342 from human operator 1340 and/or plans 1322 from high-level planner 1320 to remote manipulator 1350; e.g., as desired position instructions 1354.

Remote manipulator 1350 can report actual position information 1352 to software 1310. Software 1310 can receive actual position information 1352 and data from live sensor feed 1332 to generate feedback 1344 to human operator 1340 about virtual fixtures and perhaps real objects in the remote environment. As software 1310 determines tasks are completed and/or determines changes in the remote environment from data in live sensor feed 1332, software 1310 can provide changes 1324 to plans maintained by high level planner 1320. Further, software 1310 can autonomously provide desired position information 1354 in some circumstances; e.g., positions to be reached while following a guidance feature, to avoid a collision, and/or in response to reaching forbidden region virtual fixture.

Table 2 below illustrates how virtual fixtures can be used in semi-autonomous mode (with both a human and an automated control loop) and in fully autonomous operation. In the latter, system intent is still communicated to the operator using our haptic rendering algorithms, thereby providing an intuitive method for the operator to supervise (but not control) the task. Conversely, the virtual fixtures can be used to communicate the outcome of the operation in manual/human control.

TABLE 2

| Level of Automation | Role of Virtual Fixtures |
|---|---|
| Fully autonomous operation | During fully autonomous operation, virtual fixtures operated by software 1310 can communicate the intent of the autonomously-operating system to the human operator. The intent of the system can be shown with visual cues/displays (e.g., highlighting target position(s) in the workspace), auditory signal(s), and/or haptic feedback. |
| Semi-autonomous operation | During semi-autonomous operation, the system can use the experience and cognition of the human operator linked with the precise spatial awareness of the computer system.<br>Software 1310 can let the operator make decisions within ranges of boundaries determined by likelihood estimates. The human operator can change the ranges of boundaries to effectively modify the level of automation. Controlling ranges of boundaries for decision gives the human operator an intuitive control to the level of automation during semi-autonomous operation.<br>The human operator can make higher-level decisions; i.e. ability to change a planned path within the range of boundaries, or to intervene to avoid impending difficulties. Virtual fixtures can reside on a lower level such that a positioning task always will be made exactly, and such that unintended collisions with the manipulator are prevented, mainly using force feedback. |
| Manual operation | During manual operation, all manipulation tasks can be done manually; e.g., without virtual fixtures. Instead of completely turning off the virtual fixtures, the virtual fixtures can operate in the background without sending feedback to the human operator. Virtual fixtures can communicate the outcome of the manual operator commands to the temporarily deactivated autonomous system. By keeping the autonomous system up to date, the amount of time taken during switchover from manual to (semi-)autonomous operation can be reduced. |

Operator 1340 and/or software 1310 can vary the level of automation. For example, simpler manipulation tasks may be controlled by software 1310 in the fully autonomous mode with operator 1340 providing position commands 1342 that reflect high-level decisions. If an unusual or exceptional event occurs (hence complexity increases), operator 1340 can reduce the level of automation. Combining the experience and skill of a human operator with the spatial awareness of the manipulation system, along with an adjustable autonomy framework, can both increase efficiency and reliability of operations and allow execution more complex tasks than would otherwise be feasible with traditional manual or autonomous solutions.

A complex operation can be planned using standardized virtual fixtures; e.g., the operation can be specified as a sequence or other set of tasks, with each task shaped by virtual fixtures. When defined this way, both the human operator and the autonomous system will be able to readily interpret this plan. Additionally, since the autonomous system also tracks the outcome of each task, procedural compliance can be observed. If important steps are skipped, the human operator can be notified and/or other actions taken; e.g., remote actuators can be put into hibernation or a reduced-performance mode until the correct task is begun. This information can further be used to generate log files that are sparse representations of already completed tasks. Log files can later be used to generate performance statistics and maintenance schedules.

The system can support flexible planning, allowing for some steps to be loosely defined (a necessary feature when operating in un-structured or dynamic environments). For instance, the system might be aware that a lever needs to be pulled, but not which one. When the uncertain part of the plan is reached, the human operator will be asked to guide the system to the right lever using a point-and-click interface.

To best perform the task, the human operator should not perceive that the virtual fixtures are taking over completion the task and that the human is just riding along with an automated system. If the human operator is not sufficiently engaged, the human operator might be overly passive and perhaps reduce focus and performance. For forbidden-region virtual fixtures, preventing passivity is straightforward since forces are only sent when an operator is attempting entry into a forbidden region. That is, haptic feedback can be reasonably expected once the operator realizes the interaction with the forbidden region.

For a guidance virtual fixture, however, the human operator may not always anticipate the activation of a guidance force. Thus, virtual fixtures can use auditory and visual feedback, in addition to haptic to increase the operator's situational awareness during manipulation tasks. This multi-sensory feedback can give the human operator a clear indication when a guidance force is about to be activated. For instance, visual virtual fixture(s) can provide visual indications and/or auditory virtual fixture(s) can emit sounds to indicate regions in task space in which the guidance force will be activated.

On-the-fly definition of virtual fixtures can enhance the high-level architecture of planned operations constructed by standardized virtual fixtures. For this, a combined range and video sensor can be used in the system. The sensor can provide data at a first rate; e.g., at least 30 Hz, and based on the sensor data, force feedback can be generated at a second, faster rate; e.g., at least 1000 Hz. The system can utilize processors, such as general-purpose graphics processing (GPGPU) hardware and a customized parallelized low-level GPU, to process the sensor data at least the first rate and generate force feedback at the second rate.

Figure 14:
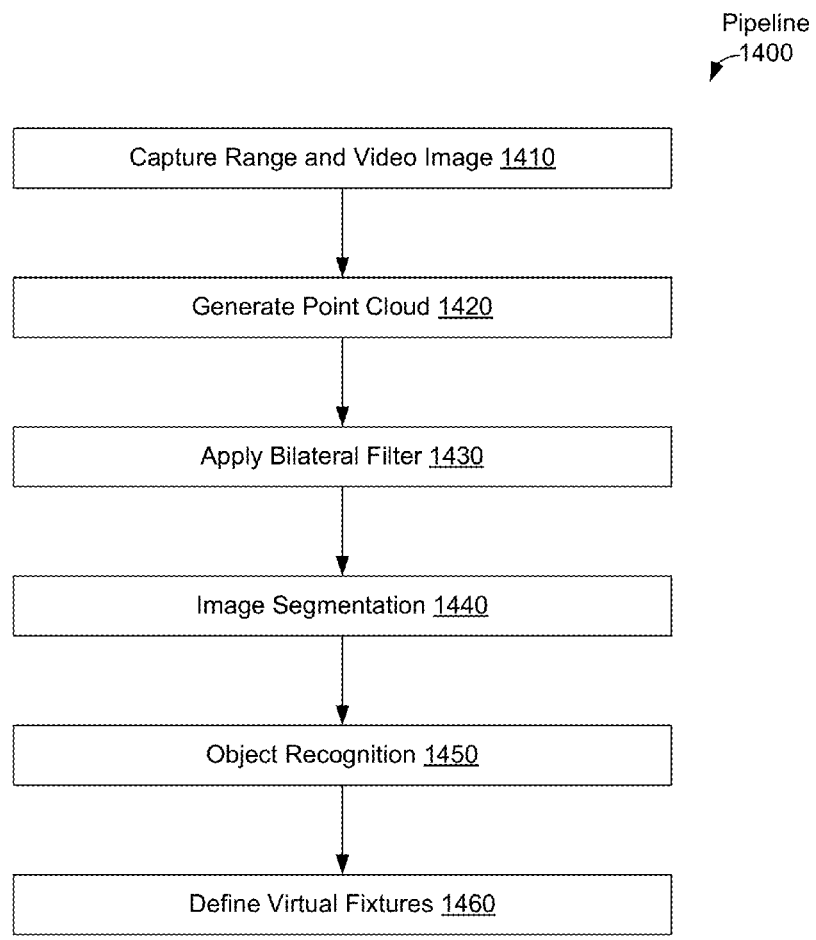
FIG. 14 is a block diagram of a pipeline for parallel processing and generation of virtual fixtures, in accordance with an example embodiment.

FIG. 14 is a block diagram of pipeline 1400 for parallel processing and generation of virtual fixtures, in accordance with an example embodiment. Pipeline 1400 can begin at block 1410, where range and video image data can be captured. For example, a computing device carrying out operations of pipeline 1400 can receive one or more depth image at block 1410, use cameras and/or sensors to obtain range and video image data, or otherwise obtain range (depth) and video image data.

At block 1420, a point cloud can be generated from the range and video image data. The point cloud can be a collection of points in a frame of reference, such as a collection of Cartesian points in a three-dimensional space where the points correspond to objects whose images are captured at block 1410. In some embodiments, other data structures, such as depth images, can be utilized and/or generated at blocks 1410 and 1420.

At block 1430, a bilateral filter can be applied. Bilateral filters can be used to smooth data within the point cloud by weighted a value associated with point; e.g., a depth value, with a weighted average of values from nearby points. For example, the points can be weighted using a Gaussian kernel as a function of Euclidean distances in a Cartesian frame. In some embodiments, block 1430 can be omitted. In other embodiments, other filters can be applied instead of or along with the bilateral filter.

In some embodiments, normal values can be determined for points in the point cloud. For example, pipeline 1400 can be utilized to carry out part or the entire example haptic interaction algorithm for 6-DOF haptic rendering discussed above in the context of Table 1.

At block 1440, the image obtained at block 1410 can be segmented. That is, each pixel in the video image can be assigned a label. Each label can represent visual characteristics; e.g., a range of colors, a location on a boundary (or within the interior) of an object, etc. Two pixels assigned to the same label have the same visual characteristics.

At block 1450, objects can be recognized from the segmented image. In some embodiments, recognized objects can be associated with collections of points within the point cloud. For example, suppose an apple is recognized in the segmented image and that the apple is depicted in a set of pixels SP of the segmented image. Let SPt be the set of points in the point cloud associated with pixels SP. Since SP is associated with the apple, then SPt can be associated with the apple as well.

At block 1460, virtual fixtures can be defined. The virtual fixtures can be defined with respect to the object(s) recognized at block 1450. To continue the example from block 1450, a virtual fixture VFa can be associated with SP and SPt, and thus be associated with the recognized apple. Then, if the apple moves in a later image captured at block 1410, the apple can be re-recognized in the later image at block 1450, and virtual fixture VFa reassociated with the moved apple. Thus, virtual fixtures can be dynamically associated at block 1460 with objects in an environment captured in the range and video image data obtained at block 1410 and recognized at block 1450.

In other embodiments, the virtual fixtures can be specified in terms of geometry in a remote environment and/or in a virtual environment. For example, a virtual object can be introduced into the virtual environment; e.g., a virtual cube or sphere. Then, a virtual fixture can be associated with the virtual object. As another example, the virtual fixture can be defined with respect to a geometric region, volume, or other entity in either the remote or virtual environment without respect to another object. Other examples of pipeline 1400 are possible as well.

In some scenarios, the captured range and video image data is insufficient; e.g., in cases of significant measurement noise or sensor occlusion. Measurement noise may be suppressed using filtering such as discussed above with respect to block 1430, To account for sensor occlusion, occlusion by a remote manipulator can be predicted based on detailed models of the remote manipulator, kinematic equations, and data about manipulator positioning. Then, sensor data can be rejected that correspond to regions predicted to be occluded by the remote manipulator. In the rejected regions, sensor data can be interpolated using previously captured data. Further, by predicting a position of the remote manipulator for occlusion, the predicted position can also be used to verify the state of the manipulator during runtime, and so enhance operational safety.

Figure 15:
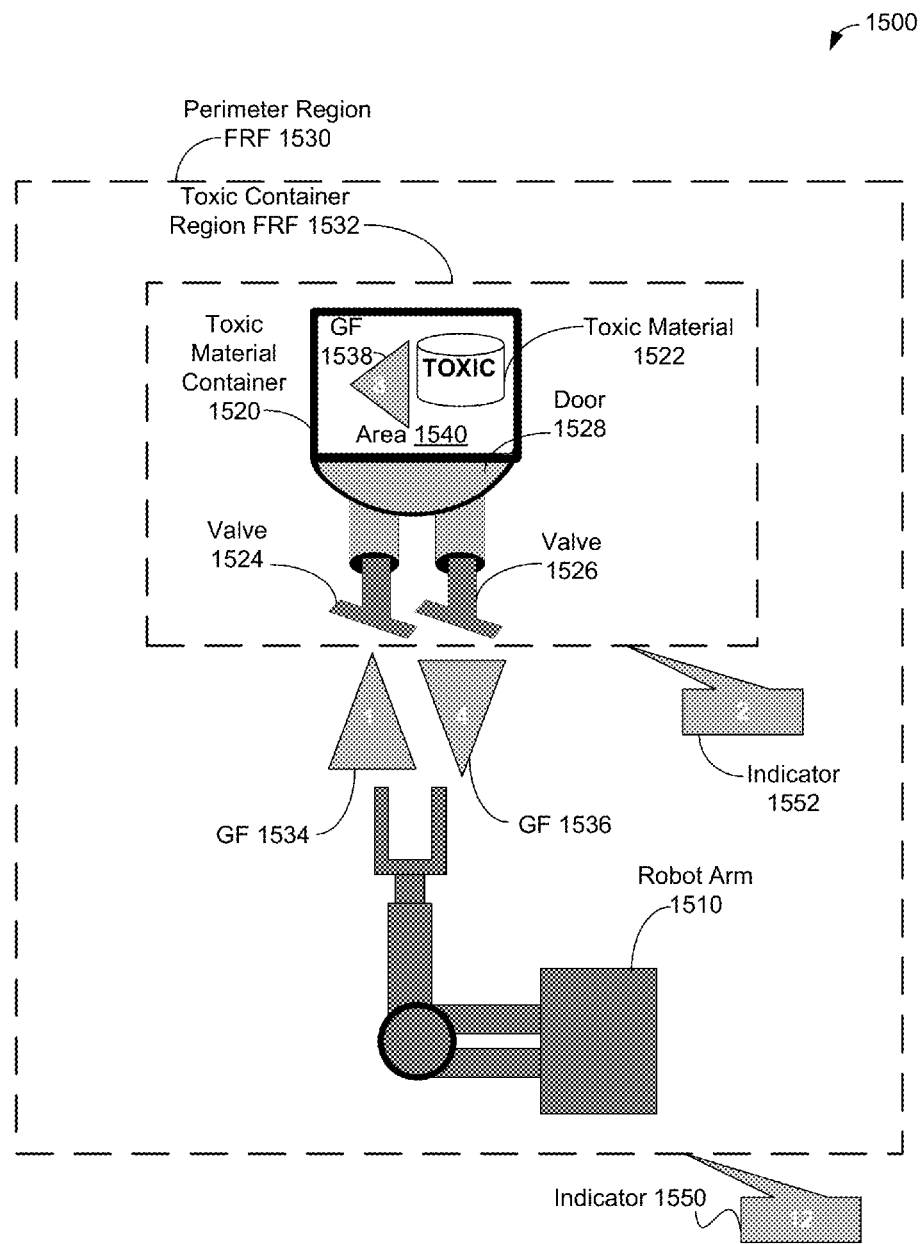
FIG. 15 depicts an environment with a robot arm and multiple virtual fixtures, in accordance with an example embodiment.

FIG. 15 depicts an environment 1500 with a robot arm and multiple virtual fixtures, including forbidden-region fixtures (FRFs) 1530, 1532 and guidance fixtures (GFs) 1534, 1536 in accordance with an example embodiment. Environment 1500 is a virtual environment containing representations of real objects, such as robot arm 1510 and toxic material container, and representations of virtual objects, such as virtual fixtures 1530, 1532, 1534, 1536, 1538.

In some embodiments, some or all of virtual fixtures 1530, 1532, 1534, 1536, 1538 can be associated with a task list. Table 3 below shows an example task list related to environment 1500 for robot arm 1510, where the task list is associated with virtual fixtures 1530, 1532, 1534, 1536, 1538 as also shown in Table 3.

TABLE 3

| Task List | FRF 1530 | FRF 1532 | GF 1534 | GF 1536 | GF 1538 |
| --- | --- | --- | --- | --- | --- |
| 1. Go to Valve 1524 | Initially FRF. Enable entry/exit based on valid authorization | Initially FRF. Enable entry/exit based on valid authorization | Use GF to move toward valve 1524 | Initially guide away from valve 1526 | Initially guide away from material 1522 |
| 2. Obtain Authorization to Enter Region 1532 | | If valid authorization provided (during task), deactivate FRF | | | |
| 3. Turn Valve 1524 | | | | Upon completion of task, change to guide away from valve 1524 | Upon completion of task, change to guide toward valve 1526 |

TABLE 3-continued

| Task List | FRF 1530 | FRF 1532 | GF 1534 | GF 1536 | GF 1538 |
|---|---|---|---|---|---|
| 4. Go to Valve 1526 | | | | Use GF to move toward valve 1526 | |
| 5. Turn Valve 1526 | | | | Upon completion of task, change to guide away from valve 1526 | |
| 6. Open Door 1528 | Door Handle/path to open door may be controlled by guidance fixture not shown in FIG. 15. This fixture may be activated by completion of Task 5 and/or deactivated by completion of Task 6. | | | | |
| 7. Enter Area 1530 | Pathway to area 1534 can be provided by guidance fixture not shown in FIG. 15. This fixture may be activated by completion of Task 6. | | | | Upon completion of task, change to guide toward material 1522 |
| 8. Go to Toxic Material 1522 | | | | | Use GF to move toward material 1522 |
| 9. Get Toxic Material 1522 | | | | | Upon completion of task, GF can change to guide away from material 1522 |
| 10. Remove Toxic Material from Region 1532 | | | | | Use GF to move away from material 1522. Other GFs can be activated. |
| 11. Wait for Transport from outside Region 1530 | | | | | |
| 12. Put Toxic Material on Transport | Guidance features not shown in FIG. 15 can guide robot arm 1510 toward transport. In some embodiments, part of guidance feature 1530 can be deactivated to let robot arm 1510 and/or transport work together. | | | | |
| 13. Close Door 1528 | Guidance features not shown in FIG. 15 may guide robot arm 1510 to door and to close door (similar to those for Task 6). | | | | |
| 14. Leave Perimeter Region 1530 | Deactivate FRF until robot arm 1510 leaves region 1530. | Activate FRF once robot arm leaves region 1532 | | | |

Each of virtual fixtures 1530, 1532, 1534, 1536, 1538, is shown in FIG. 15 associated with a number. For example, virtual fixtures 1530 and 1532 have associated respective indicators 1550 and 1552 showing respective numbers 2 and 12, while each of virtual fixtures 1534, 1536, 1538 is shown displaying respective numbers 1, 4, and 8. In the environment shown in FIG. 15, where tasks in the task list of Table 3 have not yet begun, each number correspond to the next task that the virtual fixture is associated with. So, virtual fixture 1534 is associated with Task 1 of the task list, virtual fixture 1532 is associated with Task 2, and so on. The indicator can be updated as tasks complete; e.g., upon completion of Task 1, the virtual fixture indicator for virtual fixture 1534 can be updated to refer to Task 3, which is the succeeding task for that virtual fixture. In some embodiments, an indicator of a virtual fixture can indicate multiple tasks associated with the virtual fixture; e.g., the next N tasks, with N>1, or all tasks referring to the virtual fixture. In other embodiments, upon completion of the last task involving a virtual fixture, an indicator for the virtual fixture can change to "Complete" or a similar indication of completion. In still other embodiments, upon completion of the last task involving a virtual fixture, the virtual fixture can be removed from environment 1500.

In another scenario, consider a manipulation task where two valves need to be turned, such as valves 1524 and 1526. In this scenario, the order in which the valves are turned is irrelevant. The human operator can see valves 1524, 1526 on a display with both highlighted as valid targets. In addition to the valves the operator also sees virtual cones; e.g., guidance fixtures 1534 and 1536, extending out from each handle. Since the computer system providing environment 1500 cannot be sure which valve the human operator will approach first, no force feedback is given. Instead, if the operator commands the manipulator into the cone extending out valve 1524, force feedback can be automatically activated to guide the manipulator into a perfect configuration for a valve turn. That is, the human operator makes the high level decision and the computer system makes sure that it is being executed with high accuracy. To the operator the whole procedure will feel effortless, just as if the manipulator 'just happened' to slide into the right configuration by accident. Similar user interfaces exist in many document processors, where the user drags a figure to roughly the right position in the document and the software automatically aligns it with the margins.

Virtual fixtures can be programmatically controlled. For example, task-management software can control one or more associated virtual fixtures. In some embodiments, the task-management software can be part of software 1310 discussed above in the context of FIG. 13.

The task-management software can include software that manages tasks on a task list with associated virtual fixtures such as shown in Table 3. The task-management software can allow the operator to define a task list, define virtual fixtures as needed for the task list, define tasks on the task list, and then aid the operator and associated remote devices; e.g., robot arm 1510 of FIG. 15, to carry out the tasks. The task-management software can ensure that tasks on the task list are carried out in order. In some embodiments, a task can be defined in terms of multiple operators acting in parallel.

The task-management software can use the task list in combination with real-time sensor data to automatically transition between the different virtual fixtures, such as the transition between grasping and turning a valve. In cases where multiple choices are possible, the task-management software will have the ability to let the operator decide while in semi-autonomous levels of automation. In cases when no operator is present and/or in a fully autonomous level of operation, the task-management software can use a number of techniques to make a decision, such as conditional probabilities and maximum likelihood votes. The task-management software can avoid undesirable transients that can arise from virtual fixture transitions as well as from task state changes by careful matching of terminal and initial conditions of successive control epochs as well as enforcement of protective constraints on control states and outputs.

The task-management software, in addition to serving as an interface and control system, can constantly monitor operations toward task completion and continually tracking of operation outcomes with associated likelihoods. The task-management software can adaptively generate and transition between virtual fixtures identified for a given task. Although the task-management software can execute the transitions between virtual fixtures autonomously, autonomous operation is not always desirable. Rather, a level of automation can be modified, either by the computer system or by the operator as discussed above in the context of FIG. 13 and Table 2.

As another example, some or all virtual fixtures in a virtual environment can be associated with a script or other software that controls part or all of the operation of the virtual fixture. The script can include instructions, such as but not limited to instructions that can operate based on conditions of the virtual fixture; e.g., a type of virtual fixture (forbidden-region fixture, guidance fixture), conditions in the environment; e.g., time, temperature, weather conditions, water currents, wind condition, chemical conditions, biological conditions, nuclear conditions, sensory input related to conditions in the environment, task lists and/or tasks, and/or other conditions. The instructions can change the virtual fixture, perhaps based on a condition in the environment.

For example, a forbidden-region fixture that allows entry to a forbidden region to a device D if proper authorization is provided by D at time of entry can have a virtual-fixture script such as shown in Table 4 below.

TABLE 4

```
ID = myID( );
send_authentication_request( );
R = get_authentication_response( );
If (valid_entry(ID, R)) then
    Open(ID);
```

The virtual-fixture script can be invoked when the entry to the forbidden region associated with the virtual fixture is sought, when an object comes in contact with the virtual fixture, or at some other time. The virtual-fixture script first assigns an identifier "ID" to the virtual fixture using a myID( ) function—in some embodiments, this can be performed prior to script execution. Then, an authentication request can be sent and a response "R" to the authentication request received. The virtual-fixture script then determines if R provides valid entry to the virtual fixture using the valid entry( ) function—if R does provide valid entry to the forbidden region associated with the virtual fixture, then the virtual fixture is opened using the open( ) function. Virtual-fixture scripts can have other characteristics; e.g., a virtual-fixture script can be written in other computer languages, can utilize many other functions, can be compiled and/or interpreted, and/or can perform other operations. Many virtual-fixture scripts are possible as well.

Figure 16:
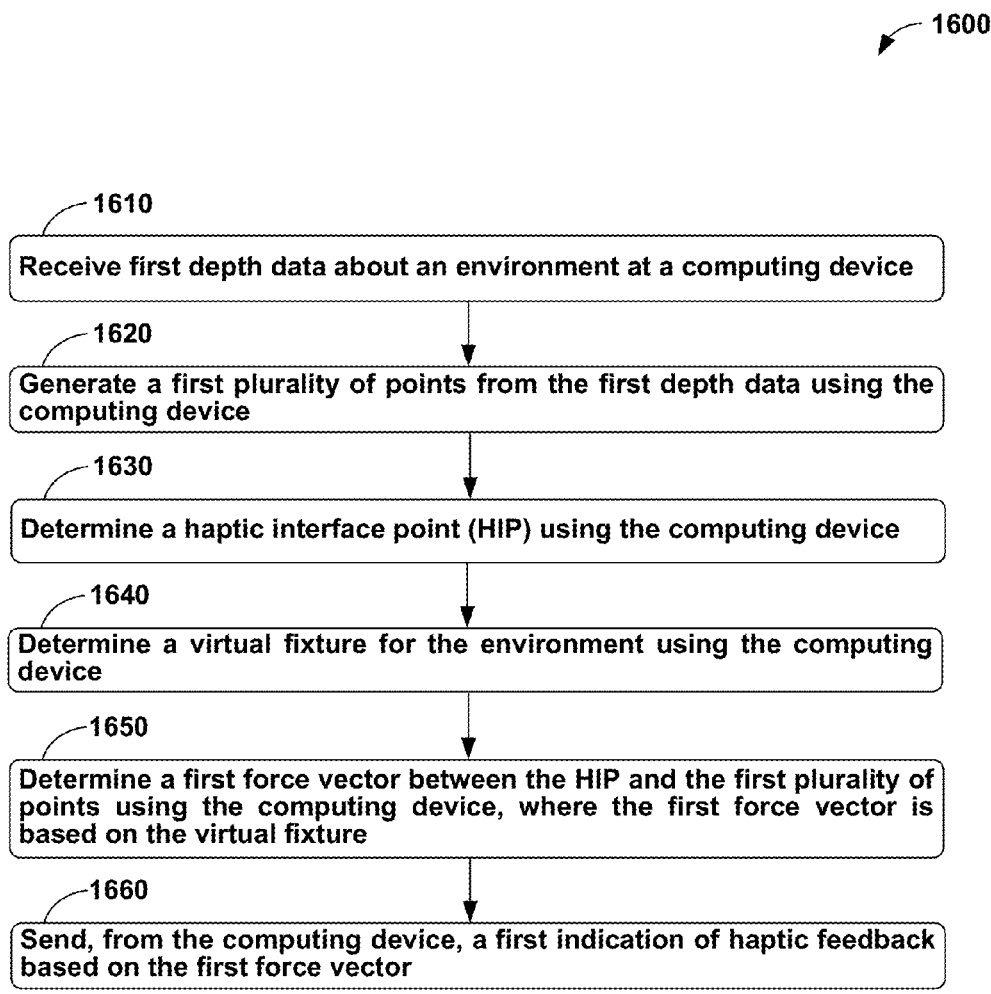
FIG. 16 is a flowchart of another method, in accordance with an example embodiment.

FIG. 16 is a flowchart of method 1600, in accordance with an example embodiment. Method 1600 can begin at block 1610, where a computing device can receive first depth data about an environment. At block 1620, the computing device can generate a first plurality of points from the first depth data. At block 1630, the computing device can determine a haptic interface point.

At block 1640, the computing device can define a virtual fixture for the environment. In some embodiments, wherein determining the virtual fixture for the environment can include: determining one or more objects in the environment from the first depth data; determining a first object of the one or more objects, the object having a first location in the environment; and associating the virtual fixture with the first object and the first location.

In other embodiments, the virtual fixture is at least one fixture selected from the group of fixtures consisting of a forbidden-region fixture and a guidance fixture. In particular of the other embodiments, the virtual fixture can include a forbidden-region fixture. Then, determining the first force vector can include: determining an initial force vector between the HIP and the first plurality of points; determining whether the HIP is within a forbidden region defined by the forbidden-region fixture; and in response to determining that the HIP is within the forbidden region: generating a forbidden-region-force vector away from the forbidden region, and determining the first force vector based on the initial force vector and the forbidden-region-force vector.

In other particular of the other embodiments, the virtual fixture can include a guidance fixture. Then, determining the first force vector comprises: determining an initial force vector between the HIP and the first plurality of points; determining whether the HIP is within a guidance region defined by the guidance fixture, wherein the guidance region comprises a target; and in response to determining that the HIP is within the guidance region: generating a guidance-region-force vector toward the target; and determining the first force vector based on the initial force vector and the guidance-region-force vector.

In still other embodiments, defining the virtual fixture for the environment can include: determining one or more instructions related to the virtual fixture and defining the virtual fixture based on the one or more instructions. In particular of the still other embodiments, the one or more instructions can be configured to change the virtual fixture based on a condition in the environment. In more particular of the still other embodiments, the condition in the environment comprises a condition selected from the group of conditions consisting of a time condition, a temperature condition, a weather condition, a water-current condition, a wind condition, a chemical condition, a biological condition, and a nuclear condition.

At block 1650, the computing device can determine a first force vector between the haptic interface point and the first plurality of points. The first force vector is based on the virtual fixture. In some embodiments, the virtual fixture can include a standoff fixture. The standoff fixture can define a target and a safety region. The safety region can be associated with the target. Then, determining the first force vector can include: determining an initial force vector between the HIP and the first plurality of points; determining whether the HIP is within the safety region; and in response to determining that the HIP is within the safety region: generating a safety-region-force vector away from the target, and determining the first force vector based on the initial force vector and the safety-region-force vector.

In other embodiments, the HIP can have a velocity. The virtual fixture can include a velocity-limited fixture. The velocity-limited fixture can define a velocity-limited region and a maximum velocity. Then, determining the first force vector comprises: determining an initial force vector between the HIP and the first plurality of points; determining whether the HIP is within the velocity-limited region; in response to determining that the HIP is within the velocity-limited region: determining whether the velocity of the HIP exceeds the maximum velocity, and in response to the velocity of the HIP exceeding the maximum velocity, determining a velocity-limiting vector opposing the velocity of the HIP, and determining the first force vector based on the initial force vector and the velocity-limiting vector.

At block 1660, the computing device can send a first indication of haptic feedback based on the first force vector. In some embodiments, method 1600 can further include: receiving second depth data about the environment at the computing device, where the second depth data differs from the first depth data; determining one or more objects in the environment from the second depth data; determining whether the one or more objects includes the first object; and in response to determining that the one or more objects include the first object: determining a second location in the environment for the first object, and associating the virtual fixture with the first object and the second location.

In other embodiments, the environment can include a virtual tool associated with the HIP. The virtual tool can be defined in terms of a tool-translation component and a tool-rotation component. The target can be configured to be defined in terms of a target-translation component and a target-rotation component. Then, method 1600 can further include: in response to determining that the HIP is within the guidance region, aligning the tool-rotation component with the target-rotation component.

In still other embodiments, method 1600 can further include: determining a task list that can be associated with a plurality of tasks to be performed in the environment, where the task list comprises a first task. Then, determining the virtual fixture can include determining the virtual fixture based on the task list. In particular of these embodiments, determining the virtual fixture based on the task list can include: determining the virtual fixture initially to be a first virtual fixture; determining whether the first task is completed; and in response to determining that the first task is completed, changing the first virtual fixture to a second virtual fixture, wherein the first virtual fixture and the second virtual fixture differ.

In some particular of these embodiments, the first virtual fixture can be a guidance fixture and the second virtual fixture can be a forbidden-region fixture. In other particular of these embodiments, the first virtual fixture can be a forbidden-region fixture and wherein the second virtual fixture can be a guidance fixture. In other particular of these embodiments, the task list can further include a second task. The virtual fixture can include a first virtual fixture having a first type of virtual fixture. Then, determining the virtual fixture based on the task list can include: determining whether the first task is completed; in response to determining that the first task is completed, changing the first type of virtual fixture to a second type of virtual fixture, wherein the first type of virtual fixture and the second type of virtual fixture differ; determining whether the second task is completed; and in response to determining that the second task is completed, changing the second type of virtual fixture to a third type of virtual fixture, wherein the second type of virtual fixture and the third type of virtual fixture differ.

In some of the other particular of these embodiments, the first type of virtual fixture can be a forbidden-region type of virtual fixture, the second type of virtual fixture can be a guidance-region type of virtual fixture, and wherein the third type of virtual fixture can be the forbidden-region type of virtual fixture.

Haptic Rendering Related to Underwater Tasks

The herein-described techniques for 3DOF and 6DOF dynamic haptic rendering can be utilized to carry out tasks underwater. Operations in the deep sea, or hazardous marine environments, typically require manipulation from remotely operated vehicles (ROVs). For example, haptic rendering can be used in the context of an omnidirectional mobile robot with underwater grippers; e.g., robot 1000 discussed above in the context of at least FIG. 10. These underwater tasks can include tasks for search and rescue, underwater infrastructure maintenance, repair, mining, military operations, and waste cleanup.

Subsea manipulation is a challenging task, and one that is necessary in a number of applications. Examples include the construction of cabled ocean observatories, biological studies of hydrothermal vent colonies, oil and gas operations, subsea mining, and other activities that require precise movement on the seafloor. In these applications, a human operator's perception is important, especially in the presence of disturbances due to currents, low visibility situations, or other scenarios that require adaptation. Another difficulty in performing manipulation tasks with remote robots arises in making precise motions and interactions in the presence of dynamically changing environments. These include objects or structures that must be avoided or protected. These objects can be moving, and possibly changing in size. For example, in underwater manipulation for repair (e.g., oil platforms) or for biological sampling, precision manipulation is required despite disturbances from water flow and turbulence.

Underwater tasks can involve manipulation in the vicinity of sensitive or delicate structures. Visual features, such as scaling and tremor dampening can improve performance. However, operator error, communication delay and limited visual feedback can cause a robot to be accidentally driven into sensitive structures and result in irreparable damage. The problem is further amplified in the absence of haptic feedback to the operator. If the contact is not visually detected by the operator, a resulting collision can cause serious damage.

Consider, for example, the common task of mating electrical connections underwater. In principle this is a simple maneuver; however, operators often find it difficult to successfully mate connections using underwater manipulators, such as robot arms including the ARM 5E MINI five-function electric manipulator configured for subsea use. At best, this difficulty results in excessively long duration operations that drive up the cost of subsea operations. At worst, hardware is destroyed, often requiring expensive replacements. Further, operational costs for ROVs can be expensive; e.g., $1 per second or more. Thus, there is great incentive to maximize the efficiency and capability of human/co-robot manipulation tasks in subsea environments.

An underwater depth-enabled camera can be used provide depth images for 3DOF and 6DOF haptic rendering to carry out underwater tasks. The depth images can provide haptic feedback to a human operator, giving with a sense of touch along with a visual representation objects seen by the camera. For example, a human operator can use a tele-operated robotic device equipped with the underwater depth-enabled camera to direct robotic removal of ordnance from lake, river or sea bottoms. An added feature of the herein-described techniques is prevention of robot end effector contact with undesirable locations through imposition of virtual fixtures, such as forbidden-region fixtures.

In some embodiments, the depth-enabled camera can be used in combination with a metal detector or metal detector array. This combination of devices can provide a human tele-operator with information about both depth (distance to target) and metal profile(s) within the area of operation. The metal detector (array) can be mounted on an underwater craft near manipulator(s), such as robotic arms, to allow 2D or 3D metal profiles to be mapped without using a visual or acoustical detector. An array of small metal detectors can be configured in a cross pattern, arranged around the camera system to allow 2D metal profiling data to be taken simultaneously with the image capture. The metal profile will be generated from the array moving across the area while scanning. An alternate metal detector design is to obtain the metal profile system using a phase array design where radiation pattern of the B field can be shifted by adjusting the phase difference between driving coils inside each metal sensor.

In an example system, a depth-enabled camera and metal detector array camera optimized for reconnaissance and surveying can be placed in a Sea Ray-like ROV operable from a surface craft, such as a barge. The ROV can be linked to the surface craft by a tether, ensuring ROV recovery as well as uninterruptible power and data lines. The ROV can be equipped with additional video cameras and lights in addition to the depth-enabled camera and metal detector array. The ROV can provide the data necessary to construct a complete 3D picture of what is ahead of the surface craft and update a 3D underwater map in real time.

Providing haptic feedback from underwater sensors to an operator at the surface has the potential to transform subsea manipulation capability. Virtual fixtures will allow manipulators to precisely maneuver in sensitive environments where contact should not be made with surrounding objects or structures. Biological studies of animal colonies around hydrothermal vents could benefit greatly from such a capability—allowing scientists to carefully gather data with unprecedented resolution and proximity to sensitive organisms. Common tasks such as connector mating between instruments can be carried out very efficiently by creating guidance fixture near male and female connectors. Thus, time, expense, and equipment can be saved, and the environment preserved using the herein-described haptic feedback techniques to perform underwater tasks.

Figure 17:
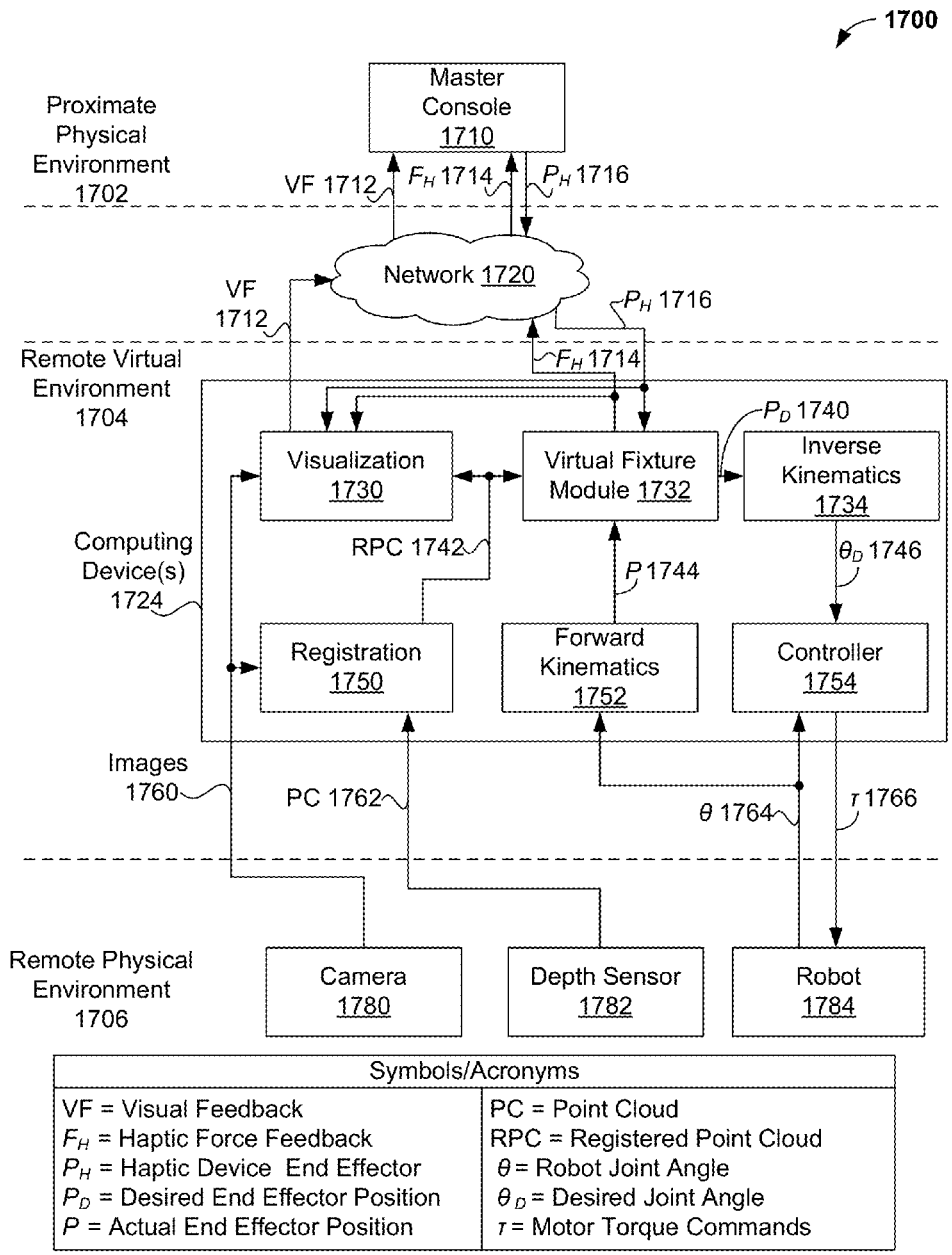
FIG. 17 is a block diagram of a system for a proximate operator to perform tasks in a remote physical environment, in accordance with an example embodiment.

FIG. 17 is a block diagram of system 1700, in accordance with an example embodiment. System 1700 is shown with respect to three environments: proximate physical environment 1702, remote virtual environment 1704, and representing remote physical environment 1706. As one of many possible examples, remote physical environment 1706 can be an underwater environment.

In proximate physical environment 1702, master console 1710 can be, or include, a computing device configured to enable a human operator (not shown in FIG. 17) to interact with remote physical environment 1706. For example, master console 1710 can have a computing device, haptic interface device, and display configured to provide visualizations, such as computing device 320b, haptic interface device 316, display 312, and visualization 318 discussed above with respect to FIG. 3A.

Master console 1710 can communicate with network 1720. Figure 1700 shows that master console 1710 can receive feedback from network 1720, such as visual feedback (VF) 1712 and haptic force feedback 1714 ($F_H$), and can send commands, such as commands with a haptic device, or instructed, end effector position 1716 ($P_H$) of a remotely-controlled device in remote physical environment 1706, such as robot 1784.

Network 1720 can connect computer devices in proximate physical environment 1702 and remote physical environment 1706; e.g., connect master console 1710 with computing device 1720. For example, network 1720 can have some or all of the functionality of network 310 of FIG. 3A. FIG. 17 illustrates that network 1720 can communicate data, including but not limited to, visual feedback 1712, haptic force feedback 1714, and haptic device position 1716, between proximate physical environment 1702 and remote physical environment 1706.

Remote virtual environment 1704 can include computing device(s) 1724 configured to communicate with network 1720 and remote physical environment 1706. For example, computing device(s) 1724 can have some or all of the functionality of computing device 320a of FIG. 3A. FIG. 17 indicates that computing device(s) 1724 can include visualization module 1730, virtual fixture module 1732, inverse kinematics module 1734, registration module 1750, forward kinematics module 1752, and controller module 1754. Each or all of modules 1730, 1732, 1734, 1750, 1752, 1754 can be or comprise software executable on processor(s) of computing device(s) 1724.

FIG. 17 shows that remote physical environment 1706 can include sensors, such as camera 1780 and depth sensor 1782, and robot 1784. For examples, camera 1780 can be or include one or more of depth enabled cameras 346a, 346b, 346c, 346d shown in FIG. 3A and robot 1784 can be or include remote controlled device 336 also shown in FIG. 3A. In some embodiments, camera 1780 can include depth sensor 1782 and be configured for underwater use; e.g., camera 1800 discussed below in the context of FIGS. 18A and 18B.

In operation, camera 1780 can capture light within remote physical environment 1706 and generate images 1760. At the same time, depth sensor 1782 can capture a 3D depth map of remote physical environment 1706 in the form of point cloud 1782 obtain depth information about and generate point cloud (PC) 1762. Robot 1784 can obtain data about actual robot joint angle(s) for actuator(s), effector(s), robot arm(s), and/or other component(s) of robot 1784. The data about actual robot joint angle(s) is shown in FIG. 17 as robot joint angle (A) 1764. Images 1760, point cloud 1762, and robot joint angle 1764 can be communicated to computing device 1724 in remote virtual environment 1704.

More specifically, FIG. 17 shows that images 1760 are communicated to registration module 1750 and visualization module 1730, point cloud 1762 is communicated to registration module 1750, and robot joint angle 1764 is communicated to forward kinematics module 1752 and controller module 1754.

For point cloud 1762, point cloud 1762 can be registered in the robot frame to aid processing within system 1700. FIG. 17 shows that registration module 1750 registers point cloud 1762 to generate registered point cloud (RPC) 1742. To register point cloud 1762, registration module 1750 can generate a transformation between point cloud 1762 and a point of view of robot 1784 based on image(s) 1760. Registered point cloud 1742 can then be communicated from registration module 1750 to visualization module 1730 and virtual fixture module 1732.

Visualization module 1730 can use visual data from image(s) 1712 and depth data from registered point cloud 1742 to generate visual feedback 1712. Visual feedback 1712 can also include visual information related to haptic force feedback 1714; i.e., if haptic force feedback 1714 indicates a force due to collision with an object, then corresponding visual feedback; e.g., a visual collision alert or other indication of collision, can be added to visual feedback 1712. Similarly, end effector position commands, such as end effector position 1716, can be used in visual feedback; e.g., if end effector position 1716 indicates that an end effector moves in a direction D, then visual feedback 1712 can show corresponding movement of (a visualization of) an end effector of robot 1784.

Forward kinematics module 1752 can convert robot joint angle 1764 to end effector coordinates (P) 1744. Virtual fixture module 1732 can employ registered point cloud 1742, end effector coordinates 1744, and end effector position 1716 to compute and provide haptic force feedback 1714 to the operator via master console 1710 and network 1720. Virtual fixture module 1732 also can compute and communicate desired end effector position ($P_D$) 1740 to inverse kinematics module 1734. Inverse kinematics module 1734 can convert desired end effector position 1740 to desired joint angle(s) ($\theta_D$) 1746, which in turn can be converted into motor torque commands ($\tau$) 1766 by controller module 1754. Upon reception of motor torque commands 1766, robot 1784 can move motor(s) in accord with the received commands 1766. In some embodiments, robot 1784 can have multiple controllable components; e.g., have multiple arms and/or end effectors. In still other embodiments, robot 1784 can be mobile and move in accord with commands provided from master console 1710. In these embodiments, motor torque commands 1766 can be generated to move multiple components of robot 1784 and/or to move robot 1784 itself. In still other embodiments, system 1700 can use multiple cameras 1780, depth sensors 1784, and/or robots 1784 in remote physical environment 1706, which can be controlled by one or more operators at master console 1710 and using information provided by computing device(s). Other configurations of system 1700 are possible.

Depth Cameras for Underwater Virtual Fixtures

Figure 18A:
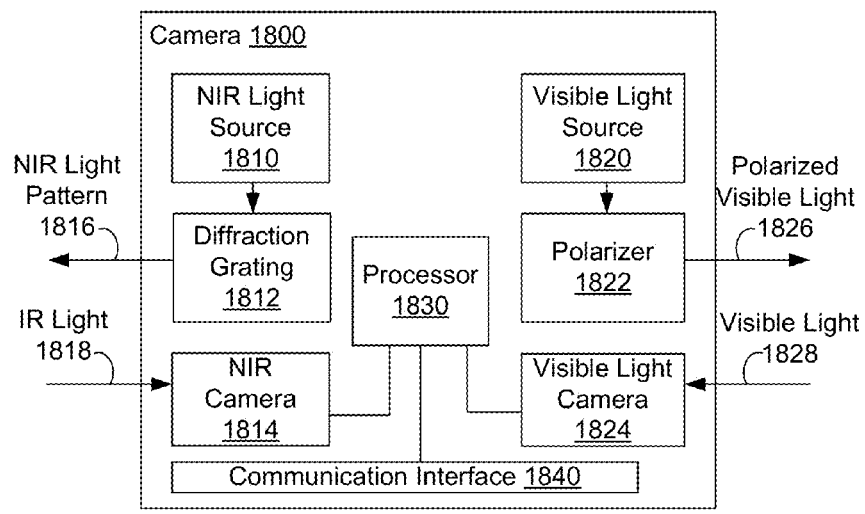
FIG. 18A is a block diagram of a camera configured to provide images for underwater haptic rendering, in accordance with an example embodiment.

FIG. 18A is a block diagram of camera 1800 configured to provide images for underwater haptic rendering, in accordance with an example embodiment. Camera 1800 is a video camera built for underwater use and configured to capture depth data and light and provide the captured delight. The captured depth data and light can be provided as images, such as depth images that can be used to generate haptic feedback and virtual fixtures. In some embodiments, camera 1800 can provide frames at VGA resolution (720×900 pixels) at a frame rate of 30 frames/second in RGB plus Depth (RGBD) format. Camera 1800 can determine depth displacement based on variations of the geometry of a projected pseudo-random pattern of near-infrared (NIR) light. Generally, visible light can be light with wavelength(s) in a visible-light range between 400 and 700 nanometers (nm), and near-infrared light can be light with wavelength(s) in a near-infrared range between 700 and 2000 nm.

FIG. 18A shows that camera 1800 includes near-infrared light source 1810, diffraction grating 1812, infrared camera 1814, visible light source 1820, polarizer 1822, visible light camera 1824, processor 1830, and communication interface 1840. Near-infrared light source 1810 can generate infrared light using one or more light-emitting diodes (LEDs), such as an array of 2 W laser diodes having a wavelength ($\lambda$) of 830 nm, and a change in wavelength ($\Delta\lambda$) of 3 nm, such as laser diodes made by JDSU.

Camera 1800 can rely on a structured light principle where the displacement of an object is determined by variations of the geometry of a projected pattern. For example, infrared light source 1810 and diffraction grating 1812 can be used to project a pseudo-random pattern having varying intensities. Camera 1800 can also determine an expected pseudo-random pattern based on the projected pseudo-random pattern, and then determine variations in geometry by comparing the captured and expected pseudo-random patterns.

Camera 1800 can incorporate a near-infrared monochrome sensor (e.g. Microsoft/X853750001/VCA379C7130, 1200×1600 pixels), perhaps as part of infrared camera 1814, for measuring depth from the distortion between the projected and observed pseudo-random patterns. For reduce the back scattering, a pulse duration of infrared light source 1810 can be set much shorter than the time expected for emitted infrared light to travel to the target. Infrared camera 1814 can capture light in the near-infrared range and generate image(s) using the captured light, including but not limited to images of projected pseudo-random patterns of near-infrared light emitted by infrared light source 1810 and diffraction grating 1812. In some embodiments, infrared camera can generate images having a predetermined depth resolution or range of depth resolutions; e.g., a depth resolution of 1.5-2.5 mm.

Visible light source 1820 can use one or more light sources, such as visible light LEDs, to generate visible light. In some embodiments, visible light source 1820 can have blue-green filters and/or blue-green LEDs to generate visible light in the 450 to 480 nm range. For example, visible light source 1820 can be, or include, a Sea-View SV-Q10K 500 W Halogen Unit. Visible light in 450-480 nm range can match a blue-green transmission window of water, thus improving the contrast and range of operation. Polarizer 1822 can reduce glare and undesirable reflections from the environment. Polarizer 1822 also can detect changes in a polarization state of light scattered by water and suspended particles, allowing for enhanced contrast. Visible light camera 1814 can capture light in the visible light range and generate image(s) using the captured light.

Images generated by infrared camera 1814 and visible camera 1824 can be received by processor 1830 and provided to communication interface 1840. For example, processor 1830 can interleave depth-related images received from infrared camera 1814 with visible light images from visible light camera 1824 into pairs of images, where each pair of images includes a depth-related image and a visible-light image captured at substantially the same time; e.g., within 1/30th of a second of each other.

In some embodiments, processor 1830 can alternate activation of light sources 1810, 1820 at a rate based on a frame rate of camera 1800. For example, suppose camera 1800 is configured to generate N video frames per second, with N>1, and let a frame speed be X seconds, where X≤1/N. Then, light source 1810 can be activated to emit near-infrared light for 0.5X seconds and a depth-related image captured by near-infrared camera 1814 using the emitted near-infrared light, then light source 1820 can be activated to emit visible light for 0.5X seconds and a visible-light image captured by visible light camera 1824 using the emitted visible light. In particular of these embodiments, a single camera configured to capture light in both the visible-light range and near-infrared range can perform the functionality of infrared camera 1814 and visible light camera 1824 by capturing both images of the pair of images within the frame speed of X seconds.

In other embodiments, the pair of images includes a depth-related image and a visible light image captured; e.g., processor 1830 can activate both light sources 1810 and 1820 at the same time and both infrared camera 1814 and visible light camera 1824 can capture light emitted at the same time in the respective near-infrared and visible-light ranges. Thus, each pair of images can provide depth and visible light information about an environment captured at substantially the same time.

Figure 18B:
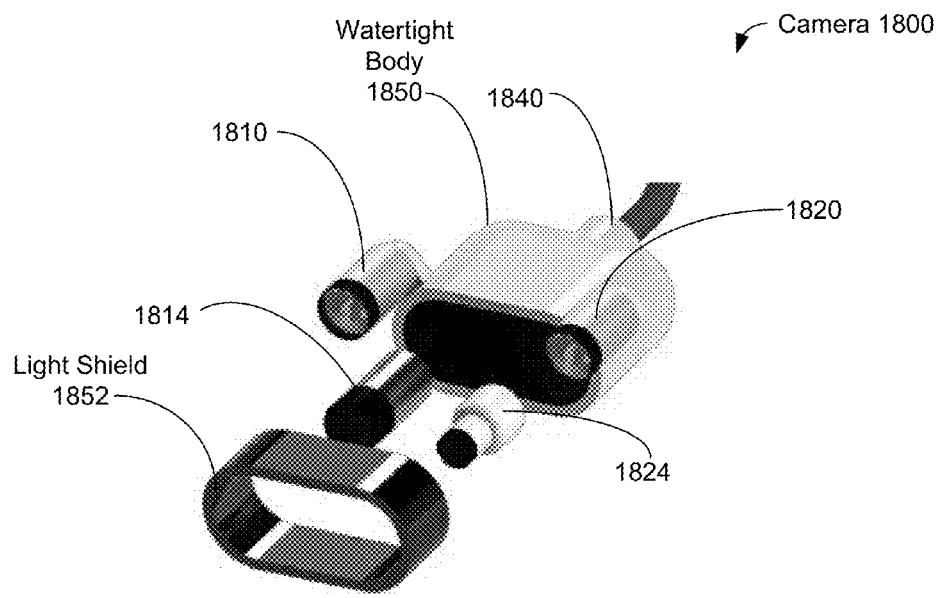
FIG. 18B is an exploded view of a camera configured to provide images for underwater haptic rendering, in accordance with an example embodiment.

FIG. 18B is an exploded view of camera 1800, in accordance with an example embodiment. FIG. 18B shows camera 1800 with infrared light source 1810, infrared camera 1814, visible light source 1820, visible light camera 1824, communication interface 1840, watertight body 1850, and light shield 1852. Watertight body 1850 can hold components of camera 1800 on and/or inside of body 1850. Light shield 1852 can shield cameras 1814, 1824 from direct light emitted from light sources 1810, 1820, and so reduce glare on images taken by cameras 1814, 1824.

For underwater applications, camera 1800 can be waterproofed. Camera 1800 can be enclosed in watertight body 1850 configured to isolate camera 1800 from the harm of water using materials that have little or no impact on optical performance. Camera 1800 can include water-tight connectors that allow external communication via optical fibers connected to communication interface 1840. In some embodiments not shown in FIG. 18A, camera 1800 can include a battery configured for powering camera 1800. In some embodiments, one or more adaptors can enable connection of camera 1800 to a borescope. The adapter(s) can combine near-infrared images and visible-light images, and recover the depth information from the near-infrared images using a wavelength-specific beam splitter.

Figure 18C:
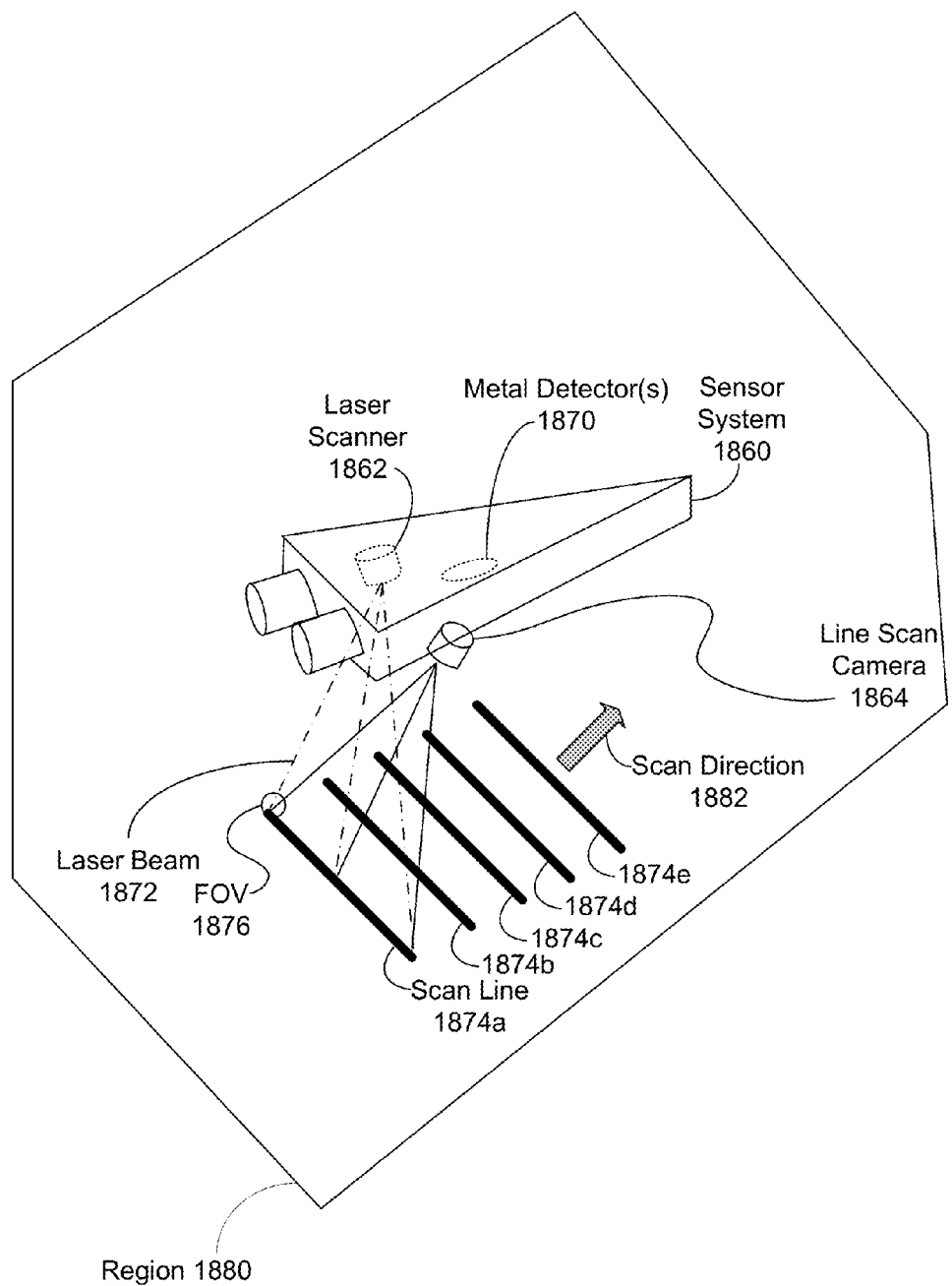
FIG. 18C depicts a sensor system, in accordance with an example embodiment.

FIG. 18C depicts a sensor system 1860, in accordance with an example embodiment. Sensor system 1860 includes metal detector(s) 1870 and a scanning camera system, where the scanning camera system has a laser scanner 1862 and line scan camera 1864. Metal detectors, such as metal detector(s) 1870, are discussed below in more detail in the context of at least FIGS. 24A through 27B.

In the example shown in FIG. 18C, sensor system 1860 is scanning in region 1880 along a scan direction 1882 upward and rightward. Laser scanner 1862 generates an illumination field using laser beams such as laser beam 1872—FIG. 18C show laser beams generated by laser scanner 1862 using dashed and dotted lines. Laser scanner 1862 can use using high power collimated laser lights to generate collimated laser beams with minimal cross sections, such as laser beam 1872. FIG. 18C shows that laser scanner 1860 is configured to emit laser beams, such as laser beam 1872 along scan lines, such as scan lines 1874a, 1874b, 1874c, 1874d, and 1874e, within region 1880.

Sensor system 1860 allows small individual elements of a target scene, such as a portion of region 1880 swept out by scan lines 1874a-1874e, to be illuminated one at a time with minimal backscatter. For example, FIG. 18C shows a field of view 1876 for line scan camera 1864 as a relatively small portion of region 1880. At the same time, a narrow field of view photodetector (not shown in FIG. 18C) can track field of view 1876 and reduce forward scatter from light reflected from the target scene.

Figure 19:
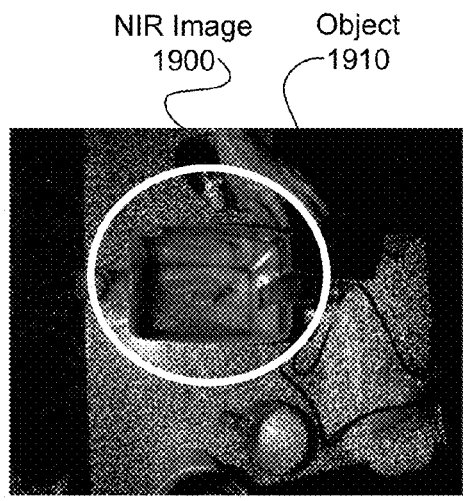
FIG. 19 is a near-infrared image of an object in clear water, in accordance with an example embodiment.

FIG. 19 shows near-infrared image 1900 of object 1910 in clear water, in accordance with an example embodiment. To capture image 1900, a near-infrared camera and light source, such as near-infrared camera 1814 and near-infrared light source 1810, were suspended about 85 cm (about 33.5 inches) above a flat surface. A container with clear water about 20 cm (about 7.9 inches) deep was placed on the flat surface below the near-infrared camera and light source. The near-infrared camera was aimed at the body of water. Then, the near-infrared light source generated a pseudo-random pattern and a near-infrared image, now image 1900, was captured by the near-infrared camera. The pseudo-random pattern is observable in FIG. 19 as dots scattered throughout image 1900; e.g., dots visible below and to either side of a white circle used to outline object 1900.

Figure 20A:
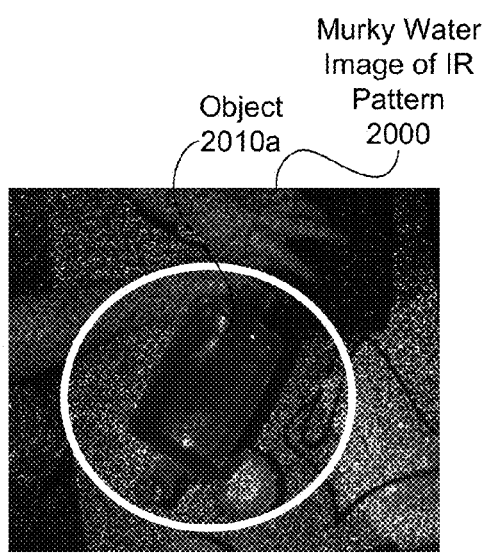
FIG. 20A is a near-infrared image of an object in murky water, in accordance with an example embodiment.

FIG. 20A is near-infrared image 2000 of an object in murky water, in accordance with an example embodiment. Image 2000 was captured using the same setup used for FIG. 19-a near-infrared camera and light source, such as near-infrared camera 1814 and near-infrared light source 1810, were suspended about 85 cm above a flat surface, about 20 cm of water was placed on a container above the flat surface, and the near-infrared camera aimed at the water. Then, as with image 1900, a pseudo-random pattern of near-infrared light was projected onto the water and a near-infrared image, now image 2000, was captured. Object 2010a of image 2000 is the same object as object 1910 of image 1900.

However, for image 2000, murky water was used rather than the clear water used for image 1900 of FIG. 19. FIG. 20A indicates that only part of the projected pattern makes it through the body of murky water.

Figure 20B:
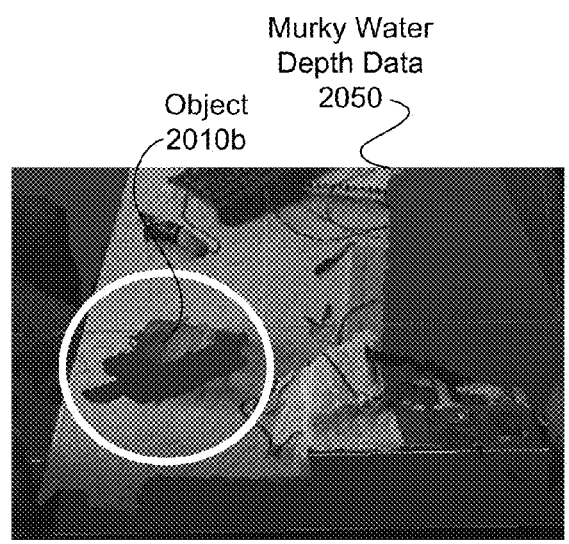
FIG. 20B is an image representing depth data related to the image of FIG. 20A, in accordance with an example embodiment.

FIG. 20B is image 2050 representing depth data related to image 2000 of FIG. 20A, in accordance with an example embodiment. The depth data was obtained by processing the partial projected pattern obtained from image 2050. The depth data can be distorted due to the index difference between air and water, but as long as the depth data can be obtained through a body of water, it can be corrected by software post-processing. Image 2050 shows object 2010b clearly, indicating that valid depth data for object 2010b was obtained even though only a partial projected pattern on object 2010a was obtainable from image 2010.

Figure 21:
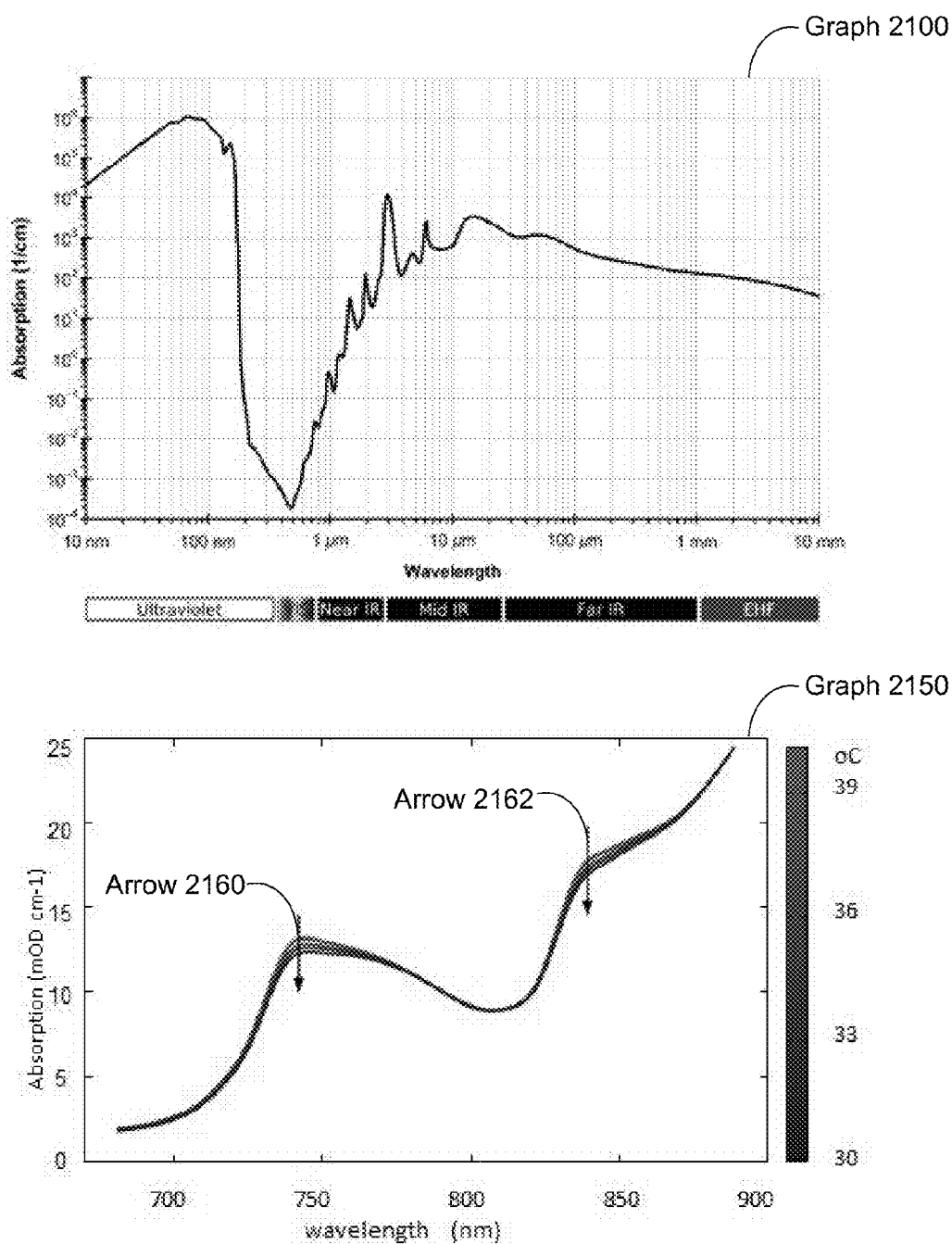
FIG. 21 shows a graph of light absorption in water versus light wavelength and a graph of light absorption in water versus light wavelength over a range of water temperatures, in accordance with an example embodiment.

FIG. 21 shows graph 2100 of light absorption in water versus light wavelength and graph 2150 of light absorption in water versus light wavelength over a range of water temperatures, in accordance with an example embodiment. Graph 2100, shown in the upper portion of FIG. 21, shows that the water absorption spectrum has a minimum near the NIR wavelength, indicating that the NIR wavelength is suitable for underwater. Graph 2150, shown in the lower portion of FIG. 21, shows water absorption for light in a range of wavelengths between 700 and 900 nm as a function of temperatures ranging from 30° C. to 40° C. with arrows 2160 and 2162 indicating a direction of temperature.

Resolving Dot Pattern Interference in Multiple Structured Light Cameras

The simultaneous use of multiple depth-enabled cameras; e.g., camera 1800 can extend coverage regions for haptic rendering, overcome occlusions, and enable complete full-circle captures of environments. In some cases, structured light sensing can degrade when multiple depth-enabled cameras are pointing at the same scene, due to continuous, non-modulated projection of pseudo-random patterns; e.g., as discussed above in the context of diffraction grating 1812 of FIG. 18A. The continuous, non-modulated projection of pseudo-random patterns can cause crosstalk when dot patterns of devices interfere with one another.

Herein are provided techniques and devices that can mitigate structured light crosstalk. In some embodiments, these techniques and devices can be utilized without modification of the internal electronics, firmware, or software of a depth-enabled camera and without degradation of the depth-enabled camera's frame rate.

One technique to eliminate crosstalk involves time multiplexing where a near-infrared light source associated with each camera in a system of cameras can be modulated and synchronized at a predetermined modulated time frequency.

Figure 22:
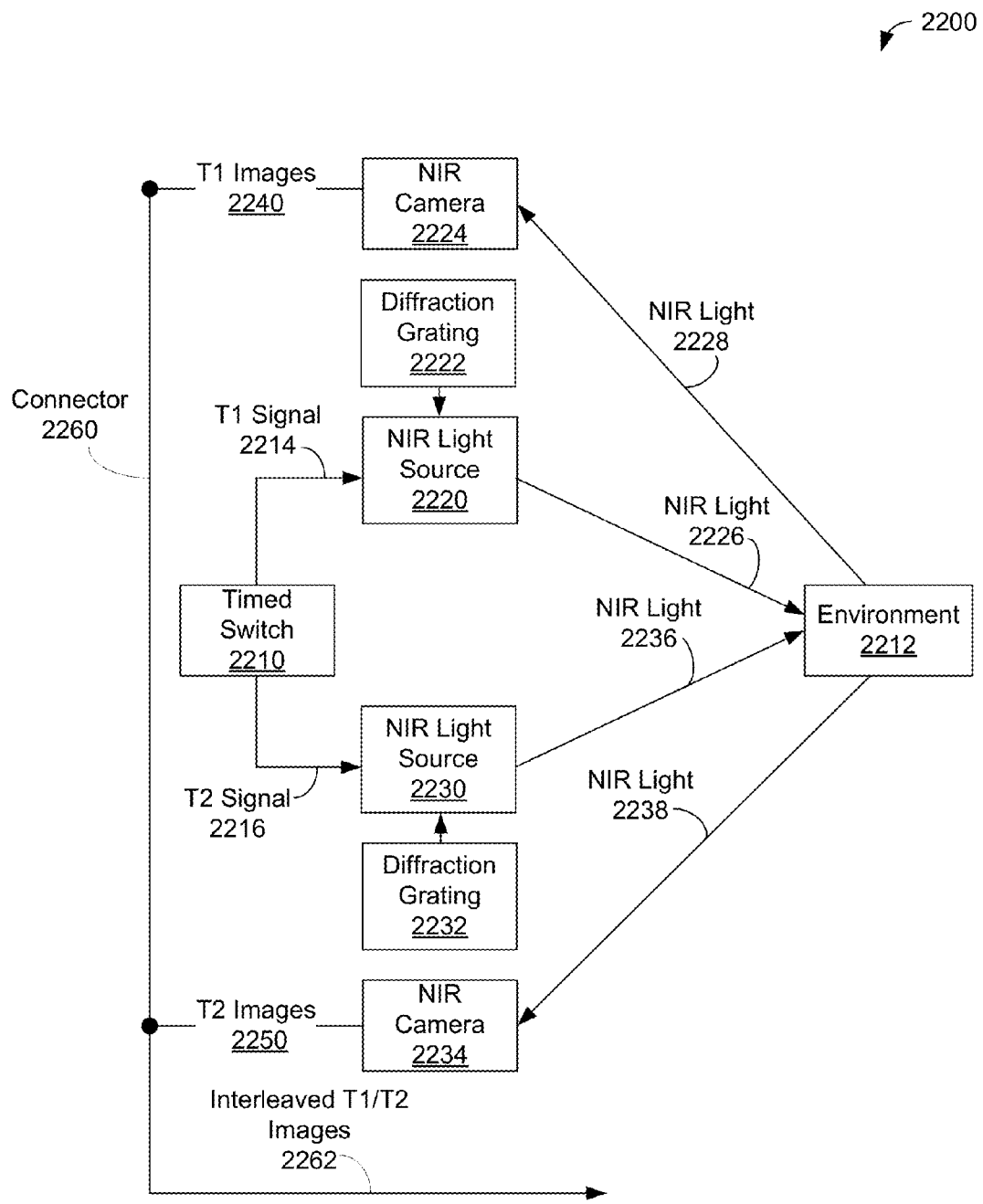
FIG. 22 is a block diagram of a time-multiplexed system of near-infrared cameras configured to capture images of an environment, in accordance with an example embodiment.

FIG. 22 is a block diagram of time-multiplexed system 2200 of near-infrared cameras 2224, 2234 configured to capture images of environment 2212, in accordance with an example embodiment. Timed switch 2210 can generate two periodic signals, T1 signal 2214 and T2 signal 2216, with both signals having the same period but only one signal is active at any specified time. For example, timed switch 2210 can use generate a square wave with equal active/inactive periods for T1 signal 2214 and an inverted version of the square wave for T2 signal 2216 (or vice versa). Other techniques for generating T1 signal 2214 and T2 signal 2216 can be used as well.

Then, when T1 signal 2214 is active, near-infrared light source 2220 can be activated. When activated, near-infrared light source 2220 can shine near-infrared light 2226 through diffraction grating 2222 and onto environment 2212. Subsequently, near-infrared camera 2224 can capture near-infrared light 2228 reflected from environment 2212 as an image of T1 images 2240. Near-infrared camera 2224 can place T1 images 2240 onto connector 2260.

When T2 signal 2216 is active, near-infrared light source 2230 can be activated. When activated, near-infrared light source 2230 can shine near-infrared light 2236 through diffraction grating 2232 and onto environment 2212. Subsequently, near-infrared camera 2234 can capture near-infrared light 2238 reflected from environment 2212 as an image of T2 images 2250. Near-infrared camera 2224 can place T2 images 2250 onto connector 2260 for use by to device(s) outside of system 2200. As T1 images 2240 are placed onto connector 2260 at times based on T1 signal 2214 and T2 images 2250 are placed onto connector 2260 at times based on T2 signal 2216, T1 images and T2 images can be interleaved in time as interleaved T1/T2 images 2262. As shown in FIG. 22, interleaved T1/T2 images 2262 can be sent from system 2200, perhaps for use by device(s) outside system 2200.

In other embodiments not shown in FIG. 22, more than two near-infrared cameras can be used. In these embodiments, each of N near-infrared cameras, N>2, can be assigned an equal, periodic, time interval; e.g., a periodic time slot. During an assigned time slot, a corresponding light source to the near-infrared camera can be illuminated, image(s) of environment 2212 can be captured by the near-infrared camera and the image(s) transmitted. Timeslots can be allocated in round-robin fashion to each of the N near-infrared cameras as long as images of environment 2212 are to be captured and transmitted.

In some embodiments, near-infrared cameras 2224, 2234 are active continuously. When a signal for corresponding camera is not active; e.g., T1 signal 2214 for NIR camera 2224, and T2 signal 2216 for near-infrared camera 2234, images generated by that camera can be considered to be invalid and so not be processed. To reduce any image processing applicable to interleaved T1/T2 images 2262, a shutter synchronized with T1 and T2 signals can be used to block or allow light from light sources 2220, 2230 so a corresponding camera captures light from a light source associated with the corresponding camera; e.g., light from light source 2220 is blocked by the shutter when T1 signal 2214 is not active and is allowed by the shutter when T1 signal 2214 is active.

Another technique to eliminate crosstalk involves is wavelength-division multiplexing where each near-infrared light source associated with a camera in a system of cameras has a different wavelength.

Figure 23:
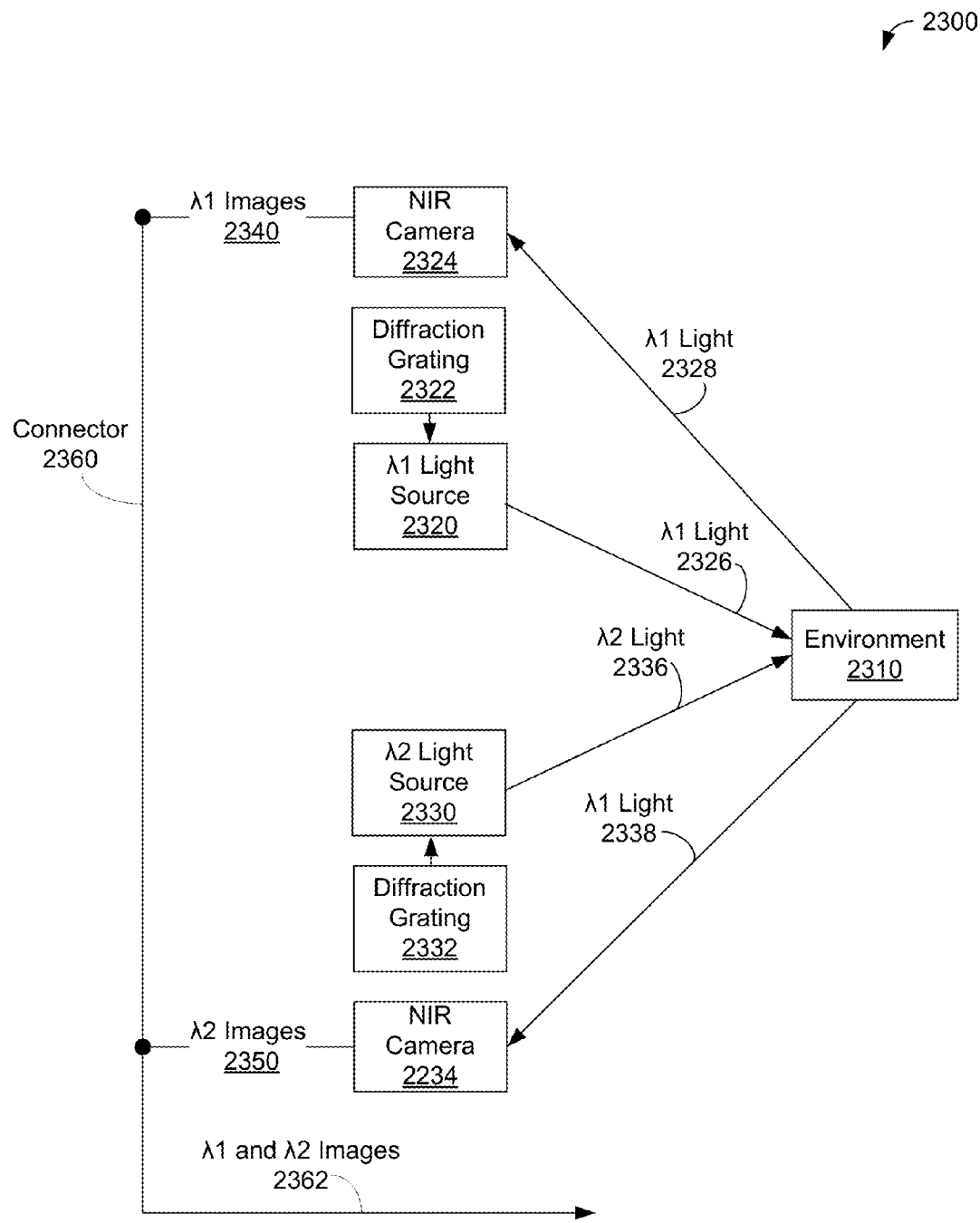
FIG. 23 is a block diagram of a frequency-multiplexed system of near-infrared cameras configured to capture images of an environment, in accordance with an example embodiment.

FIG. 23 is a block diagram of frequency-multiplexed system 2300 of near-infrared cameras 2324, 2334 configured to capture images of environment 2310, in accordance with an example embodiment. λ1 light source 2320 can be configured to emit light in a sub-range of the near-infrared range of frequencies, where the sub-range includes a wavelength λ1. Similarly, λ2 light source 2330 can be configured to emit light in a sub-range of the near-infrared range of frequencies, where the sub-range includes a wavelength λ2, where the sub-range including wavelength λ1 does not overlap the sub-range including wavelength λ2. For example, if λ1=820 nm and λ1=900 nm, the sub-range including λ1 can be 800-840 nm, and the sub-range including λ2 can be 880-920 nm. In some embodiments, the sub-range can include light of one frequency; e.g., using the previous example, the sub-range including λ1 can have one frequency of 820 nm and the sub-range including λ2 can have one frequency of 900 nm. Many other example values of λ1, λ2, and sub-ranges associated with λ1 and λ2 are possible as well.

λ1 light source 2320 can emit λ1 light 2326 that reaches environment 2310. Environment 2310 can reflect some or all of the light including frequency λ1 as λ1 light 2328 to near-infrared camera 2324. Subsequently, near-infrared camera 2324 can capture near λ1 light 2328 as an image of λ1 images 2340. Near-infrared camera 2324 can place λ1 images 2340 onto connector 2360.

λ1 light source 2323 can emit λ2 light 2336 that reaches environment 2310. Environment 2310 can reflect some or all of the light including frequency λ2 as λ2 light 2338 to near-infrared camera 2334. Subsequently, near-infrared camera 2334 can capture near λ1 light 2328 as an image of λ1 images 2350. Near-infrared camera 2324 can place λ2 images 2350 onto connector 2360.

As shown in FIG. 23, λ1 images and λ2 images can be sent from system 2300 as λ1 and λ2 images 2362, perhaps for use by device(s) outside system 2200. A device receiving λ1 and λ2 images 2362 can use filter(s) to ensure that images taken in light having a corresponding wavelength is detected and analyzed.

In other embodiments not shown in FIG. 23, more than two near-infrared cameras can be used. In these embodiments, each of N near-infrared cameras, N>2, can be assigned a non-overlapping frequency, and perhaps a non-overlapping sub-range of frequencies that includes the assigned frequency, within the near-infrared range of frequencies. Each camera can then have an associated light source configured to emit light with the assigned non-overlapping frequency (or emit light in the assigned sub-range of frequencies, if sub-ranges are assigned). The camera can capture light reflected from environment 2310 having the assigned non-overlapping frequency as an image, and send any captured images.

Metal Detecting Systems

A metal detector can work alongside a camera system, such as camera 1800, system 2200, or system 2300. For example, sensor system 1860 discussed above in the context of FIG. 18C includes both a camera and metal detector(s). An array of the metal detectors can be arranged around the camera system to allow simultaneous capture of 2D metal profiling data and images. The array of metal detectors can be arranged in a pattern; e.g., the array can be arranged in a cross pattern. In other scenarios, a metal detector or an array of metal detectors can be mounted on a vessel or near actuators, such as robotic arms, to map 2D or 3D metal profiles without using a visual or acoustical detector.

The metal profile, such as but not limited to a line scan, raster scan, or graph of magnetic flux over time, can be generated by an array of metal detectors moving across a target region while scanning. In some embodiments, the metal profile detector can utilize a phase array design where radiation pattern of the B field can be shifted by adjusting the phase difference between driving coils inside each metal sensor.

To reliably detect smaller metal items underwater; e.g., small munitions, a compact metal detector can be used. In some embodiments, the metal detector can have a relatively-small sensing resolution; e.g., a resolution of one square centimeter, and be capable of differentiating metal of different shapes and geometry using a fiber-optic sensor.

A metal detector can be based on a metal sensor having magnetostrictive materials. A magnetostrictive material is a material that changes shape or dimensions in the presence of a magnetic field. The metal detector operates by comparing a light signal sent through a loop of optical fiber coated with a magnetostrictive material with a light signal sent through an uncoated reference optical fiber. When the coated loop passes over para- or diamagnetic material, the magnetic field can induce strain in the fiber through magnetostriction of the coating. The induced strain can change the index of refraction within the coated fiber through the photoelastic effect, which changes the coated fiber's response relative to the reference. For example, the strain can causes a change in the length of the optical path. The metal detector can include an interferometer to measure the phase changes induced in the strained fiber relative to light passing through the reference coil. The presence of such phase changes indicates that metal has been detected.

Metal detectors using magnetostrictive materials can be configured to be relatively small in size. Further, magnetostrictive-based metal detectors can identify shapes or topographic features of metal targets while operating as a single metal detector or a metal detector in an array of metal detectors.

Figure 24A:
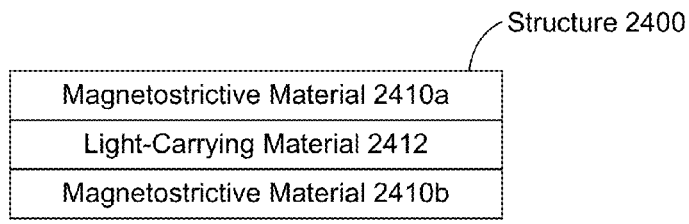
FIG. 24A shows a structure of a metal sensor, in accordance with an example embodiment.

FIG. 24A shows structure 2400 of a metal sensor, in accordance with an example embodiment. Structure 2400 includes a layer of magnetostrictive material 2410*a*, a light carrying material 2412, and another layer of magnetostrictive material 2410*b*. For example, the light carrying material can be an optical fiber and the magnetostrictive material can be a ferromagnetic polymer. Structure 2400 can be used when layers of magnetostrictive material 2410*a* and 2410*b* coat light carrying material.

Figure 24B:
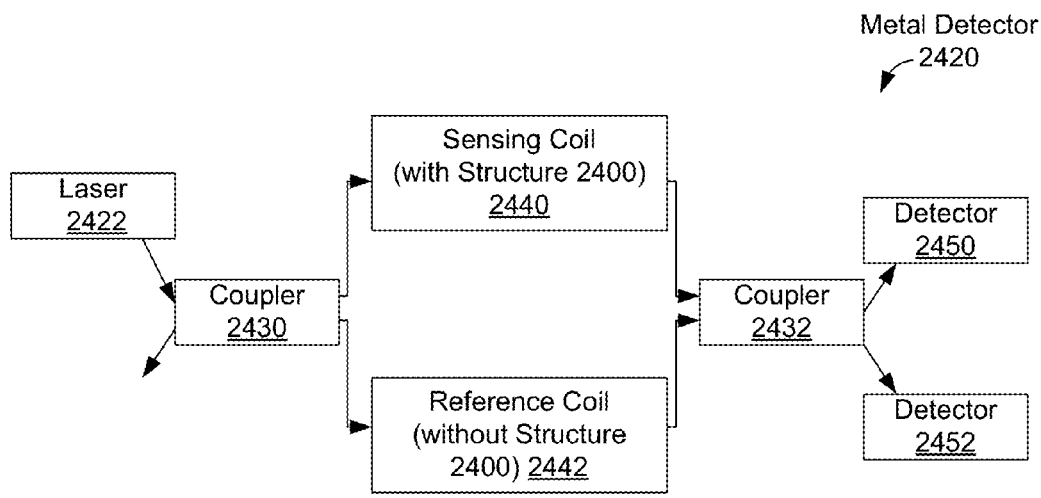
FIG. 24B is a diagram of an interferometer-based metal detector, in accordance with an example embodiment.

FIG. 24B is a diagram of interferometer-based metal detector 2420, in accordance with an example embodiment. Laser 2422 can send a light signal to optical coupler 2430, which is connected to both sensing coil 2440 and reference coil 2442. In metal detector 2420, each of coils 2440 and 2442 is configured to act as a sensing arm in an interferometer. Both sensing coil 2440 and reference coil 2442 include a light pathway; e.g., one or more optical fibers in the coil. However, sensing coil 2440 includes fiber coated with magnetostrictive material, while reference coil 2442 includes fiber that is not coated with magnetostrictive material; that is, coil 2440 includes structure 2400 while coil 2442 does not include structure 2400.

After light passes through each of sensing coil 2440 and reference coil 2442, the light is provided to optical coupler 2432 which can pass the light from sensing coil 2440 to detector 2452 and passes the light from reference coil 2440 to detector 2450. Light reaching detector 2450 can be compared to light reaching detector 2452; e.g., to determine phase changes in light indicating differences in sensing coil 2440 and reference coil 2442. That is, metal detector 2420 includes a Mach-Zehnder interferometer for detecting changes in light between coils 2440 and 2442 that represent the presence or absence of metal.

Figure 24C:
FIG. 24C is a diagram of another interferometer-based metal detector, in accordance with an example embodiment.

FIG. 24C is a diagram of interferometer-based metal detector 2460, in accordance with an example embodiment. Laser 2462 can send a light signal to optical coupler 2470, which is connected to detector 2472, sensing coil 2480, and reference coil 2480. Both sensing coil 2480 and reference coil 2482 include a light pathway; e.g., one or more optical fibers in the coil. In metal detector 2460, each of coils 2480 and 2482 is configured to act as a sensing arm in an interferometer. However, sensing coil 2480 includes fiber coated with magnetostrictive material, while reference coil 2482 includes fiber that is not coated with magnetostrictive material; that is, coil 2480 includes structure 2400 while coil 2482 does not include structure 2400.

Light passing through sensing coil 2480 can be provided to mirror 2490, which can reflect the provided light back through sensing coil 2480 and coupler 2470 to detector 2472. Similarly, light passing through reference coil 2482 can be provided to mirror 2492, which can reflect the provided light back through reference coil 2482 and coupler 2470 to detector 2472. Light reaching detector 2472 from sensing coil 2480 can be compared to light reaching detector 2472 from reference coil 2482 e.g., to determine phase changes in light indicating differences in sensing coil 2480 and reference coil 2482. That is, metal detector 2460 includes a Michelson interferometer for detecting changes in light between coils 2440 and 2442 that represent the presence or absence of metal.

Figure 25A:
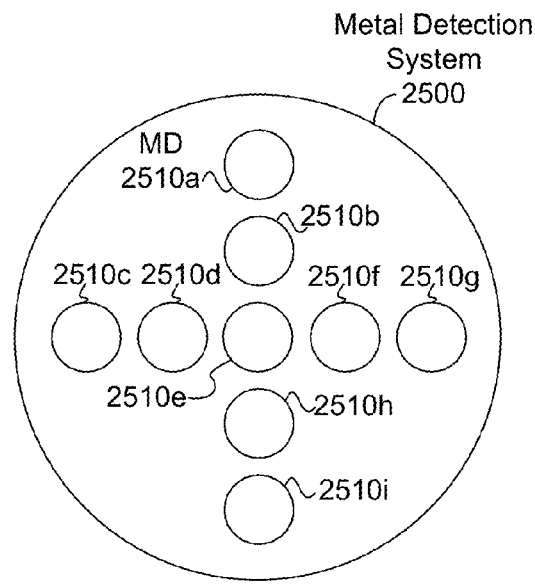
FIGS. 25A, 25B, and 25C are each a diagram of a metal detection system that includes multiple metal detectors, in accordance with an example embodiment.

FIG. 25A is a diagram of metal detection system 2500 that includes multiple metal detectors 2510*a*, 2510*b*, 2510*c*, 2510*d*, 2510*e*, 2510*f*, 2510*g*, 2510*h*, and 2510*i*, in accordance with an example embodiment. More specifically, metal detection system 2500 includes nine metal detectors 2510*a*, 2510*b*, 2510*c*, 2510*d*, 2510*e*, 2510*f*, 2510*g*, 2510*h*, and 2510*i* arranged in a cross-shaped pattern. Each of metal detectors 2510*a*, 2510*b*, 2510*c*, 2510*d*, 2510*e*, 2510*f*, 2510*g*, 2510*h*, and 2510*i* can be an interferometer-based metal detector, such as metal detector 2420 discussed above in more detail in the context of FIG. 24B or metal detector 2460 discussed above in more detail in the context of FIG. 24C.

In particular, each of metal detectors 2510*a*, 2510*b*, 2510*c*, 2510*d*, 2510*e*, 2510*f*, 2510*g*, 2510*h*, and 2510*i* can utilize magnetostrictive material as part of the interferometer-based metal detector. When one or more metal detectors 2510*a*-2510*i* are on an area having paramagnetic and/or diamagnetic material or move over an area having paramagnetic and/or diamagnetic material, the one or more metal detectors 2510*a*-2510*i* can detect a perturbation due to presence of a paramagnetic and/or diamagnetic material in the field. Based on a sequence of magnitude of the perturbation collected by the array of sensors, we can reconstruct the metal profile of the area the sensors pass over. The metal profile can include graphs, diagrams, line scans, and/or raster scans discussed below.

Figure 25B:
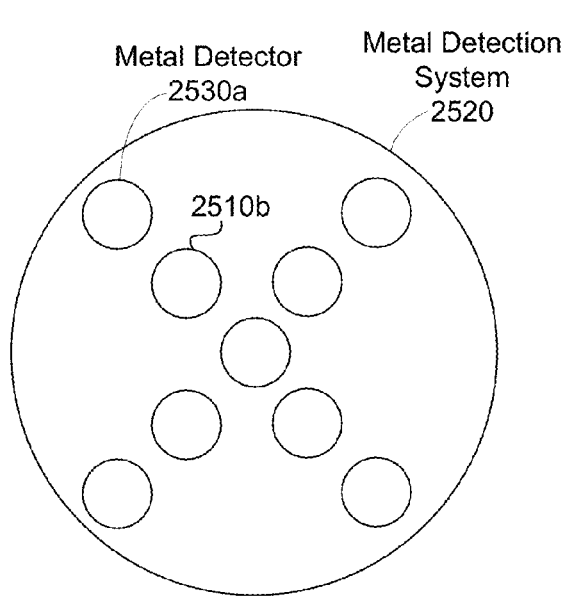

Other patterns of metal detectors than cross-shaped patterns can be used in metal detection systems. FIG. 25B is a diagram of metal detection system 2520 that includes multiple metal detectors, in accordance with an example embodiment. More specifically, metal detection system 2520 includes nine metal detectors 2530*a*, 2530*b*, 2530*c*, 2530*d*, 2530*e*, 2530*f*, 2530*g*, 2530*h*, and 2530*i* arranged in an X-shaped pattern. Each of metal detectors 2530*a*, 2530*b*, 2530*c*, 2530*d*, 2530*e*, 2530*f*, 2530*g*, 2530*h*, and 2530*i* can be an interferometer-based metal detector, such as metal detectors 2510*a*-2510*i* discussed above in the context of FIG. 25A.

Figure 25C:
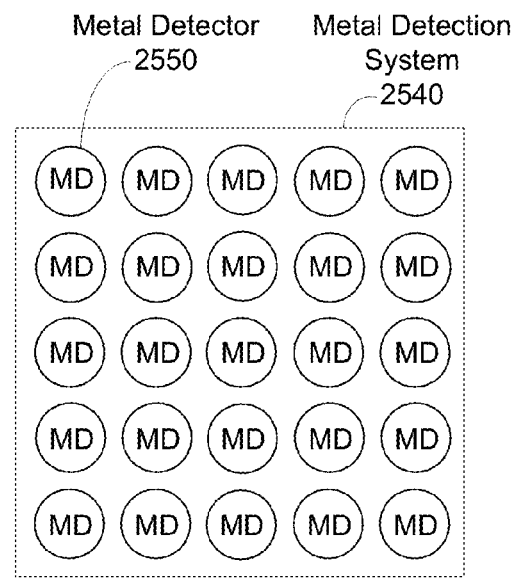

FIG. 25C is a diagram of metal detection system 2540 that includes multiple metal detectors, in accordance with an example embodiment. More specifically, metal detection system 2520 includes twenty-five metal detectors arranged in a grid-based pattern. Each of the twenty-five metal detectors, including metal detector 2550, are shown in FIG. 25C as marked with a "MD". Each metal detector in metal detection system 2540 can be an interferometer-based metal detector, such as metal detectors 2510*a*-2510*i* discussed above in the context of FIG. 25A. Other patterns of metal detectors and other metal detectors can be used in metal detection systems as well.

Figure 26A:
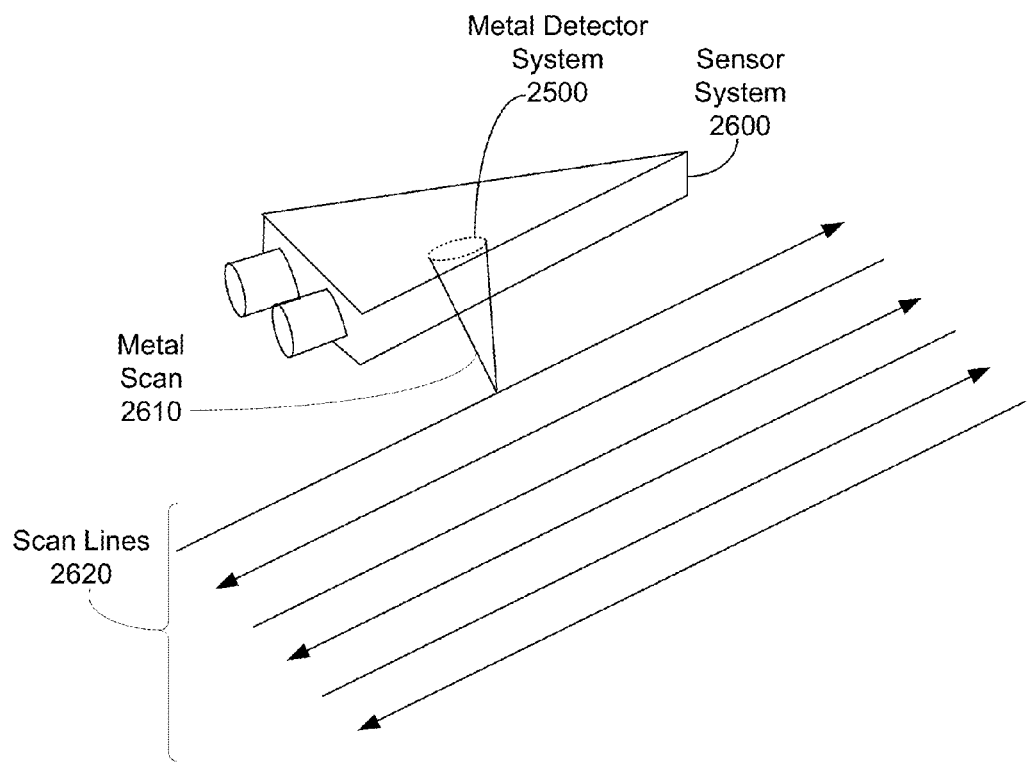
FIG. 26A depicts a sensor system using the metal detection system of FIG. 25A, in accordance with an example embodiment.

FIG. 26A depicts a sensor system using metal detection system 2500, in accordance with an example embodiment. Sensor system 2600 can generate a metal profile, such as a line scan, by moving an array of metal detectors 2510*a*-2510*i* in metal detection system 2500 along scan lines 2620 while the metal detectors are performing metal scans; e.g., searching for metallic objects below sensor system 2600. FIG. 26A shows metal detector(s) of metal detection system 2500 performing metal scan 2610 while sensor system 2600 is in motion along an upper-most scan line of scan lines 2620.

Figure 26B:
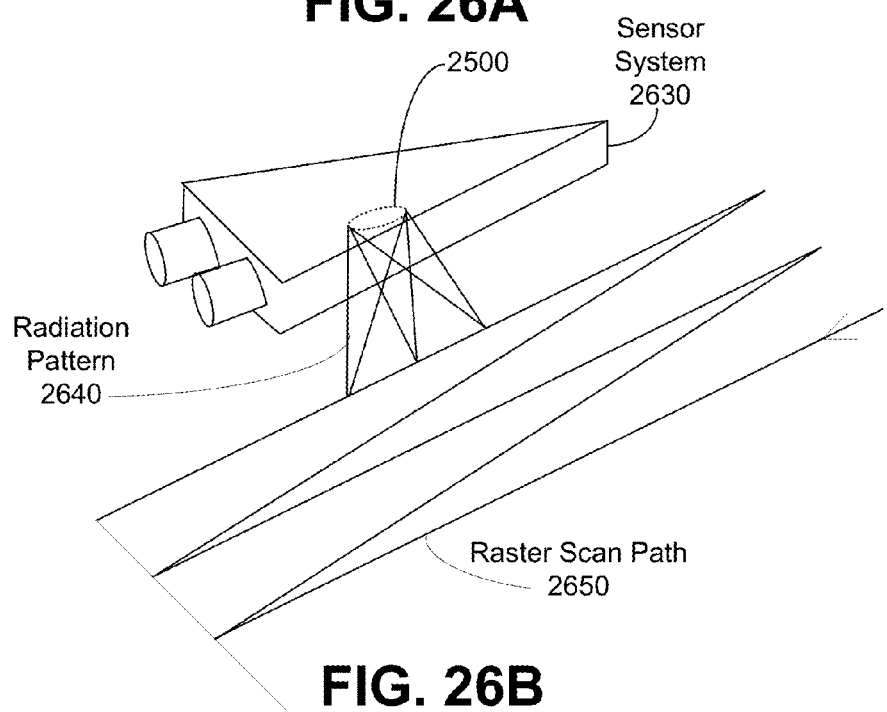
FIG. 26B depicts another sensor system using the metal detection system of FIG. 25A, in accordance with an example embodiment.

FIG. 26B depicts sensor system 2630 using metal detection system 2500, in accordance with an example embodiment. Sensor system 2630 can utilize a phase array design where radiation pattern of the B field 2640 can be shifted by adjusting a phase difference between driving coils inside each metal detector 2510*a*-2510*i* of metal detector system 2500 while metal detector 2510*a*-2510*i* are performing metal scans. A raster scan can be generated by adding phase differences in metal scans between the cross-pattern of metal detectors in metal detector system 2500. To generate the raster scan, sensor system 2640 can travel along raster scan path 2650, which is a zigzag shaped path as shown in FIG. 26B. The generated raster scan can be utilized as a metal profile for objects along raster scan path 2650.

In some embodiments, sensor system 2600 and/or sensor system 2630 can utilize more and/or different metal detection systems than metal detection system 2500; e.g., one or more metal detection systems 2520 and/or metal detection systems 2540 can be utilized as well as, or rather than metal detection system 2500 as shown in FIGS. 26A and 26B. Other techniques to generate metal profiles by using sensor systems equipped with metal detection systems are possible as well.

FIG. 27A is image 2710 of example metal objects 2702, 2704, 2706, in accordance with an example embodiment. Image 2710 shows an arrangement of metal objects, shown in left-to-right order, as rod 2702 running along a left-most side of image 2700, C clamp 2704 centrally placed in image 2700 and rod 2706 running along the left-most side of image 2700.

FIG. 27B is a graph 2720 of an output signal from an interferometer-based metal detector while scanning for metal objects in accordance with an example embodiment. Graph 2720 shows magnetic flux density in Gauss versus time as observed by an interferometer-based metal detector that is part of an array of metal detectors in a metal detection system; e.g., metal detector 2510*a* of metal detection system 2500. When the magnetic flux density reaches a peak, the metal detector has located a metal object.

Graph 2710 also includes inset 2730 with a copy of image 2710 including rod 2702, C Clamp 2704, and rod 2706, in accordance with an example embodiment. In the scan performed to generate graph 2720, the metal objects in image 2710 were scanned starting 0.2 after the beginning of the scan and the metal detector traveled in the direction of scan direction (SD) 2732 with respect to inset 2730.

Graph 2720 shows data for an interferometer based metal detector as an upper/darker grey line of graph 2720 and data for a Hall effect sensor as lower/lighter grey line of graph 2720. The in interferometer based metal detector and the Hall effect sensor were at the same position in metal detection system 2710. Graph 2720 shows that both sensors had similar responses; e.g., both the upper and lower lines of graph 2720 have similar peaks and valleys during the scan.

Specifically, at a time about 0.2 seconds as indicated by arrow 2740, the metal detector passed over rod 2702. Then, at a time at about 0.25 seconds as indicated by arrow 2742, the metal detector passed over a leftmost prong of C Clamp 2704 as shown in inset 2730 i.e., the top of the "C", and at a time at about 0.38 seconds as indicated by arrow 2744, the metal detector passed over a rightmost prong of C Clamp 2704; i.e., the bottom of the "C". Later, at a time of about 0.45 seconds as indicated by arrow 2746, the metal detector passed over rod 2706.

Graph 2720 shows that the metal detector indicated a peak in magnetic flux, and thus detected metal, when passing over rod 2702. The magnetic flux fell off from the peak of about 1200 Gauss at 0.2 seconds within approximately 0.01 seconds indicating that a narrow band of metal lie in the path of the metal detector while traveling along scan direction 2732. A similar peak is noted at about 0.45 seconds when the metal detector passed over rod 2706. Peaks were reached at about 0.25 seconds when the leftmost prong of C Clamp 2704 was detected and at about 0.38 seconds when the rightmost prong of C Clamp 2704, but in between these two peaks, the metal detector dropped to a relatively-low Gauss level of 1000 Gauss (or less) at about 0.30 to 0.32 seconds, indicating that the metal detector did not detect metal during that interval; i.e., the metal detector did not detect the body of C Clamp 2704 according to graph 2720.

FIG. 27C is a diagram 2750 of metal objects determined based on the data in FIG. 27B, in accordance with an example embodiment. Diagram 2750 of FIG. 27C is a 2D reconstructed map of rod 2702, C Clamp 2704, and rod 2706 shown in image 2710 of FIG. 27A using data from all metal detectors in a metal detection system while passing over the metal objects depicted in image 2710. Diagram 2750 shows each of rod 2752, C clamp 2754, and rod 2706 in the same relative positions as rod 2702, C Clamp 2704, and rod 2706 are shown in image 2710. Further, the general shape of rod 2702 and C Clamp 2704 of image 2710 are respectively reflected as rod 2752 and C Clamp 2754 of diagram 2750. Additionally, rod 2756 in diagram 2750 accurately depicts both the relative position and shape of rod 2706 shown in image 2710.

Figure 28:
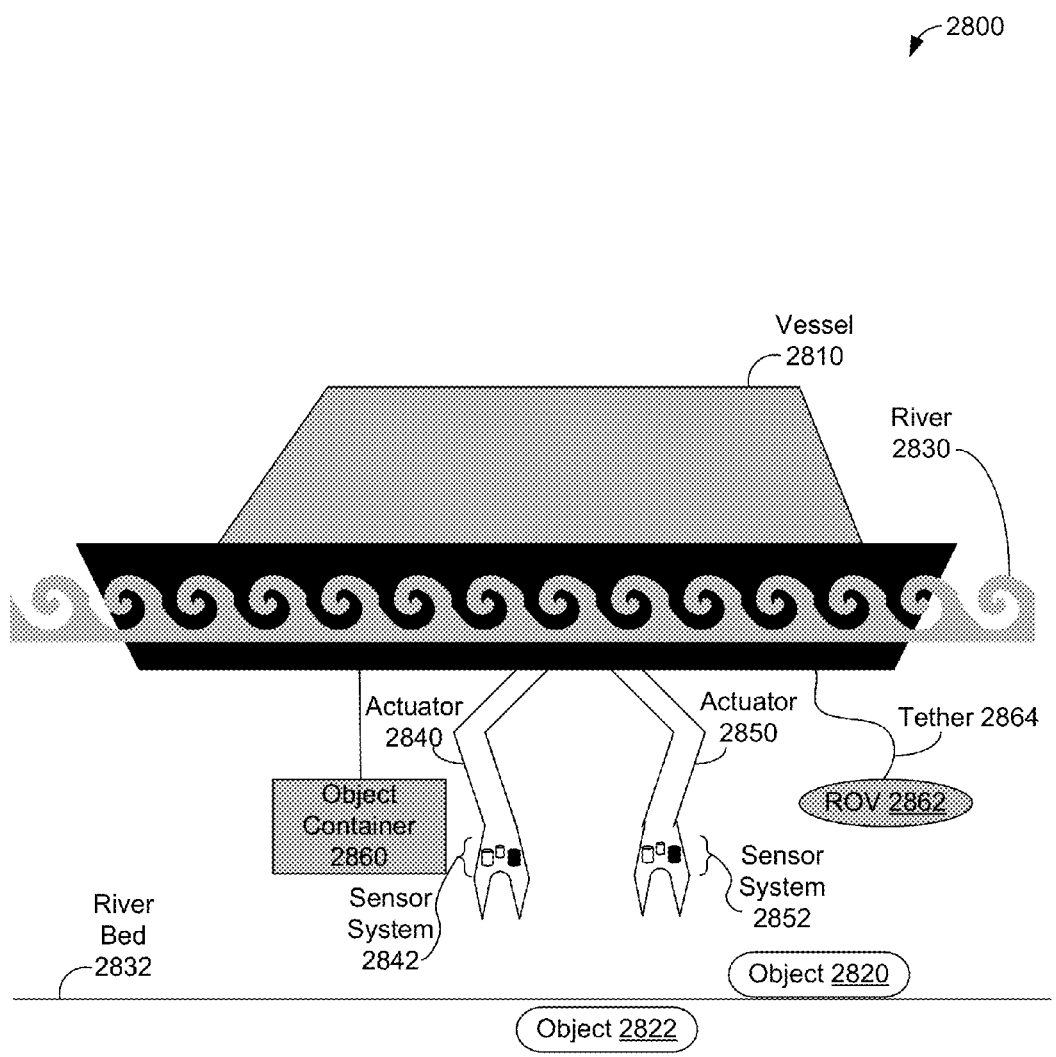
FIG. 28 illustrates a scenario where a vessel detects and retrieves an underwater object, in accordance with an example embodiment.

FIG. 28 illustrates a scenario 2800 where vessel 2810 detects and retrieves underwater objects 2820, 2822, in accordance with an example embodiment. In scenario 2800, vessel 2810 is floating in river 2830 above river bed 2832. In other scenarios, vessel 2810 can be used in an ocean, lake, pond, or other water environment than river 2830. Vessel 2810 has robot arms and hands acting as actuators 2840 and 2850. Each actuator 2840, 2850 can be partially or completely controlled by a remote operator; e.g., a human operator aboard vessel 2810 or located in another location. In some scenarios, the remote operator can adjust a level of automation of actuator 2840 and/or 2850; e.g., to be manually operated, semi-autonomously operated, or be fully autonomous operated.

The remote operator can receive feedback about the operation of actuator 2840 (and/or 2850) and/or about the environment using sensor system 2842 (and/or 2852). Sensor system 2842 (and/or 2852) can include one or more depth-enabled cameras including visible-light camera(s) and near-infrared camera(s), metal detectors/metal detection systems, and light sources including visible-light light source(s) and near-infrared light source(s) perhaps configured to emit pseudo-random patterns of light. In particular, sensor system 2842 (and/or 2852) can be configured to provide depth images, where the depth images can be used to generate haptic feedback for three or more degrees of freedom in controlling actuator 2840 (and/or 2850).

In scenario 2800, the remote operator of actuator 2840 (and/or 2850) operates actuator 2840 (and/or 2850) in accord with a task list, where the task list is configured to control virtual fixtures associated with tasks of retrieving object 2820 from river bed 2832 and object 2822 from under river bed 2832. Once an object is retrieved, the object can be placed in object container 2860; e.g., using a guidance fixture associated with the task list configured to guide actuator 2840 (and/or 2850) from a location of the object to a location of object container 2860. Other virtual fixtures, such as but not limited to forbidden-region fixtures, can be associated with the task list.

In scenario 2800, another remote operator can use remotely-operated vehicle 2862 to provide additional information regarding the environment including objects 2820, 2822, actuators 2840, 2850, river bed 2832, and/or river 2830. Remotely-operated vehicle 2862 can be attached to vessel 281 via tether 2864. Tether 2864 can include power and/or communication cables to enable remotely-operated vehicle 2862 to be powered from and/or communicate with vessel 2810. In other embodiments, remotely-operated vehicle 2862 can operate without tether 2864.

Figure 29:
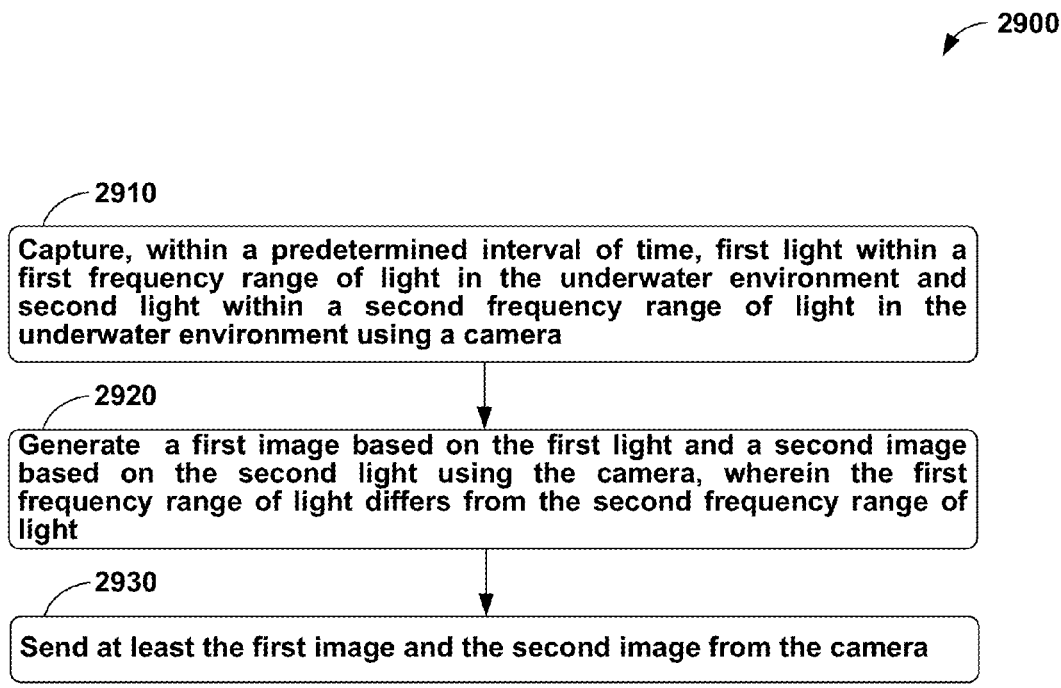
FIG. 29 is a flowchart of a method, in accordance with an example embodiment.

FIG. 29 is a flowchart of method 2900, in accordance with an embodiment. Method 2900 can be carried out with a depth-enabled camera, such as camera 1800. Method 2900 can start at block 2910, where a camera, such as camera 1800 discussed above in the context of at least FIGS. 18A and 18B, can capture, within a predetermined interval of time, first light within a first frequency range of light in the underwater environment and second light within a second frequency range of light in the underwater environment. In some embodiments, the first frequency range of light can include a range of frequencies of light between 450 nanometers (nm) and 480 nm. Then, the second frequency range of light of frequencies can include a range of frequencies of light between 825 and 835 nm.

At block 2920, the camera can generate a first image based on the first light and a second image based on the second light. The first frequency range of light can differ from the second frequency range of light.

At block 2930, the camera can send at least the first image and the second image. In some embodiments, sending at least the first image and the second image from the camera can include: generating a predetermined number of frames per second, where each frame includes a first frame image based on light within the first frequency range received at a specified time and a second frame image based on light within the second frequency range captured at the specified time, and sending the predetermined number of frames per second from the camera. In particular of these embodiments, the predetermined number of frames per second can be a number N, with N>1. Then, the predetermined interval of time can be less than or equal to 1/N seconds.

In some embodiments, the camera can include a first light emitting diode (LED) and a second LED. Then, method 2900 can further include: generating light within the first frequency range of light using the first LED and generating light within the second frequency range of light using the second LED. In particular of these embodiments, the camera further includes diffraction grating. Then, generating light within the second frequency range of light can include the scattering the light generated by the second LED into a pseudo-random pattern of light within the second frequency range using the diffraction grating. In more particular of these embodiments, method 2900 can further include capturing the pseudo-random pattern of light within the second frequency range using the camera, and determining distortion within the second frequency range of light by comparing the captured pseudo-random pattern of light to an expected pseudo-random pattern of light.

In other embodiments, the camera can include a polarizer. Then, method 2900 can further include reducing reflections in at least one image of the first image and the second image using the polarizer. In still other embodiments, the camera can include an optical adaptor. Then, method 2900 can further include separating light received at the device into the first light and the second light using the optical adaptor. In yet other embodiments, the first image and second image are configured to be utilized for generating haptic feedback.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include physical and/or non-transitory computer readable media such as computer-readable media that stores data for short periods of time like register memory, processor cache, and random access memory (RAM). The computer readable media may also include physical and/or non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

The terms physical and/or tangible computer-readable medium and physical and/or tangible computer-readable media refer to any physical and/or tangible medium that can be configured to store instructions for execution by a processor, processing unit and/or computing device. Such a medium or media can take many forms, including but not limited to, non-volatile media and volatile media. Non-volatile media includes, for example, read only memory (ROM), flash memory, magnetic-disk memory, optical-disk memory, removable-disk memory, magnetic-tape memory, hard drive devices, compact disc ROMs (CD-ROMs), direct video disc ROMs (DVD-ROMs), computer diskettes, and/or paper cards. Volatile media include dynamic memory, such as main memory, cache memory, and/or random access memory (RAM). Many other types of tangible computer-readable media are possible as well. As such, the herein-described data storage can comprise and/or be one or more physical and/or tangible computer-readable media.

Moreover, a block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method, comprising:
receiving first depth data about an environment at a computing device;
generating a first plurality of points from the first depth data using the computing device, wherein the first depth data comprise depth data about a target object in the environment;
determining a virtual tool using the computing device, wherein the virtual tool is specified in terms of a translation component for the virtual tool and a rotation component for the virtual tool;
determining a virtual fixture providing an overlay of sensory information using the computing device, wherein the virtual fixture is associated with one or more points related to the target object, and wherein the virtual fixture comprises one or more of:
a guidance fixture configured to define a guidance region represented by the depth data about the target object where the virtual tool is permitted to enter, and
a forbidden-region fixture configured to define a forbidden region represented by the depth data about the target object where the virtual tool is not permitted to enter;
determining a first force vector between the virtual tool and the virtual fixture using the computing device by at least:
determining a bounding box for the virtual tool based on a projection of the virtual tool onto the first depth data, and
determining a number of neighboring points of the first plurality of points, wherein each neighboring point is within the bounding box; and
sending, from the computing device, a first indication of haptic feedback based on the first force vector.

2. The method of claim 1, wherein the virtual fixture comprises a guidance fixture,
and wherein determining the first force vector comprises:
determining whether an interface point associated with the virtual tool is within the guidance region of the guidance fixture, and
after determining that the interface point is within the guidance region, determining that the first force vector comprises a force vector toward the target object.

3. The method of claim 1, wherein the virtual fixture comprises a forbidden-region fixture, and wherein determining the first force vector comprises:

determining whether an interface point associated with the virtual tool is near or within the forbidden region of the forbidden-region fixture, and after determining that the interface point is within the forbidden region, determining that the first force vector comprises a force vector away from the target object.

4. The method of claim 1, wherein the computing device is configured to communicate with a controllable mechanism, wherein sending the indication of haptic feedback based on the force vector from the computing device comprises sending the indication of haptic feedback based on the force vector from the computing device to the controllable mechanism, and wherein the method further comprises:

providing haptic feedback based on the indication of haptic feedback using the controllable mechanism.

5. The method of claim 4, wherein determining the virtual fixture comprises:

receiving, at the computing device, input specifying one or more boundaries of the virtual fixture using the controllable mechanism; and designating the virtual fixture based on the input specifying one or more boundaries of the virtual fixture.

6. The method of claim 1, wherein the first depth data comprises first image data and corresponding first depth values, and wherein the method further comprises:

generating a virtual environment based on the first image data and corresponding first depth values.

7. The method of claim 6, wherein the virtual environment comprises a first object related to the target object, and wherein the method further comprises:

determining a contact between the first object and the virtual tool.

8. The method of claim 1, wherein the first depth data comprises data about an input plurality of points in the environment, and wherein determining the first plurality of points comprises:

generating a filtered plurality of points by filtering the input plurality of points using a bilateral filter; and determining a normal vector for each point in the filtered plurality of points.

9. The method of claim 8, wherein the computing device comprises a graphics processing unit (GPU), and wherein determining the normal vector for each point in the filtered plurality of points comprises determining the normal vector for each point in the filtered plurality of points using the GPU.

10. The method of claim 1, wherein determining the virtual tool comprises representing the virtual tool using a plurality of voxels, wherein each voxel has a voxel size in each of three dimensions, and wherein the voxel size for each of the three dimensions is a same size.

11. The method of claim 1, wherein the environment comprises an underwater environment.

12. The method of claim 1, wherein the method further comprises:

determining whether the number of neighboring points of the first plurality of points indicates either there are zero neighboring points of the first plurality of points within the bounding box or more than zero neighboring points of the first plurality of points within the bounding box; and in response to determining that the number of neighboring points of the first plurality of points indicates that there are zero neighboring points of the first plurality of points within the bounding box:

determining that the virtual tool is in a free-motion state, and moving the virtual tool in a direction and a distance, wherein the direction is based on the translation component, and wherein the distance is bounded by a voxel size.

13. The method of claim 12, wherein the method further comprises:

in response to determining that the number of neighboring points of the first plurality of points indicates that there are more than zero neighboring points of the first plurality of points within the bounding box:

determining a depth for each neighboring point with respect to the virtual tool;

determining in-contact neighboring points from the neighboring points of the first plurality of points within the bounding box, wherein each in-contact neighboring point has a corresponding depth of zero;

determining in-collision neighboring points from the neighboring points of the first plurality of points within the bounding box, wherein each in-collision neighboring point has a corresponding depth less than zero;

in response to determining that no in-collision neighboring points are determined and to determining at least one in-contact neighboring point is determined:

determining a first constrained acceleration for the virtual tool based on the at least one in-contact neighboring point, and moving the virtual tool in a direction based on the first constrained acceleration.

14. The method of claim 13, wherein the method further comprises:

in response to determining that at least one in-collision neighboring point is determined:

determining a second constrained acceleration for the virtual tool based on the at least one in-collision neighboring point; and moving the virtual tool in a direction based on the second constrained acceleration.

15. The method of claim 1, wherein the virtual fixture comprises a forbidden-region fixture, and wherein the first indication of haptic feedback comprises an indication of haptic feedback indicating a slowing of movement within the forbidden region.

16. The method of claim 1, further comprising:

controlling a motion of at least one virtual object within a virtual environment, wherein the virtual environment comprises the at least one virtual object and at least one real surface.

17. An article of manufacture, comprising a non-transitory computer-readable storage medium storing instructions that, upon execution by a processor of a computing device, cause the computing device to perform functions comprising:

receiving first depth data about an environment;

generating a first plurality of points from the first depth data, wherein the first depth data comprise depth data about a target object in the environment;

determining a virtual tool specified in terms of a translation component for the virtual tool and a rotation component for the virtual tool;

determining a virtual fixture providing an overlay of sensory information using the computing device, wherein the virtual fixture is associated with one or more points related to the target object, and wherein the virtual fixture comprises one or more of:

a guidance fixture configured to define a guidance region represented by the depth data about the target object where the virtual tool is permitted to enter, and a forbidden-region fixture configured to define a forbidden region represented by the depth data about the target object where the virtual tool is not permitted to enter;

determining a first force vector between the virtual tool and the virtual fixture by at least:
  determining a bounding box for the virtual tool based on a projection of the virtual tool onto the first depth data, and
  determining a number of neighboring points of the first plurality of points, wherein each neighboring point is within the bounding box; and sending a first indication of haptic feedback based on the first force vector.

18. The article of manufacture of claim 17, wherein the virtual fixture comprises a guidance fixture,
  and wherein determining the first force vector comprises:
    determining whether an interface point associated with the virtual tool is within the guidance region of the guidance fixture, and
    after determining that the interface point is within the guidance region, determining that the first force vector comprises a force vector toward the target object.

19. A computing device, comprising:
  a processor; and
  data storage, storing instructions that, upon execution by the processor, cause the computing device to perform functions comprising:
    receiving first depth data about an environment;
    generating a first plurality of points from the first depth data, wherein the first depth data comprise depth data about a target object in the environment;
    determining a virtual tool specified in terms of a translation component for the virtual tool and a rotation component for the virtual tool;
    determining a virtual fixture providing an overlay of sensory information using the computing device, wherein the virtual fixture is associated with one or more points related to the target object, and wherein the virtual fixture comprises one or more of:
      a guidance fixture configured to define a guidance region represented by the depth data about the target object where the virtual tool is permitted to enter, and
      a forbidden-region fixture configured to define a forbidden region represented by the depth data about the target object where the virtual tool is not permitted to enter;
    determining a first force vector between the virtual tool and the virtual fixture by at least:
      determining a bounding box for the virtual tool based on a projection of the virtual tool onto the first depth data, and
      determining a number of neighboring points of the first plurality of points,
    wherein each neighboring point is within the bounding box; and
    sending a first indication of haptic feedback based on the first force vector.

20. The computing device of claim 19, wherein the virtual fixture comprises a guidance fixture,
  and wherein determining the first force vector comprises:
    determining whether an interface point associated with the virtual tool is within the guidance region of the guidance fixture, and
    after determining that the interface point is within the guidance region, determining that the first force vector comprises a force vector toward the target object.

* * * * *